United States Patent
Bürli et al.

(10) Patent No.: US 6,777,425 B2
(45) Date of Patent: Aug. 17, 2004

(54) ISOQUINOLINE COMPOUNDS HAVING ANTIINFECTIVE ACTIVITY

(75) Inventors: Roland W. Bürli, San Francisco, CA (US); Peter Jones, San Francisco, CA (US); Jacob A. Kaizerman, Redwood City, CA (US); Wenhao Hu, San Mateo, CA (US)

(73) Assignee: Genesoft Pharmaceuticals, Inc., So. San Francisco, CA (US)

( * ) Notice: Subject to any disclaimer, the term of this patent is extended or adjusted under 35 U.S.C. 154(b) by 0 days.

(21) Appl. No.: 10/165,857

(22) Filed: Jun. 6, 2002

(65) Prior Publication Data

US 2003/0083268 A1 May 1, 2003

Related U.S. Application Data

(60) Provisional application No. 60/333,830, filed on Nov. 27, 2001, and provisional application No. 60/298,206, filed on Jun. 13, 2001.

(51) Int. Cl.[7] .......................... C07D 217/02; A61K 31/47

(52) U.S. Cl. ........................................ 514/307; 546/146

(58) Field of Search ........................... 546/146; 514/307

(56) References Cited

U.S. PATENT DOCUMENTS

| | | | |
|---|---|---|---|
| 5,395,849 | A | 3/1995 | Wittman et al. |
| 5,545,640 | A | 8/1996 | Beaulieu et al. |
| 5,698,674 | A | 12/1997 | Bruice et al. |
| 5,844,110 | A | 12/1998 | Gold |
| 5,852,011 | A | 12/1998 | Matsunaga et al. |
| 5,998,140 | A | 12/1999 | Dervan et al. |
| 6,090,947 | A | 7/2000 | Dervan et al. |
| 6,143,901 | A | 11/2000 | Dervan |

FOREIGN PATENT DOCUMENTS

| | | | |
|---|---|---|---|
| WO | WO 96/26950 | | 9/1996 |
| WO | WO 97/25351 | * | 7/1997 |
| WO | WO 98/35702 | | 8/1998 |
| WO | WO 98/37066 | | 8/1998 |
| WO | WO 98/37067 | | 8/1998 |
| WO | WO 98/37087 | | 8/1998 |
| WO | WO 98/43663 | | 10/1998 |
| WO | WO 98/45284 | | 10/1998 |
| WO | WO 98/49142 | | 11/1998 |
| WO | WO 98/50582 | | 11/1998 |
| WO | WO 98/52614 | | 11/1998 |
| WO | WO 99/00364 | | 1/1999 |
| WO | WO 00/15209 | | 3/2000 |
| WO | WO 00/15773 | | 3/2000 |
| WO | WO 0121615 | * | 9/2000 |
| WO | WO 01/19792 A1 | | 3/2001 |
| WO | WO 01/21615 | | 3/2001 |
| WO | WO 01/74898 A2 | | 10/2001 |

OTHER PUBLICATIONS

Sen, Chemical Abstracts, vol. 71, No. 1, col. 1, Abstract 12986e, Jul. 7, 1969.*

Bremer, et al., Recognition of the DNA Minor Groove by Pyrrole–Imidazole polyamides: Comparison of Desmethyl- and N–Methylpyrrole, Bioorganic & Medicinal Chemistry 8 (2000), pp 1947–1955.

Bailly, et al., Sequence–Specific DNA Minor Groove Binders. Design and Synthesis of Netropsin and Distamycin Analogues, Bioconjugate Chemistry, vol. 9, No. 5 (Sep./Oct. 1998).

White, et al., On the Pairing Rules for Recognition in the Minor Groove of DNA by Pyrrole–Imidazole Polyamides, Chemistry & Biology 1997, vol. 4, No. 8.

Wade, et al., Design of Peptides that Bind in the Minor Groove of DNA at 5′–(A,T)G(A,T)C(A,T)–3′ Sequences by a Dimeric Side–by–Side Motif, Journal of the American Chemical Society, 1992, 114.

Mrksich et al., Hairpin Peptide Motif. A New Class of Oligopeptides for Sequence–Specific Recognition in the Minor Groove of Double–Helical DNA, Journal of the American Chemical Society, 1994, 116.

Baird et al., Solid Phase Synthesis of Polyamides Containing Imidazole and Pyrrole Amino Acids, J. Am. Chem. Soc. 1996, 118, 6141–6146.

Floreancig et al., Recognition of the Minor Groove of DNA by Hairpin Polyamides Containing α–Substituted–β–Amino Acids, J. Am. Chem. Soc. 2000, 122, 6342–6350.

Trauger et al., Recognition of DNA by Designed Ligands at Subnanomolar Concentrations, Nature, vol. 382, (Aug. 1996).

White et al., Recognition of the Four Watson–Crick Base Pairs in the DNA Minor Groove by Synthetic Ligands, Nature, vol. 391, (Jan. 1998).

Stephen Neidle, DNA Minor–Groove Recognition by Small Molecules, Nat. Prod. Rep., 2001, 18, 291–309.

Kelly et al., Binding Site Size Limit of the 2:1 Pyrrole–Imidazole Polyamide–DNA Motif, Proc. Natl. Acad. Sci. USA, vol. 93, pp. 6981–6985 (Jul. 1996).

(List continued on next page.)

Primary Examiner—Zinna Northington Davis
(74) Attorney, Agent, or Firm—Townsend and Townsend and Crew LLP

(57) ABSTRACT

Isoquinoline compounds having the formula

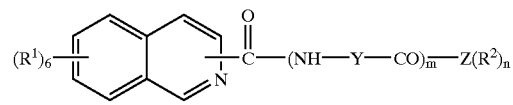

where $R^1$, $R^2$, Y, m, n, and Z are as defined herein, bind to the minor groove of DNA and have antifungal and antibacterial activity.

23 Claims, 9 Drawing Sheets

Figure 1A:
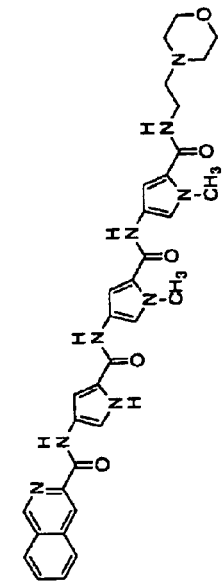
Figure 1A:
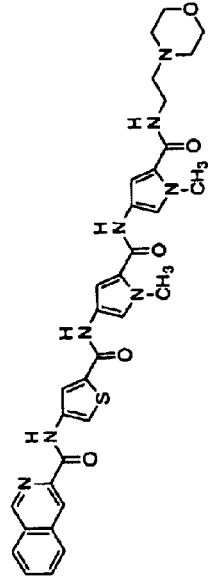
Figure 1A:
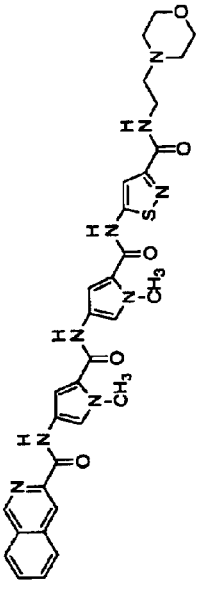
Figure 1A:
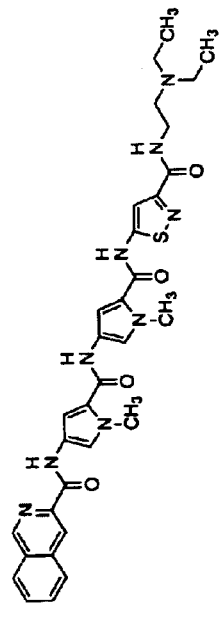
Figure 1A:
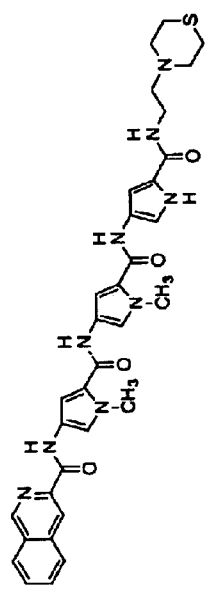
Figure 1A:
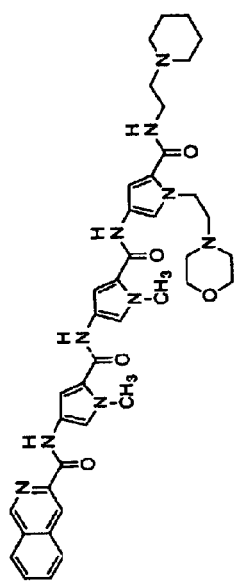
Figure 1A:
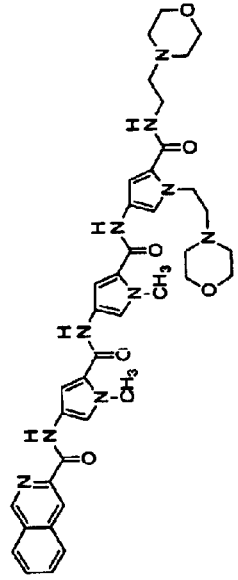
Figure 1A:
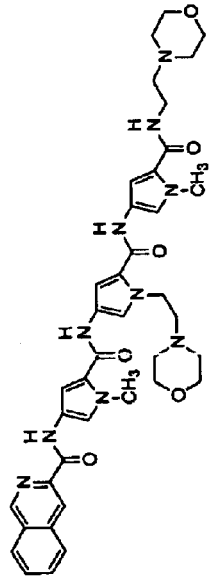
Figure 1B:
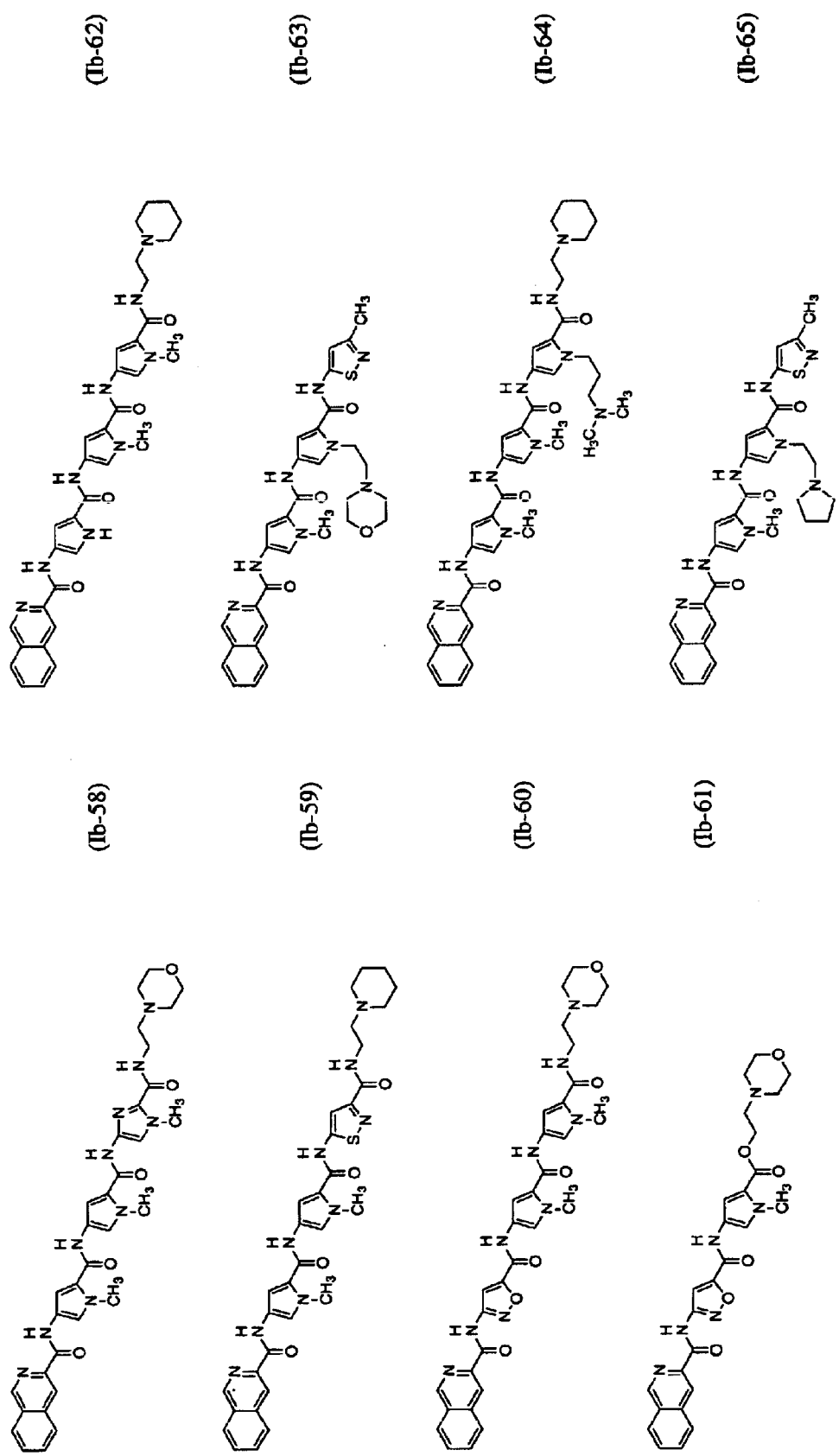
Figure 1C:
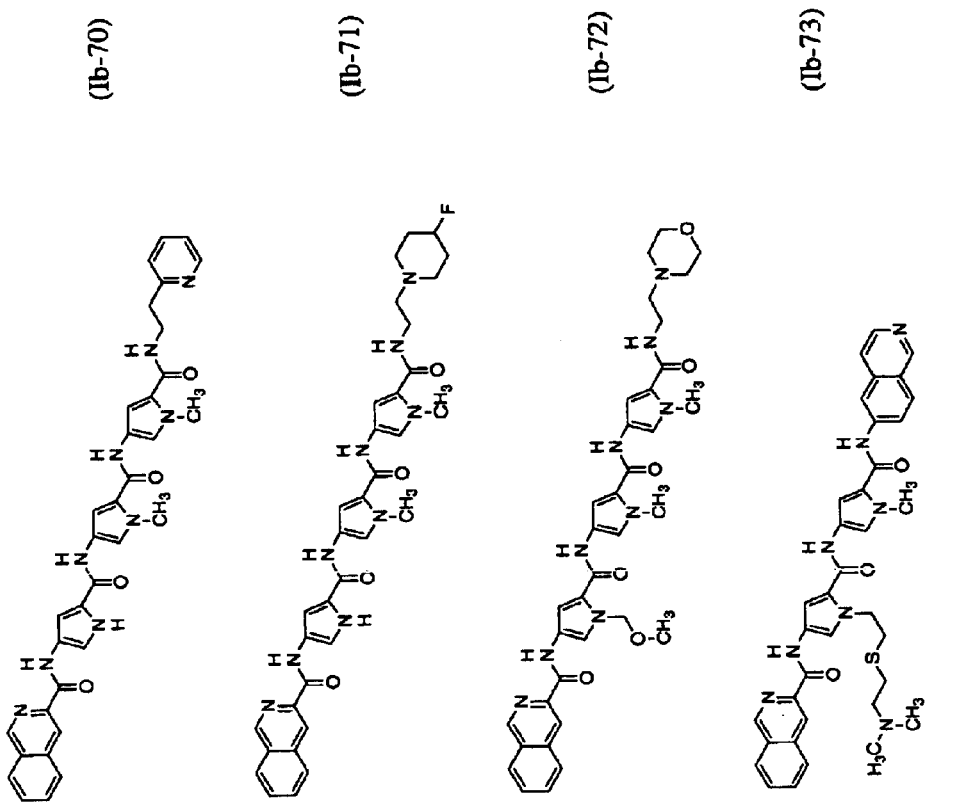
Figure 1C:
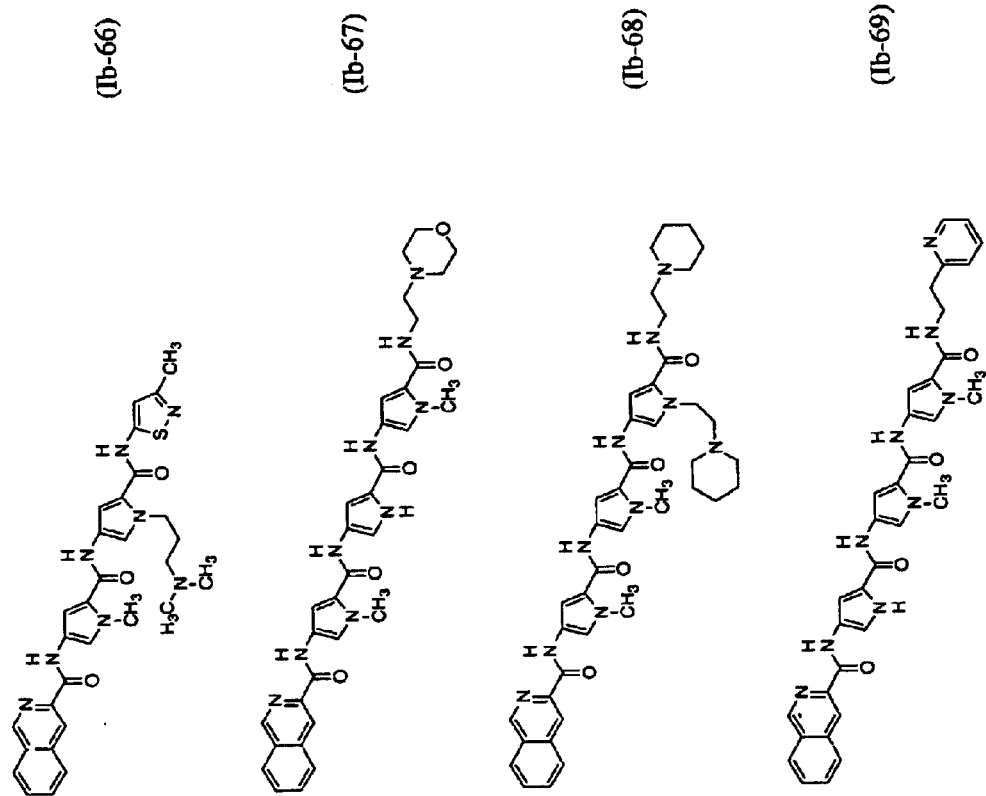
Figure 1D:
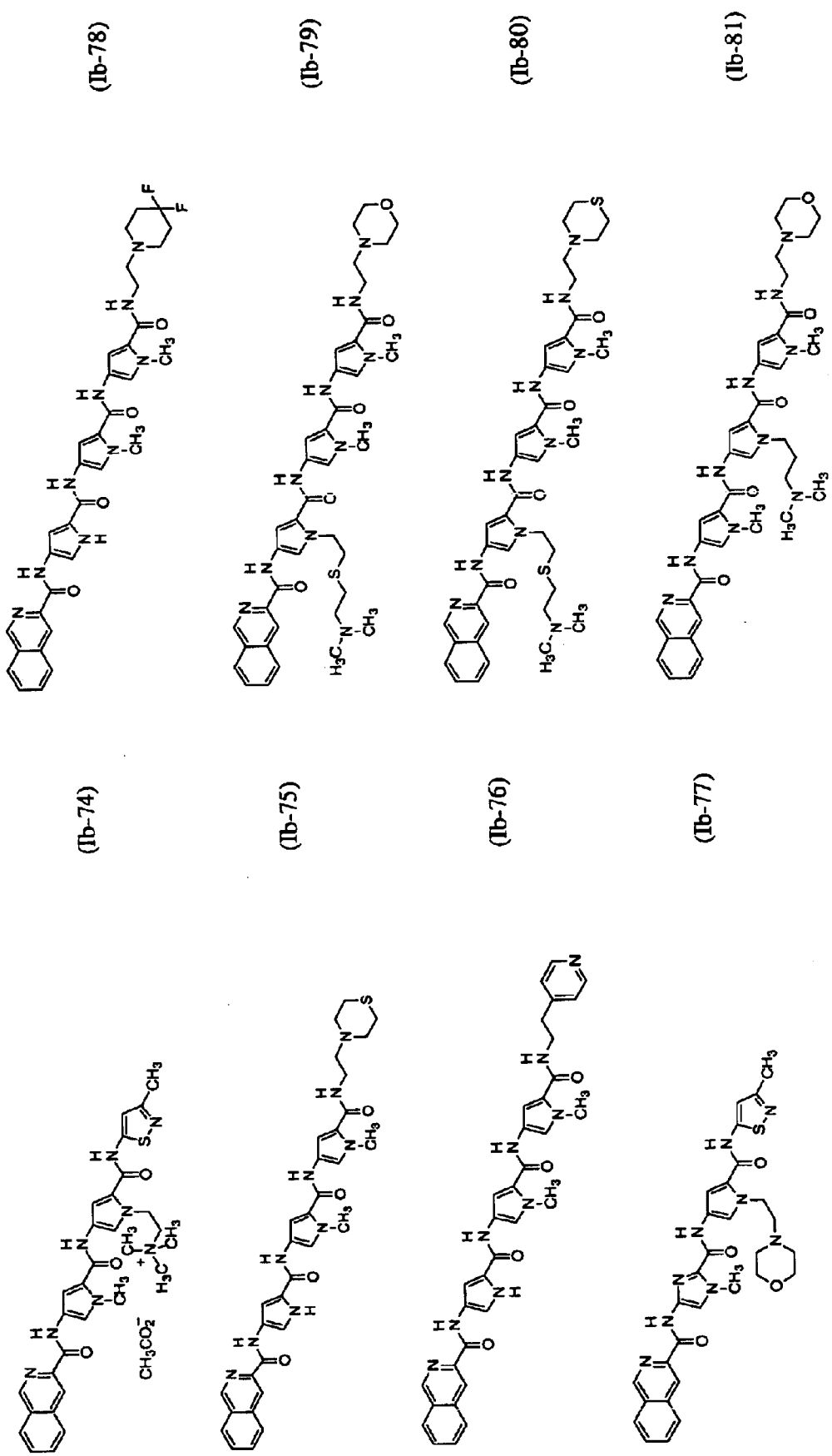
Figure 1E:
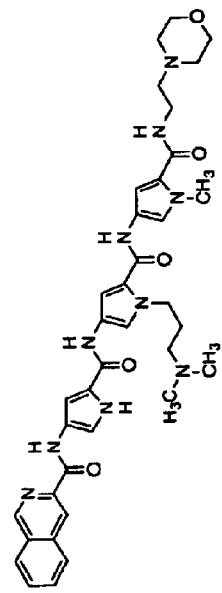
Figure 1E:
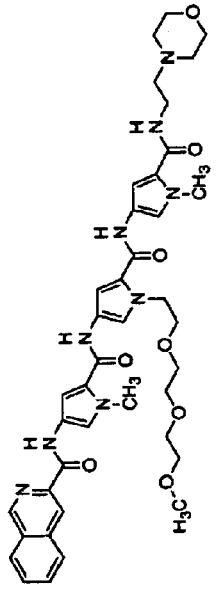
Figure 1E:
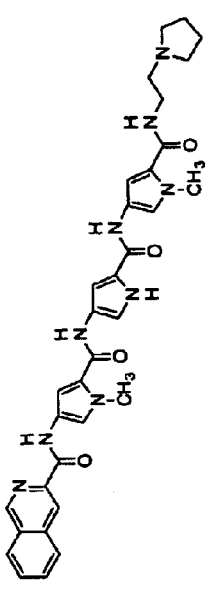
Figure 1E:
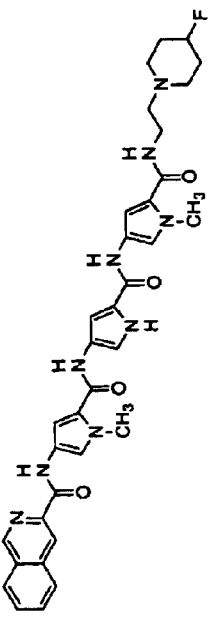
Figure 1E:
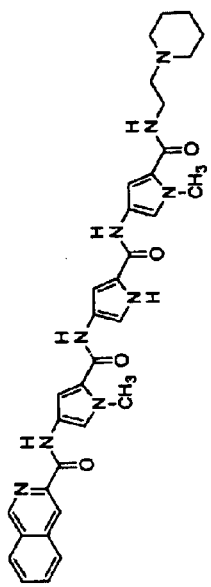
Figure 1E:
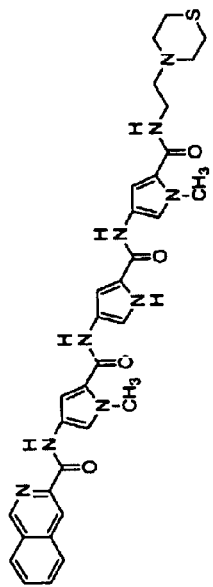
Figure 1E:
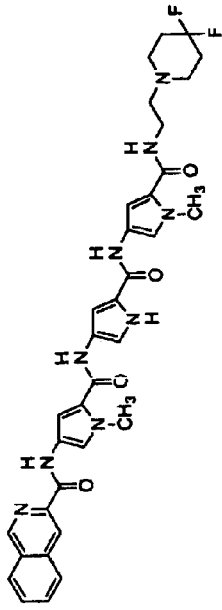
Figure 1E:
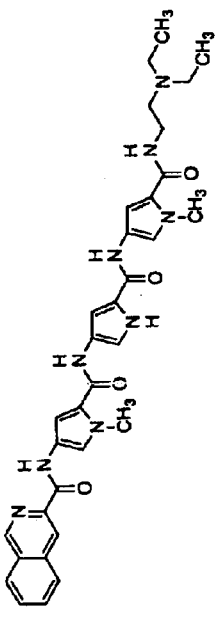
Figure 1F:
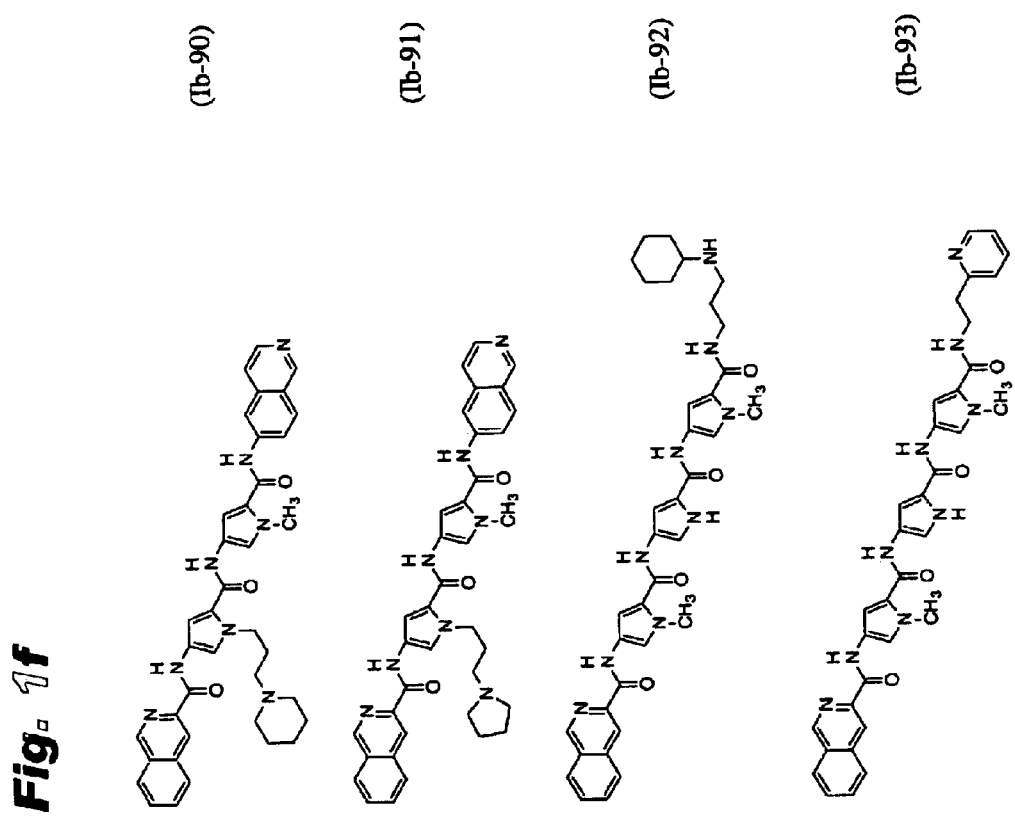

Xie et al., Synthesis and DNA Cleaving Properties of Hybrid Molecules Containing Propargylic Sulfones and Minor Groove Binding Lexitropsins, Bioorg. Med. Chem. Let., 1993, 3(8), 1565–1570.

Gupta et al., Hybrid Molecules Containing Propargylic Sulfones and DNA Minor Groove–Binding Lexitropsins: Synthesis, Sequence Specificity of Reaction with DNA and Biological Evaluation, Gene 149 (1994) 81–90.

Boger et al., Total Synthesis of Distamycin A and 2640 Analogues: A Solution–Phase Combinatorial Approach to the Discovery of New, Bioactive DNA Binding Agents and Development of a Rapid, High–Throughput Screen for Determining Relative DNA Binding Affinity or DNA Binding Sequence Selectivity, J. Am. Chem. Soc. 2000, 122, 6382–6394.

Boger et al., A Simple, High–Resolution Method for Establishing DNA Binding Affinity and Sequence Selectivity, J. Am. Chem. Soc., 2001, 123, 5878–5891.

Khalaf et al., The Synthesis of Some Head to Head Linked DNA Minor Groove Binders, Tetrahedron 56 (2000) 5225–5239.

Sen et al., "Synthesis of Compounds Related to Reserpine Skeleton," J. Indian Chem. Soc. 1969, 46(3), 209–15, Chemical Abstracts vol. 71, No. 1, (1969) p. 318.

* cited by examiner (Ib-50)
 (Ib-51)
 (Ib-52)
 (Ib-53)

(Ib-54)
 (Ib-55)
 (Ib-56)
 (Ib-57)

(Ib-82)

(Ib-83)

(Ib-84)

(Ib-85)

(Ib-86)

(Ib-87)

(Ib-88)

(Ib-89)

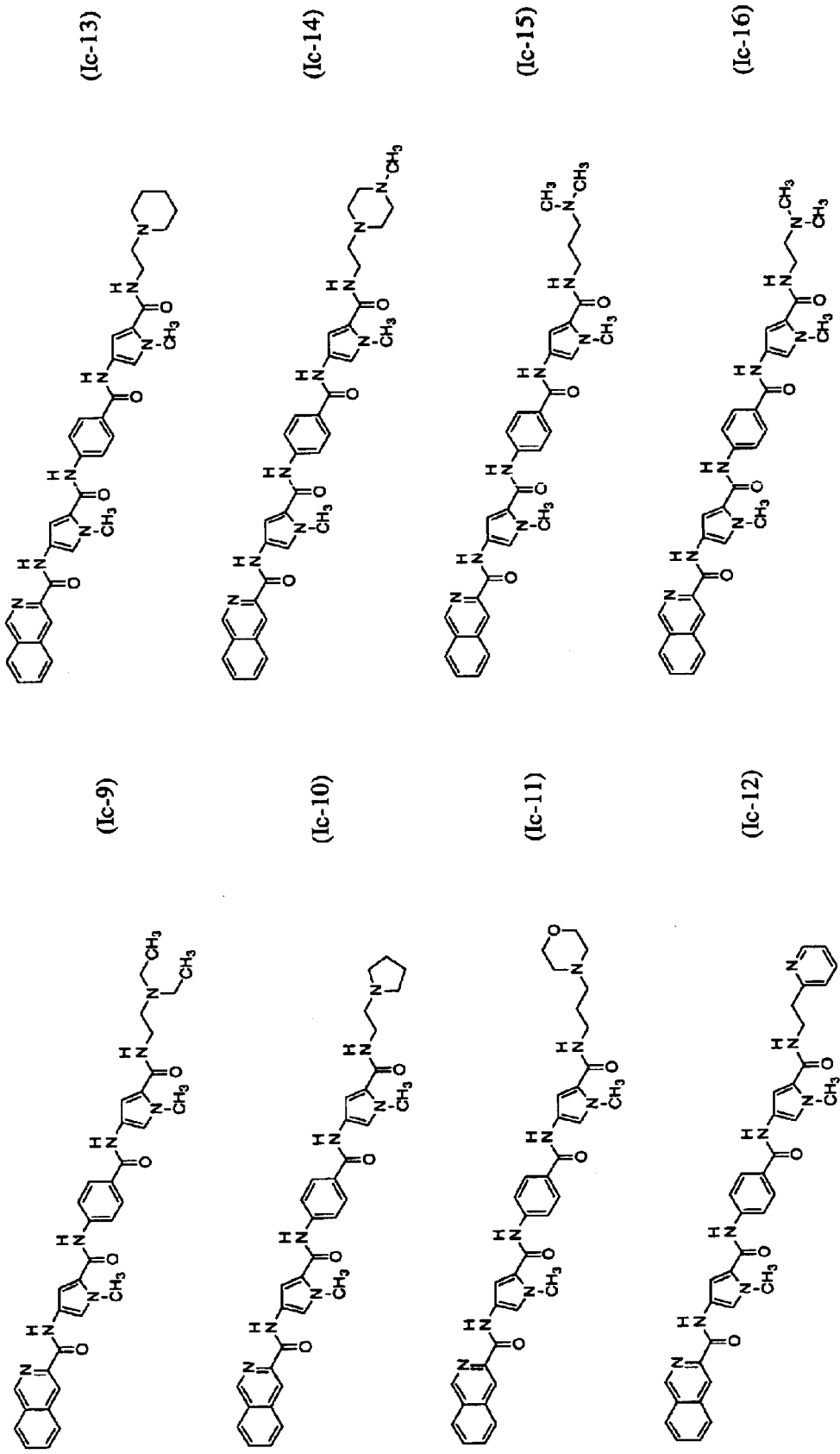

ISOQUINOLINE COMPOUNDS HAVING ANTIINFECTIVE ACTIVITY

CROSS-REFERENCE TO RELATED APPLICATIONS

This application claims the benefit of U.S. Ser. Nos. 60/333,830, filed Nov. 27, 2001, and 60/298,206, filed Jun. 13, 2001; the disclosures of which are incorporated herein by reference.

STATEMENT REGARDING FEDERALLY SPONSORED RESEARCH OR DEVELOPMENT

This invention was made with Government support under Grant No. N65236-99-1-5427 awarded by the Space and Naval Warfare Systems Command. The Government has certain rights in this invention

BACKGROUND OF THE INVENTION

1. Field of the Invention

This invention relates to isoquinoline compounds, in particular ones binding to nucleic acids and having antibacterial properties, and methods for their use.

2. Description of Related Art

A number of naturally occurring or synthetic compounds bind to double stranded nucleic acid, especially double stranded DNA ("dsDNA"). Some bind to the major groove, while others bind to the minor groove. Still others intercalate between adjacent base pairs. Combination binding modes are known, in which a compound has binding interactions with more than one nucleic acid site.

It has been proposed to use dsDNA binding compounds to regulate the expression of genes for medical purposes. If a disease is characterized by the overexpression or undesired expression of a gene (e.g., an oncogene), in principle the disease can be treated by suppressing wholly or partially the gene's expression via the binding of a compound to the gene or a promoter site thereof and interfering with transcription. Infections by pathogens such as fungi, bacteria, and viruses can be treated with compounds that interfere with the expression of genes essential for the pathogen's proliferation. Or, in a disease characterized by non- or under-expression of a beneficial gene, the expression of the beneficial gene can be up-regulated with a compound that binds to the binding site of a repressor, displacing the repressor.

The natural products distamycin and netropsin represent a class of DNA-binding compounds that has been studied over the years:

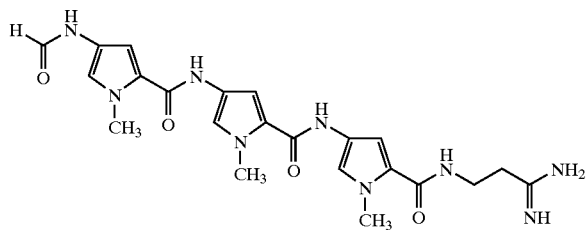

Distamycin

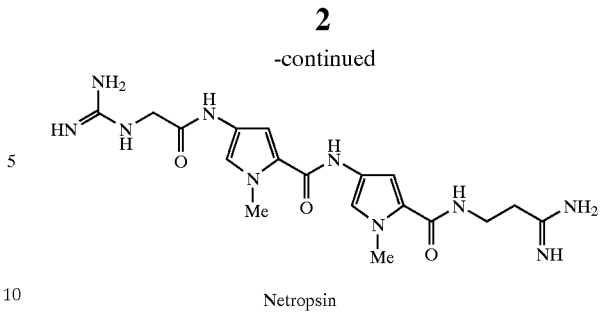

Netropsin

Structurally, distamycin and netropsin are heteroaromatic polyamides, having as their core structural motif N-methylpyrrole carboxamide residues. They bind to the minor groove, their crescent molecular shapes providing a conformational fit within the groove. The binding occurs with a preference for A,T rich dsDNA tracts.

Many heteroaromatic polyamides have been synthesized elaborating on the distamycin/netropsin motif, with the objective of enhancing or varying biological activity, increasing binding affinity to dsDNA, and/or improving specificity in base pair sequence recognition. See Bailly et al., *Bioconjugate Chemistry* 1998, 9 (5), 513–538, and Neidle, *Nat. Prod. Rep.* 2001, 18, 291–309. The use of synthetic heteroaromatic polyamides in therapeutics has been proposed, for example, in Dervan et al., U.S. Pat. No. 5,998,140 (1999); Dervan et al., WO 00/15209 (2000); Dervan, WO 00/15773 (2000); and Gottesfeld et al., WO 98/35702 (1998).

BRIEF SUMMARY OF THE INVENTION

This invention provides isoquinoline compounds having the formula

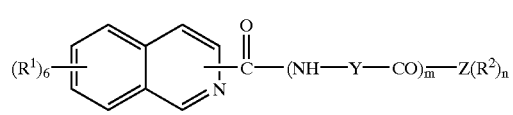

including the pharmaceutically acceptable salts thereof.

Each $R^1$ is independently H, F, Cl, Br, I, CN, OH, $NO_2$, $NH_2$, a substituted or unsubstituted ($C_1$–$C_{12}$)alkyl group, a substituted or unsubstituted ($C_1$–$C_{12}$)alkoxy group, or a substituted or unsubstituted ($C_1$–$C_{12}$)heteroalkyl group.

Each Y is independently a branched or unbranched, substituted or unsubstituted ($C_1$–$C_5$)alkylene group or a substituted or unsubstituted, aromatic or heteroaromatic ring system, wherein the ring system has a 5- or 6-member aromatic or heteroaromatic ring or fused 6,6 or 6,5 aromatic or heteroaromatic rings, with the proviso that at least one Y is a substituted or unsubstituted aromatic or heteroaromatic ring system. Preferably, at least one Y is a 5- or 6-member heteroaromatic ring. More preferably, Y in the moiety —(NH—Y—CO)— immediately adjacent to

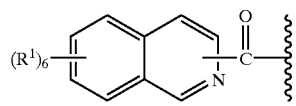

is a 5- or 6-member heteroaromatic ring.

Subscript m is an integer from 1 to 25, inclusive, preferably from 1 to 6, more preferably from 2 to 4.

Z is either O or N, with n being 1 if Z is O and 2 if Z is N.

Each $R^2$ is independently H, a substituted or unsubstituted $(C_1-C_{12})$alkyl group, or a substituted or unsubstituted $(C_1-C_{12})$heteroalkyl group.

Compound (I) has a basic group having a $pK_b$ of 12 or less or a quaternized nitrogen group.

Preferably, each moiety —(NH—Y—CO)— is independently selected from the group consisting of:

(a) moieties $M^1$ having the formula

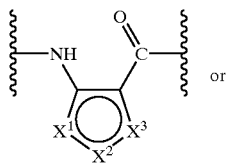
(IIa)

or

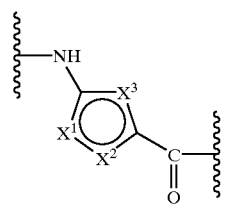
(IIb)

wherein one of $X^1$, $X^2$, and $X^3$ is a ring vertex selected from the group consisting of —O—, —S—, and —$NR^2$—, and the other two of $X^1$, $X^2$, and $X^3$ are ring vertices selected from the group consisting of =N— and =$CR^1$—;

(b) moieties $M^2$ having the formula

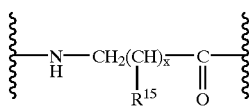
(III)

wherein x is 0 or 1 and each $R^{15}$ is independently H, OH, $NH_2$, or F;

(c) moieties $M^3$ having the formula

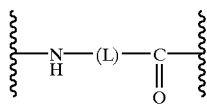
(IV)

wherein each L is independently a divalent moiety separating —NH— and —(C=O)— by 3 or 4 atoms; and (d) moieties $M^4$ having the formula

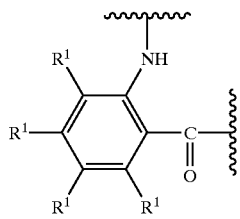
(Va)

-continued

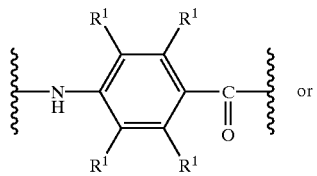
(Vb)

or

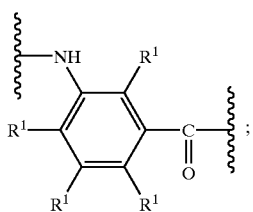
(Vc)

Preferably, at least one moiety —(NH—Y—CO)— is a moiety $M^1$. More preferably, the moiety —(NH—Y—CO)— immediately adjacent to the residue

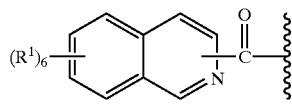

is a moiety $M^1$.

In the preceding formulae, $R^1$ and $R^2$ are as previously defined.

Preferably, $R^1$ is hydrogen, halogen (F, Cl, Br, or I), a $(C_1-C_5)$alkyl group such as methyl, ethyl, propyl, isopropyl, butyl, isobutyl, s-butyl, pentyl, and the like, a $(C_1-C_5)$ alkoxy group such as methoxy, ethoxy, propoxy, isopropoxy, butoxy, and the like, hydroxy, or cyano. Preferably, each $R^2$ is H or a $(C_1-C_5)$alkyl group such as methyl, ethyl, propyl, isopropyl, butyl, isobutyl, s-butyl, pentyl, and the like.

BRIEF DESCRIPTION OF THE DRAWING(S)

FIGS. 1a through 1f and 2a through 2c show the structures of exemplary compounds according to this invention.

DETAILED DESCRIPTION OF THE INVENTION

Abbreviations and Definitions

The term "alkyl," by itself or as part of another substituent, means, unless otherwise stated, a straight or branched chain, or cyclic hydrocarbon radical, or combination thereof, which may be fully saturated, mono- or poly-unsaturated and can include di- and multivalent radicals, having the number of carbon atoms designated (i.e. $C_1-C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having six or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo ($C_1$–$C_4$)alkyl" is meant to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, $^3$-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl, heteroalkyl, aryl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —CN and —$NO_2$ in a number ranging from zero to (2 m'+1), where m' is the total number of carbon atoms in such radical. R', R" and R'" each independently refer to hydrogen, unsubstituted ($C_1$–$C_8$)alkyl and heteroalkyl, unsubstituted aryl, aryl substituted with 1–3 halogens, unsubstituted alkyl, alkoxy or thioalkoxy groups, or aryl-($C_1$–$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g. —$CF_3$ and —$CH_2CF_3$) and acyl (e.g., —C(O)$CH_3$, —C(O)$CF_3$, —C(O)$CH_2OCH_3$, and the like). Preferably, the substituted alkyl and heteroalkyl groups have from 1 to 4 substituents, more preferably 1, 2 or 3 substituents. Exceptions are those perhalo alkyl groups (e.g., is pentafluoroethyl and the like) which are also preferred and contemplated by the present invention.

Similarly, substituents for the aryl and heteroaryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —S(O)$_2$R', —NH—C($NH_2$)=NH, —NR'C($NH_2$)=NH, —NH—C($NH_2$)=NR', —S(O)R', —S(O)$_2$NR'R", —$N_3$, —CH(Ph)$_2$, perfluoro($C_1$–$C_4$)alkoxy, and perfluoro($C_1$–$C_4$)alkyl, in a number ranging from zero to the total number of open valences on the aromatic ring system; and where R', R" and R'" are independently selected from hydrogen, ($C_1$–$C_8$)alkyl and heteroalkyl, unsubstituted aryl and heteroaryl, (unsubstituted aryl)-($C_1$–$C_4$)alkyl, and (unsubstituted aryl) oxy-($C_1$–$C_4$)alkyl.

Two of the substituents on adjacent atoms of the aryl or heteroaryl ring may optionally be replaced with a substituent of the formula —T—C(O)—$(CH_2)_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula —A—$(CH_2)_r$—B—, wherein A and B are independently —$CH_2$—, —O—, —NH—, —S—, —S(O)—, —$S(O)_2$—, —$S(O)_2NR'$— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —$(CH_2)_s$—X—$(CH_2)_t$—, where s and t are independently integers of from 0 to 3, and X is —O—, —NR'—, —S—, —S(O)—, —$S(O)_2$—, or —$S(O)_2NR'$—. The substituent R' in —NR'— and —$S(O)_2$NR'— is selected from hydrogen or unsubstituted ($C_1$–$C_6$) alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogen-carbonic, phosphoric, monohydrogenphosphoric, dihydrogenphosphoric, sulfuric, monohy-drogen-sulfuric, hydriodic, or phosphorous acids and the like, as well as the salts derived from relatively nontoxic organic acids like acetic, ascorbic, propionic, isobutyric, maleic, malonic, lactic, malic, glutamic, benzoic, succinic, suberic, fumaric, mandelic, phthalic, benzenesulfonic, p-tolylsulfonic, citric, tartaric, methanesulfonic, lactobionic, and the like. Also included are salts of amino acids such as arginate and the like, and salts of organic acids like glucuronic or galactunoric acids and the like (see, for example, Berge, S.M., et al, "Pharmaceutical Salts", *Journal of pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo enviromnent. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (chiral centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

In the discussions below, reference is made to dsDNA as the nucleic acid, but it is to be understood that the invention is not limited to dsDNA and is applicable to other nucleic acids, i.e., ribonucleic acid.

Compounds

Compounds (I) of this invention are poly- or oligoamides having an isoquinoline carboxamide unit and aliphatic, aromatic, and/or heteroaromatic carboxamide units.

Polyamides (I) are DNA-binding compounds, which bind to the minor groove of dsDNA. Different binding modes are possible. In the simplest mode, often referred to as the 1:1 binding mode, a single polyamide molecule fits in the channel formed by the minor groove. In what is referred to as the 2:1 binding mode, two polyamide molecules fit side-by-side in the minor groove, preferably aligned in an antiparallel manner (i.e., with one polyamide being aligned N-to-C and the other polyamide being aligned C-to-N, where "C" and "N" refer to the carboxy and amino termini, respectively of the polyamides). Lastly, in what is referred to as a "hairpin" binding mode, a single polyamide molecule that has a more or less centrally positioned flexible moiety (i.e., a moiety $M^3$, as discussed in greater detail hereinbelow) folds around itself to adopt a hairpin conformation when it is bound to the minor groove, so that a first portion of the polyamide at one side of the hairpin turn is adjacent to a second portion of the polyamide at the other side of the hairpin turn.

In formula (I)

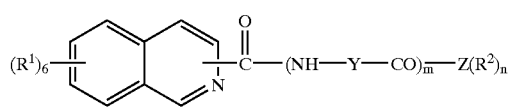

the isoquinoline group has bonded to each non-bridgehead carbon either a group $R^1$ or the group —C(=O)—(NH—Y—CO)$_m$—Z($R^2$)$_n$. Preferably, the latter group is bonded to either the isoquinoline C1 or C3. That is, the residue

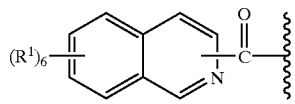

preferably is

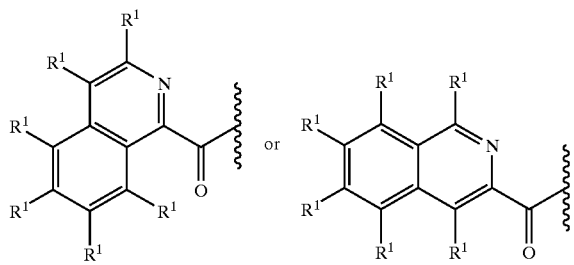

Also, two moieties $R^1$ may be connected to form a cyclic structure, a preferred example of such embodiment being:

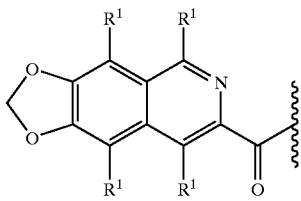

Preferably, each of the $R^1$ moieties in the immediately preceding three formulae is H.

Moieties $M^1$, described by formulae IIa and IIb

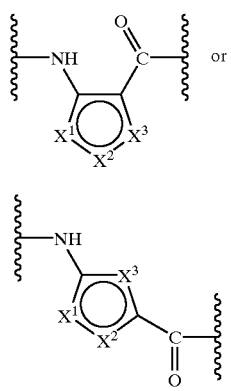

provide additional heteroaromatic polyamide building blocks. Moieties $M^1$ are 5-membered ring heteroaromatic moieties, the selection of $X^1$, $X^2$, and $X^3$ determining the type of heteroaromatic ring. Exemplary heteroaromatic rings include imidazole, pyrrole, pyrazole, furan, isothiazole, oxazole, isoxazole, thiazole, furazan, 1,2,3-thiadiazole, 1,2,4-thiadiazole, 1,2,5-thiadiazole, 1,3,4-thiadiazole, 1,2,3-triazole, 1,2,4-triazole, 1,3,4-oxadiazole, 1,2,4-oxadiazole, and thiophene. Preferably, at least one moiety Y is a moiety $M^1$.

The circle in the five-membered rings of formulae IIa and IIb is meant to indicate the presence of two double bonds, which, in some embodiments, can move within the ring.

Preferred moieties $M^1$ are IIc (hereinafter "Py"), formally derived from 1-methyl-4-aminopyrrole-2-carboxylic acid, IId (hereinafter "Hp"), formally derived from 1-methyl-3-hydroxy-4-aminopyrrole-2-carboxylic acid, and IIe (hereinafter "Im"), formally derived from 1-methyl-4-aminoimidazole-2 carboxylic acid:

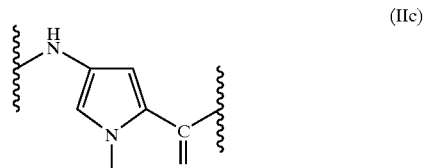

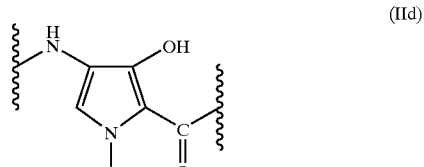

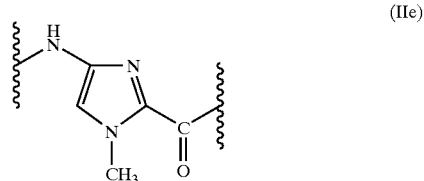

It has been shown by Dervan and co-workers (see, e.g., Dervan, U.S. Pat. No. 6,143,901 (2000); Baird et al., WO 98/37066 (1998); White et al., Nature 391, 468 (1998); White et al., Chem. Biol. 1997, 4, 569) that, in a 2:1 binding mode to dsDNA, moieties Py, Im, and Hp moieties can be used to recognize specific dsDNA base pairs, giving rise to a set of "pairing rules" correlating heteroaromatic moiety pairs and DNA base pairs. These pairing rules are summarized below:

| Heteroaromatic Pair | dsDNA Base Pair(s) Recognized |
| --- | --- |
| Im/Py | G/C |
| Py/Im | C/G |
| Py/Py | A/T, T/A (degenerate) |
| Hp/Py | T/A |
| Py/Hp | A/T |

Such recognition can lead to sequence-specific dsDNA binding, enabling the design of compounds (I) that target predetermined DNA base pair sequences, for example, a specific promoter site or a sequence characteristic of a gene.

Optionally, compound (I) can include one or more moieties $M^2$

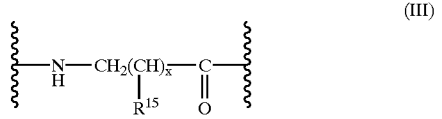

(III)

A moiety M² can function as a "spacer" for adjusting the positioning of the heteroaromatic moieties M¹ or M⁴ relative to the dsDNA base pairs at the binding site. As a compound (I) binds in the minor groove, the alignment of heteroaromatic moieties M¹ and M⁴ with the DNA base pairs with which they to interact of optimal binding or sequence recognition may drift as the number of heteroaromatic moieties M¹ and M⁴ increases. Alternatively, incorporation of a moiety M² adds flexibility to compound (I), allowing its curvature to more accurately match that of the minor groove. The incorporation of one or more flexible moieties M² relaxes the curvature of the compound backbone, permitting larger compounds (I) to bind to longer sequences of DNA. In some preferred embodiments a moiety M² is present for every 4 to 5 heteroaromatic moieties M¹ or M⁴, more preferably interrupting long sequences of M¹ and/or M⁴ groups.

Preferred moieties M² are those corresponding to glycine (x=0 in formula III, depicted as IIIa below) and β-alanine (n=1 and R¹⁵=H in formula III; depicted as IIIb below, hereinafter "β"), with the latter being especially preferred.

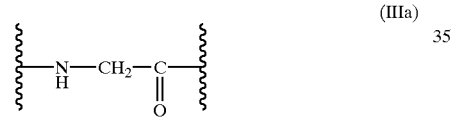

(IIIa)

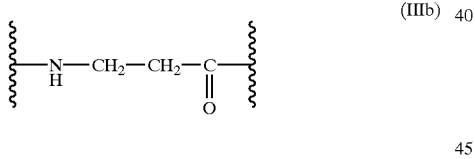

(IIIb)

Moieties M² in which x=1 and R¹⁵=OH, NH₂, or F can be used to alter the binding affinity and specificity (relative to β-alanine), as disclosed in Floreancig et al., *J. Am. Chem. Soc.*, 2000, 122, 6342; the disclosure of which is incorporated herein by reference.

When present in compound (I), optional moieties M³ (formula IV)

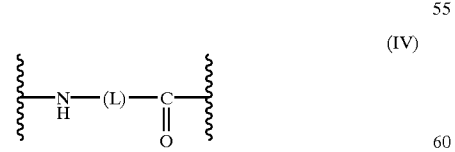

(IV)

have a group L providing a spacer of 3 to 4 atoms between —NH— and —C(═O)— and can be used to introduce a hairpin turn into compound (I). See Mrksich et al., *J. Am. Chem. Soc.* 1994, 116, 7983. Exemplary moieties M³ include:

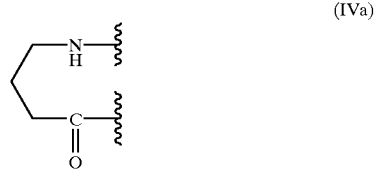

(IVa)

(IVb)

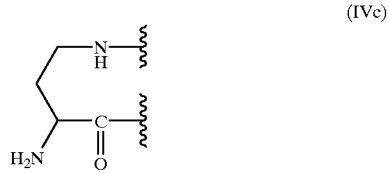

(IVc)

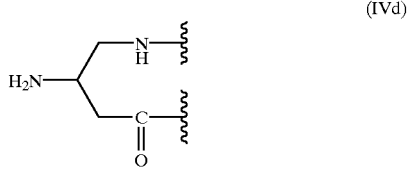

(IVd)

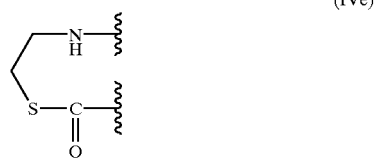

(IVe)

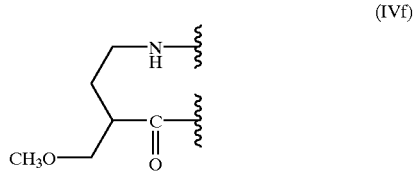

(IVf)

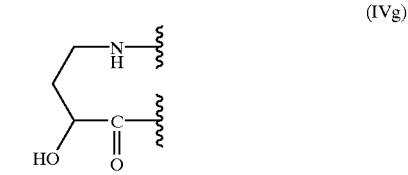

(IVg)

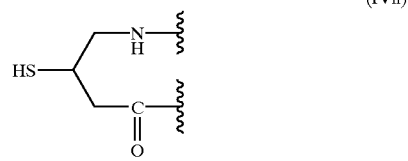

(IVh)

(IVi)

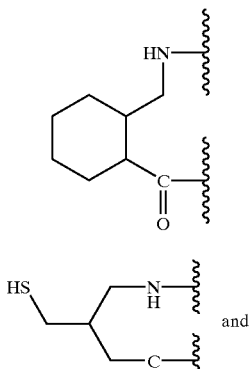

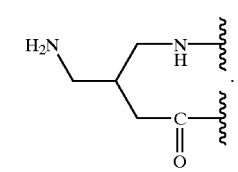 and

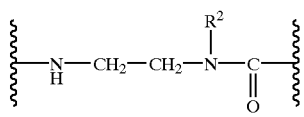

Moieties IVa (hereinafter "γ"), corresponding to γ-aminobutyric acid, and IVc, corresponding to 2,4-diaminobutyric acid, are preferred. Selecting one enantiomer or the other of moieties $M^3$ that are chiral allows stereochemical control of the binding of polyamides to the minor groove, for example as disclosed in Baird et al., WO 98/45284 (1998) in respect of R-2,4-diaminobutyric acid and S-2,4-diaminobutyric acid (corresponding to R-IVc and S-IVc, respectively).

Yet another class of moieties $M^3$ is represented by the formula

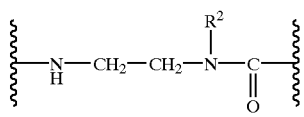

where $R^2$ is as previously defined.

While the group L preferably provides a 3-atom separation between the —NH— and the —(C=O)—, a 4-atom separation is also permissible, as illustrated by a 5-aminovaleric acid residue (i.e., L equals —(CH$_2$)$_4$—):

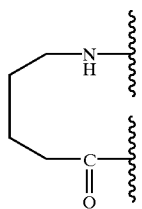

L can have pendant groups, which serve to enhance solubility or function as attachment points for other groups (e.g., IVc, IVd, IVg, IVh, IVk, IVl). The 3 to 4 atoms can be part of a larger group, which provides conformational rigidity (e.g., IVj). The 3 to 4 atoms can comprise carbon atoms only or it can include heteroatoms (e.g., IVb, IVe, IVi).

Moieties $M^4$ are used to introduce a benzamide unit into compound (I). Preferably, the benzamide unit is para-oriented, as in

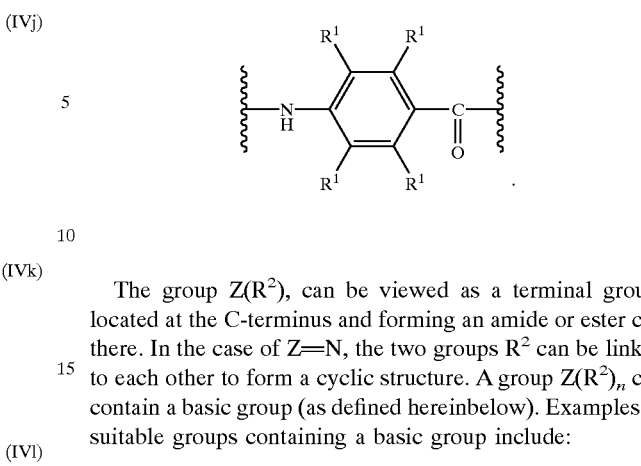

The group $Z(R^2)$, can be viewed as a terminal group, located at the C-terminus and forming an amide or ester cap there. In the case of Z=N, the two groups $R^2$ can be linked to each other to form a cyclic structure. A group $Z(R^2)_n$ can contain a basic group (as defined hereinbelow). Examples of suitable groups containing a basic group include:

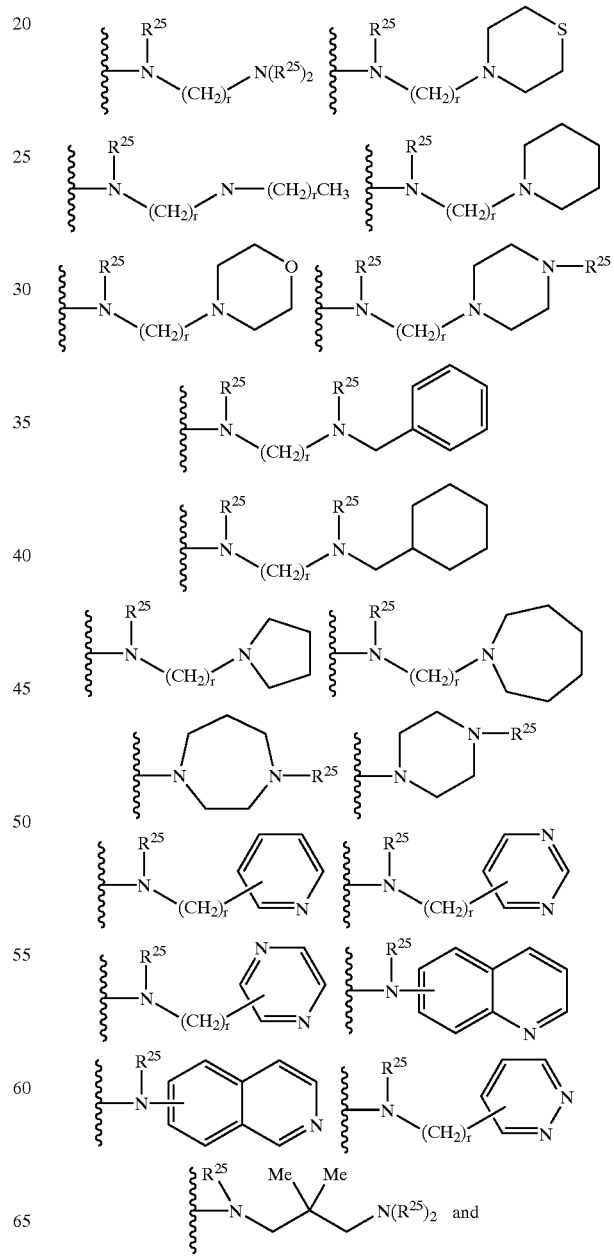

-continued

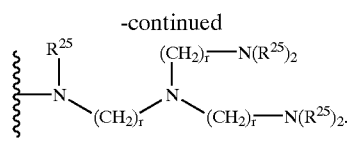

Examples of suitable groups $Z(R^2)_n$ not containing a basic group include:

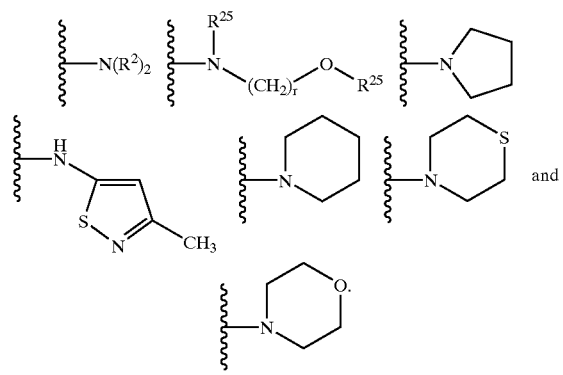

and

In the foregoing formulae, r is an integer ranging from 2 to 8, inclusive (preferably 2 to 6), and each $R^{25}$ is independently H, $CH_3$, $CH_2CH_3$, $CH_2CH_2CH_3$, or $CH(CH_3)_2$, The classification of the 5-amino-2-methylisothiazole group as a "nonbasic" $Z(R^2)_n$ group is somewhat arbitrary, as its $pK_b$ is marginal, normally around 12–13 (i.e., $pK_a$ 1–2) and depending on the molecular structure of the entire compound, it may qualify or not as a basic group as such is defined herein. Preferably, where a 5-amino-2-methylisothiazole is present, the compound has a basic group elsewhere in the molecule, for example pendant from a moiety $M^1$ or $M^4$, as exemplified by compounds Ib-39 and Ib-40, infra.

The preceding illustrative formulae of basic and nonbasic groups $Z(R^2)_n$ have been drawn with Z as N and n as 2 for convenience. Those skilled in the art will appreciate that in these formulae the residue $NR^{25}$ can be replaced with O to give the corresponding groups $Z(R^2)_n$ in which Z is O and n is 1. Where Z is O, preferably the adjacent moiety Y is Py.

As used herein with reference to groups $R^1$ and $R^2$, "substituted or unsubstituted ($C_1$–$C_{12}$)alkyl group, or a substituted or unsubstituted ($C_1$–$C_{12}$)heteroalkyl group" includes not only conventional alkyl or cycloalkyl groups such as methyl, ethyl, propyl, isopropyl, butyl, s-butyl, isobutyl, t-butyl, cyclopentyl, cyclohexyl, and pentyl, but also unsaturated $C_1$ to $C_{12}$ groups, having for example aromatic, alkenyl, or alkynyl groups (e.g., phenyl, benzyl, vinyl, cyclohexenyl, etc.). One or more backbone carbons can be replaced by heteroatoms. There may be present functionalities such as hydroxy; oxo (=O); primary, secondary, or tertiary amine (e.g., $-NH_2$, $-NH(CH_3)$, $-N(CH_3)_2$); quaternary ammonium (e.g., $-N(CH_3)_3^+$); alkoxy (e.g., methoxy, ethoxy); acyl (e.g., $-C(=O)CH_3$); amide (e.g., $-NHC(=O)CH_3$); thiol; thioether (e.g., $-SCH_3$); sulfoxide; sulfonamide (e.g., $-SO_2NHCH_3$); halogen (e.g., F, Cl); nitro; and the like. Exemplary specific $R^1$ and $R^2$ groups include methyl, trifluoromethyl, ethyl, acetyl, methoxy, methoxyethyl, ethoxyethyl, aminoethyl, hydroxyethyl, propyl, hydroxypropyl, cyclopropyl, isopropyl, 3-(dimethylamino)propyl, butyl, s-butyl, isobutyl, t-butyl, pentyl, cyclopentyl, vinyl, allyl, ethynyl, propynyl, and the like.

Compound (I) has a basic group having a $pK_b$ of 12 or less or a quaternized nitrogen group. (Or, stated conversely, the conjugate acid of the basic group has a $pK_a$ greater than 2 ($pK_a=14-pK_b$).) Preferably, the $pK_b$ is less than 10, more preferably less than 5. A $pK_b$ of less than 12 ensures that compound (I) is protonated under the conditions in which it interacts with a nucleic acid. Preferably the basic group is a nitrogenous group, for example an amine, an amidine, a guanidine, a pyridine, a pyridazine, a pyrazine, a pyrimidine, an imidazole, or an aniline. Primary, secondary, or tertiary aliphatic amines, are preferred. Exemplary quatemized nitrogen groups include alkyl pyridinium and tetraalkyl ammonium groups such as:

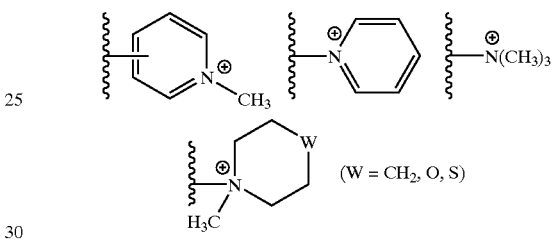

(W = $CH_2$, O, S)

A basic/quatemized nitrogen group may improve cell transport properties, enabling the compounds of this invention to be transported across cellular and nuclear membranes and to reach dsDNA in the nucleus. See Rothbard et al., WO 98/52614 (1998), which discloses that guanidine or amidino side chain moieties enhance transport across biological membranes. Another possible benefit is enhancement of the binding affinity to the nucleic acid, perhaps via ionic interactions with backbone phosphate groups. See Baird and Dervan, WO 98/37087 (1998) and Bruice et al., U.S. Pat. No. 5,698,674 (1997). Lastly, the protonated basic or quatemized nitrogen group enhances the solubility of compounds (I).

Preferably, the basic or quatemized nitrogen group is present within the C-terminal group $Z(R^2)_n$, but it may be present elsewhere in the molecule, for example as part of a group $R^1$ or $R^2$ in $M^1$ or $M^4$. Or, multiple basic or quatemized nitrogen groups may be present, at different locations on compound (I).

In a preferred embodiment, compound (I) is according to formula (Ia):

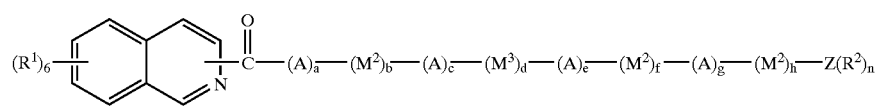

(Ia)

wherein $M^2$, $M^3$, $R^1$, $R^2$, Z and n have the same meanings as previously assigned; each A is independently $M^1$ or $M^4$; each of a, c, e, g and h is an integer independently from 0 to 5, inclusive; and each of b, d, and f is independently 0 or 1. The sum of a, c, e, and g is preferably at least 2, more preferably at least 3.

In another preferred embodiment, compound (I) is according to formula (Ib):

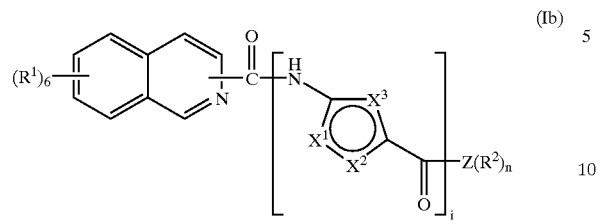

wherein $X^1$, $X^2$, $X^3$, $R^1$, $R^2$, Z, and n have the meanings previously assigned and i is an integer between 2 and 4, inclusive. In one subset of compounds according to formula (Ib), each of the moieties

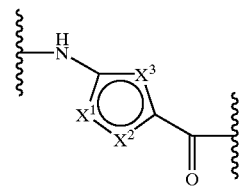

is Py, as exemplified by the compounds in Table A:

TABLE A

Illustrative Compounds (Ib)

| Compound Ref. | (R¹)₆—[isoquinoline-C(=O)—]ᵢ | i | —Z(R²)ₙ |
|---|---|---|---|
| Ib-1 | isoquinolin-1-yl-C(=O)- | 3 | —NH-CH₂CH₂-morpholine |
| Ib-2 | isoquinolin-3-yl-C(=O)- | 3 | Same |
| Ib-3 | Same | 3 | —NH-CH₂CH₂-thiomorpholine |
| Ib-4 | Same | 3 | —NH-CH₂CH₂-piperidine |
| Ib-5 | Same | 3 | —NH-CH₂CH₂-pyrrolidine |
| Ib-6 | Same | 3 | —NH-CH₂CH₂-(2,6-dimethylmorpholine) |
| Ib-7 | Same | 3 | —O-CH₂CH₂-morpholine |

TABLE A-continued

Illustrative Compounds (Ib)

| Compound Ref. | (R¹)₆—[isoquinoline]—C(O)— | i | —Z(R²)ₙ |
|---|---|---|---|
| Ib-8 | Same | 4 | —NH—CH₂CH₂—N(morpholine) |
| Ib-9 | Same | 3 | —NH—CH₂—C(Me)₂—CH₂—N(Me)—N(Me)₂ |
| Ib-10 | Same | 3 | —NH—CH₂CH₂CH₂—N(morpholine) |
| Ib-11 | Same | 2 | —NH—CH₂CH₂—N(2,6-dimethylmorpholine) |
| Ib-12 | Same | 3 | —NH—CH₂CH₂—NH—cyclohexyl |
| Ib-13 | Same | 2 | —NH—CH₂CH₂—N(thiomorpholine) |
| Ib-14 | isoquinoline-3-carbonyl | 2 | —NH—CH₂CH₂—N(pyrrolidine) |
| Ib-15 | Same | 2 | —NH—CH₂CH₂—N(piperidine) |
| Ib-16 | Same | 3 | —NH—CH₂CH₂—NH—(pyrimidin-2-yl) |

TABLE A-continued

Illustrative Compounds (Ib)

| Compound Ref. | (R¹)₆-[isoquinoline]-C(O)-N | i | -Z(R²)ₙ |
|---|---|---|---|
| Ib-17 | Same | 3 | ⁓NH-CH₂CH₂-N(2,6-dimethylpiperidin-1-yl) |
| Ib-18 | Same | 3 | ⁓NH-CH₂CH₂-(pyridin-2-yl) |
| Ib-19 | Same | 3 | ⁓NH-CH₂CH₂-(pyridin-3-yl) |
| Ib-20 | Same | 3 | ⁓NH-CH₂CH₂-(1-methylpyrrolidin-2-yl) |
| Ib-21 | Same | 3 | ⁓NH-CH₂CH₂-(azepan-1-yl) |
| Ib-22 | Same | 3 | ⁓NH-CH₂CH₂-(4-hydroxypiperidin-1-yl) |
| Ib-23 | Same | 3 | ⁓NH-CH₂CH₂-NH-C(=NH)-NH₂ |
| Ib-24 | Same | 3 | ⁓NH-CH₂CH₂-(4-fluoropiperidin-1-yl) |
| Ib-25 | Same | 4 | ⁓NH-CH₂CH₂CH₂-N(CH₃)₂ |
| Ib-26 | Same | 4 | ⁓NH-CH₂CH₂-(pyrrolidin-1-yl) |

TABLE A-continued
Illustrative Compounds (Ib)
| Compound Ref. | (R¹)₆ [isoquinoline-C(O)-N] | i | Z(R²)ₙ |
|---|---|---|---|
| Ib-27 | 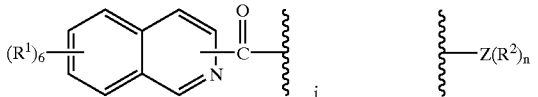 | 4 | 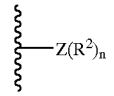 |
| Ib-28 | Same | 4 | 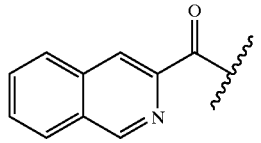 |
| Ib-29 | Same | 4 | 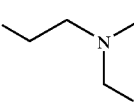 |
| Ib-30 | Same | 4 | 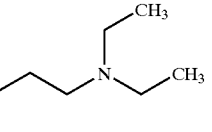 |
| Ib-31 | Same | 4 | 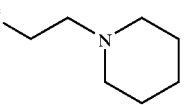 |
| Ib-32 | Same | 4 | 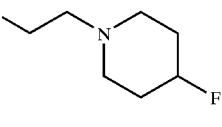 |
| Ib-33 | Same | 4 | 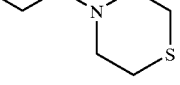 |
| Ib-34 | Same | 3 | 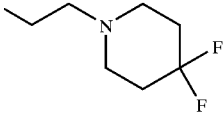 |
| Ib-35 | Same | 3 | 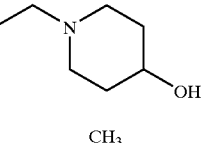 |
| Ib-36 | Same | 3 | 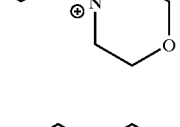 |

TABLE A-continued

Illustrative Compounds (Ib)

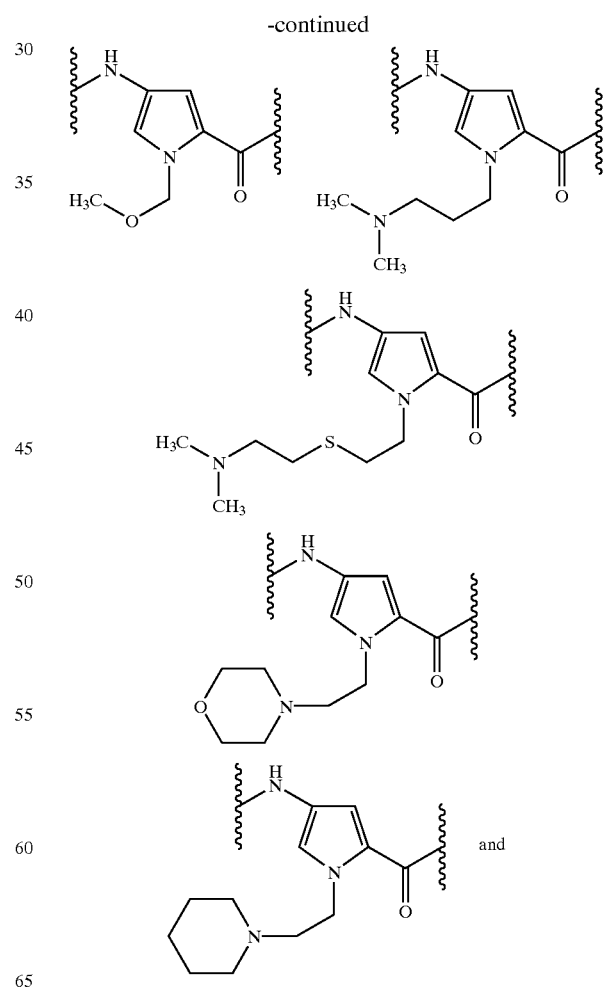

However, the moieties

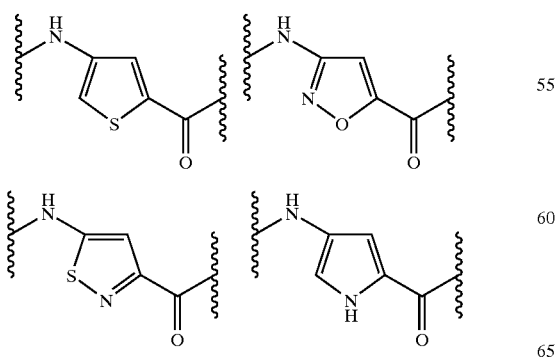

need not all be Py. They can be other 5-member ring heterocycles, as illustrated by compounds Ib-50 through Ib-93 shown in FIGS. 1a through 1f. As illustrated by compounds such as Ib-55 to Ib-57, Ib-63 to Ib-66, Ib-68, and Ib-73 to Ib-74, compounds Ib can have basic or quaternized nitrogen groups pendant from a 5-member heterocycle, instead or in addition to a basic/quaternized nitrogen group in the C-terminal $Z(R^2)_n$. Preferred non-Py 5-member ring heterocycles are selected from the group consisting of

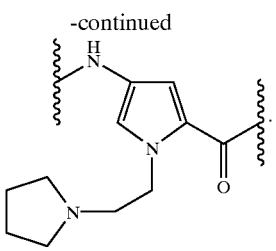

In yet another preferred embodiment, compounds (I) of this invention are according to formula (Ic):

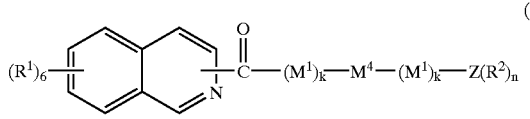

wherein $M^4$, $R^1$, $R^2$, Z, and n are as previously defined and each k is independently an integer from 0 to 4, inclusive. A preferred subclass of compounds (Ic) is of the formula

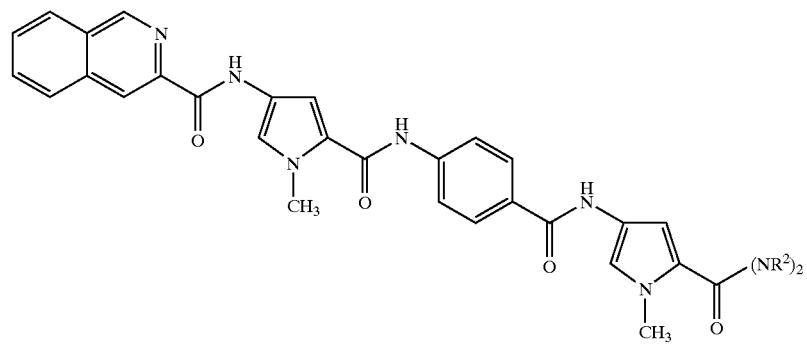

Figure 2A:
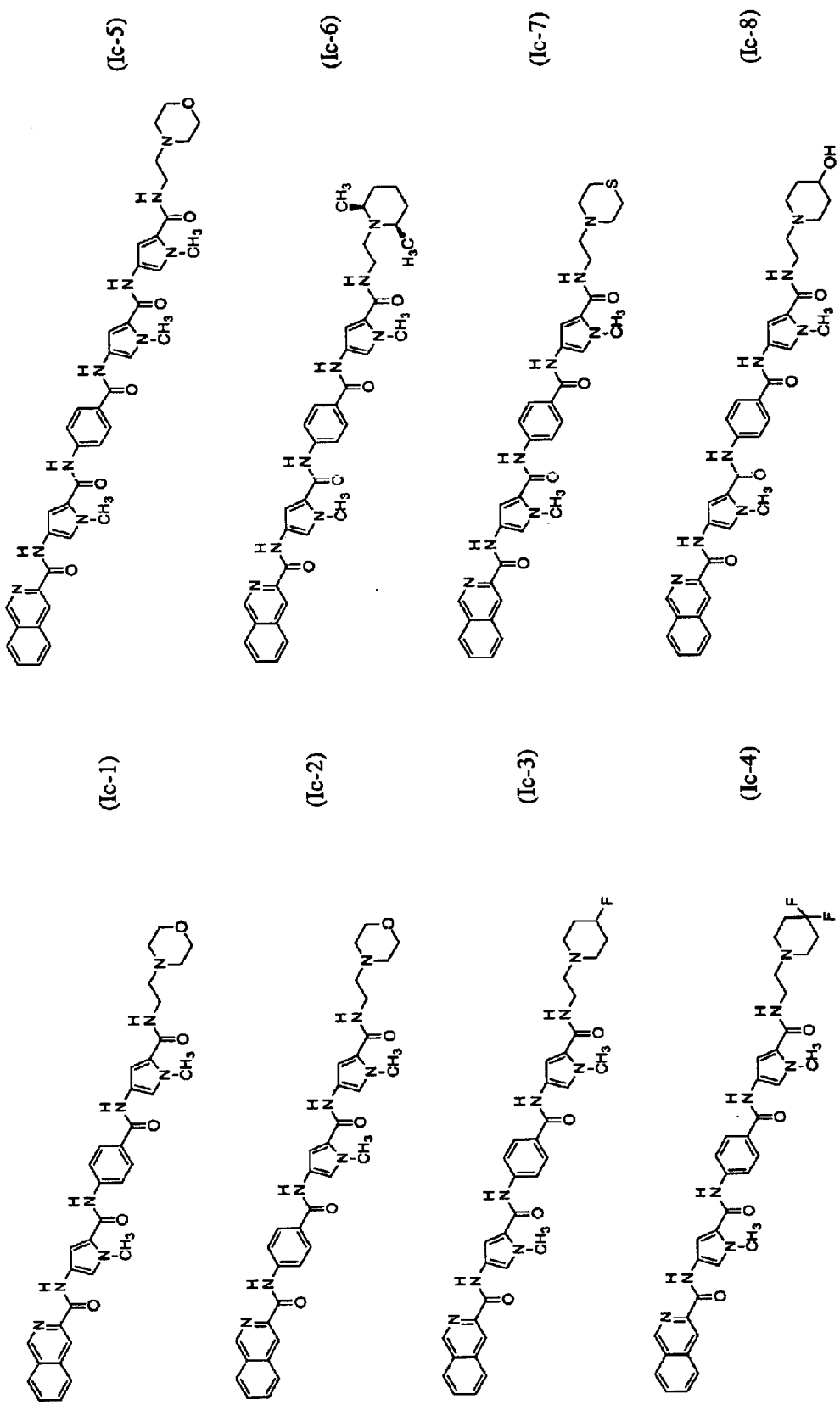
Figure 2C:
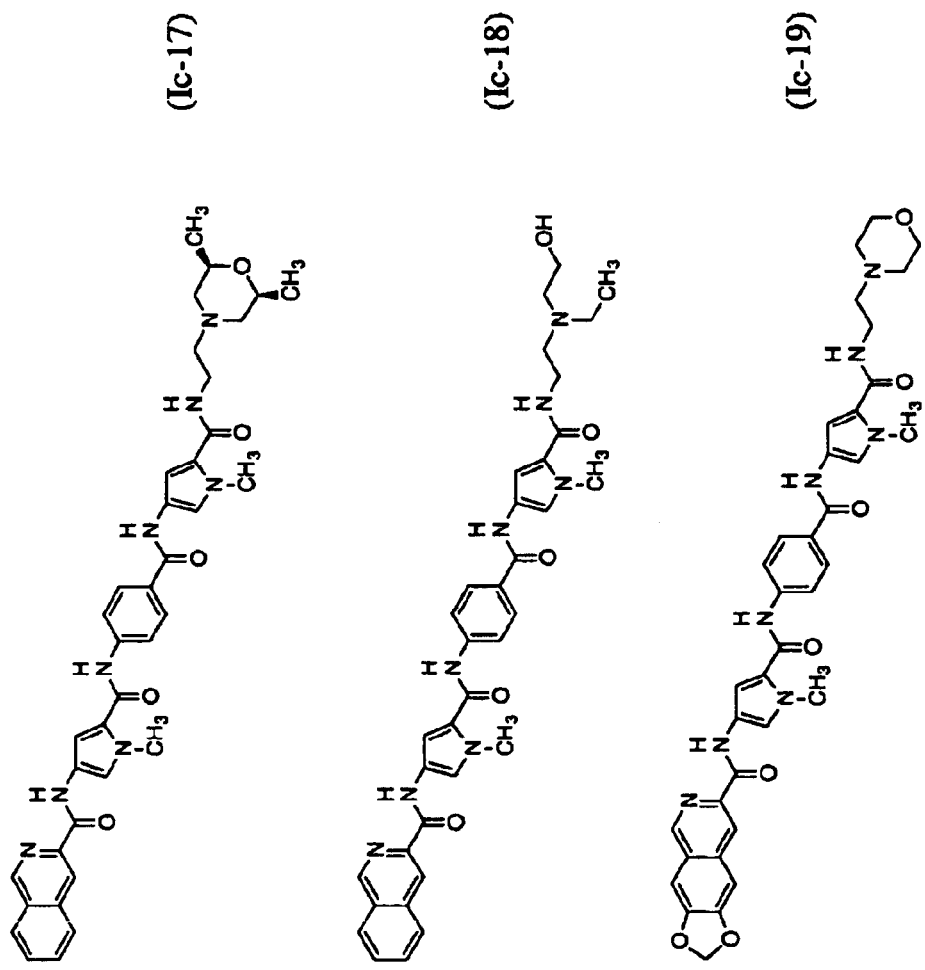

Illustrative compounds (Ic) are shown in FIGS. 2a through 2c.

Compounds of formula (I) can have a 6,5-condensed heteroaromatic ring system, either individually or linked to another aromatic or heteroaromatic ring system, as illustrated by compound Id-1.

(Id-1)

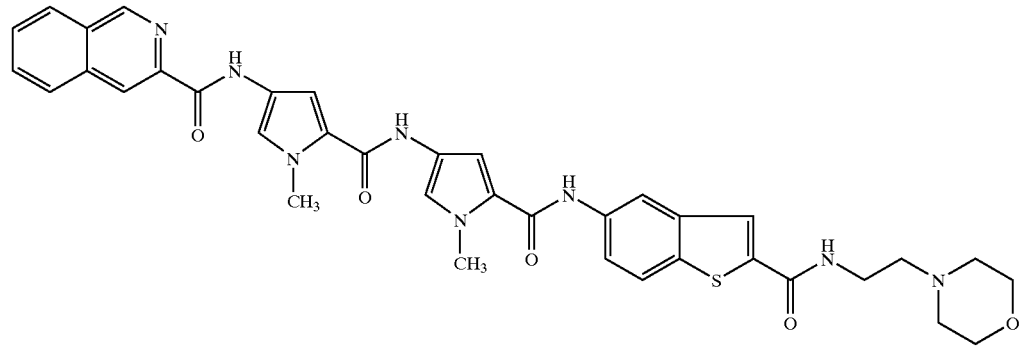

Compounds (I) can be conjugated or linked to another nucleic acid binding compound. The conjugated nucleic acid binding compounds can be two identical or different compounds (I), or one compound (I) and a different class of nucleic acid binder, for example an intercalator, a triple helix former, a binder to the phosphate backbone, a major groove binder, another type of minor groove binder, and the like. A preferred site for forming the conjugating link is an amino, hydroxy, or thiol functionality in a group L in moiety $M^2$, which can be acylated or alkylated. The preparation of tandem linked nucleic acid binding polyamides in this manner is disclosed in Baird et al., WO 98/45284 (1998), the disclosure of which is incorporated herein by reference.

Compounds (I) also can be conjugated to other moieties, such as, peptides, proteins, transport agents, fluorophores or other reporter groups, and the like.

Compounds (I) preferably bind to dsDNA with high affinity, meaning an equilibrium association constant of at least $10^3$ $M^{-1}$, more preferably at least $10^6$ $M^{-1}$, and most preferably at least $10^9$ $M^{-1}$. The measurement of binding affinities by quantitative DNase I footprinting is disclosed in Dervan, WO 98/50582 (1998), and Trauger et al., Nature 382, 559 (Aug. 8, 1996); the disclosures of which are incorporated herein by reference.

Compounds of this invention can be used to form complexes with dsDNA, for the purpose of recognizing and/or isolating dsDNA strands containing particular base-pair sequences, for example for analytical or diagnostic purposes. Thus, in another aspect of this invention there is provided a complex between dsDNA and compound of this invention. In cellular systems or in living organisms, they can modulate the expression of a gene by binding to the gene or a promoter or repressor region thereof. Such modulation may be useful for therapeutic or research purposes.

Additionally, compounds of this invention have been found to have anti-bacterial and/or antifungal properties and therefore may be used for combating (i.e., preventing and/or treating) infections in eukaryotic organisms. Other pathogens against which compounds of this invention can be useful include protozoa and viruses. For human anti-infective applications, an effective amount of a compound of this invention is used, optionally in combination with a pharmaceutically acceptable carrier. The composition may be dry, or it may be a solution. Treatment may be reactive, for combating an existing infection, or prophylactic, for preventing infection in an organism susceptible to infection. Preferably, compounds of this invention are used to treat infections by drug-resistant strains of bacteria, for example MRSA (methycillin resistant S. aureus), MRSE (methycillin resistant S. epidermidis), PRSP (penicillin resistant S. pneumoniae) or VRE (vancomycin resistant Enterococci). By "drug-resistant" it is meant that the bacteria are resistant to treatment with conventional antibiotics.

Host organisms that can be treated include eukaryotic organisms, in particular plants and animals. The plant may be an agriculturally important crop, such as wheat, rice, corn, soybean, sorghum, and alfalfa. Animals of interest include mammals such as bovines, canines, equines, felines, ovines, porcines, and primates (including humans). Thusly, in another aspect of this invention, there is provided a method for treating a bacterial infection—particularly an infection by Gram-positive bacteria—comprising administering to a patient in need of such treatment an effective amount of compound (I). Compounds of this invention can be used in the preparation of a medicament for treating a bacterial infection in a mammal. The compounds may be administered orally, topically, or parenterally (e.g., intravenously, subcutaneously, intraperitoneally, transdermally).

While not wishing to be bound by any particular theory, it is believed that the compounds of this invention derive their biological activity from their ability to bind to dsDNA.

Compounds I can be synthesized by solid phase techniques from the corresponding amino acids or their derivatives, for instance IIc', IId', and IIe' for the synthesis of the Py, Hp, and Im building blocks, respectively.

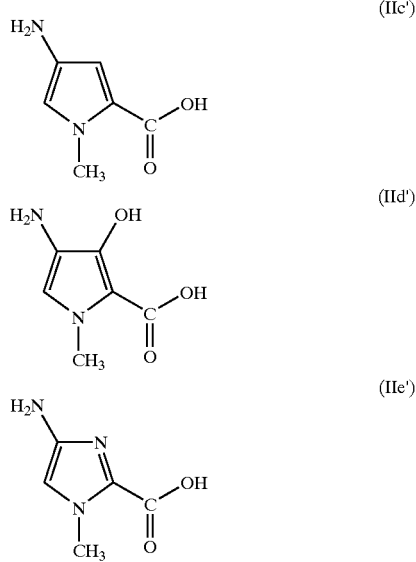

In solid phase synthesis, a polyamide is synthesized on a resin such as Boc-glycine-PAM-resin or Boc-β-alanine-PAM-resin, with moieties Y being added in series of steps involving amino-protected and carboxy-activated monomers, as taught in Dervan et al., U.S. Pat. No. 6,090, 947 (2000) (the "'947 patent"); Baird et al., WO 98/37066 (1998); Baird et al., WO 98/37067 (1998); and Dervan et al., WO 98/49142 (1998); Baird et al., U.S. application Ser. No. 10/132,887, filed Apr. 24, 2002; McMinn, U.S. Provisional Application Ser. No. 60/298,206, filed Jun. 13, 2001 (the "'206 application"); Ge et al., WO 01/74898 (2001) (the "'898 application"); Kelly et al., Proc. Natl. Acad. Sci. USA, July 1996, 93, 6981 ("Kelly"); and Wade et al., J. Am. Chem. Soc., 1992, 114, 8783 ("Wade"); the disclosures of which are incorporated herein by reference.

The practice of this invention may be further understood by reference to the following examples, which are provided by way of illustration and not of limitation.

Synthesis of Compounds

General

Typically, the structures of compounds were confirmed by $^1$H-NMR and/or mass spectrometry. Where a parenthetical remark such as "$^1$H-NMR" or "mass spectrum" follows a reference to a compound without any elaboration, it means that such spectrum was taken, was consistent with the assigned structure, and did not indicate the presence of significant impurities.

Abbreviations in common usage are employed for various solvents, catalysts and reagents, including: HBTU for 2-(1H-benzotriazole-1-yl)-1,1,3,3-tetramethyluronium hexa-for dicyclohexyl-carbodiimide; BOPCl for bis(2-oxo-3-oxa-zolidinyl)-phosphinic chloride; HATU for O-(7-azabenzotriazol-1-yl)-N,N,N',N'-tetramethyluronium hexa-fluorophosphate; and MOMCl for methoxymethyl chloride.

The skilled artisan will understand: (a) that an intermediate described in the context of the synthesis of a particular compound of this invention can also be used to make other compounds of this invention, mutatis mutandis; (b) that in certain experimental sections only the preparation of an intermediate compound is described, because its incorporation into a final compound of this invention straightforwardly follows synthetic methodology described herein; and (c) that, for some routine reactions (HBTU-mediated couplings, hydrogenations, saponifications, etc.) that recur herein, detailed reaction and work-up conditions sometimes are not provided after the first few recurrences in the interest of brevity and that the conditions described elsewhere in this application are adaptable to the instance at hand without undue experimentation.

EXAMPLE A

Scheme A-1 describes the synthesis of intermediates containing an isoquinoline carboxamide moiety having adjacent thereto one to four N-methylpyrrole carboxamide ("Py") units. The syntheses of acids 19 and 21 are described in detail; acids 18 and 20 can be made by analogy. The preparations of compounds Ib-5, Ib-24 and Ib-31 are given as representative examples.

Scheme A-1

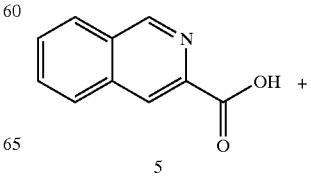

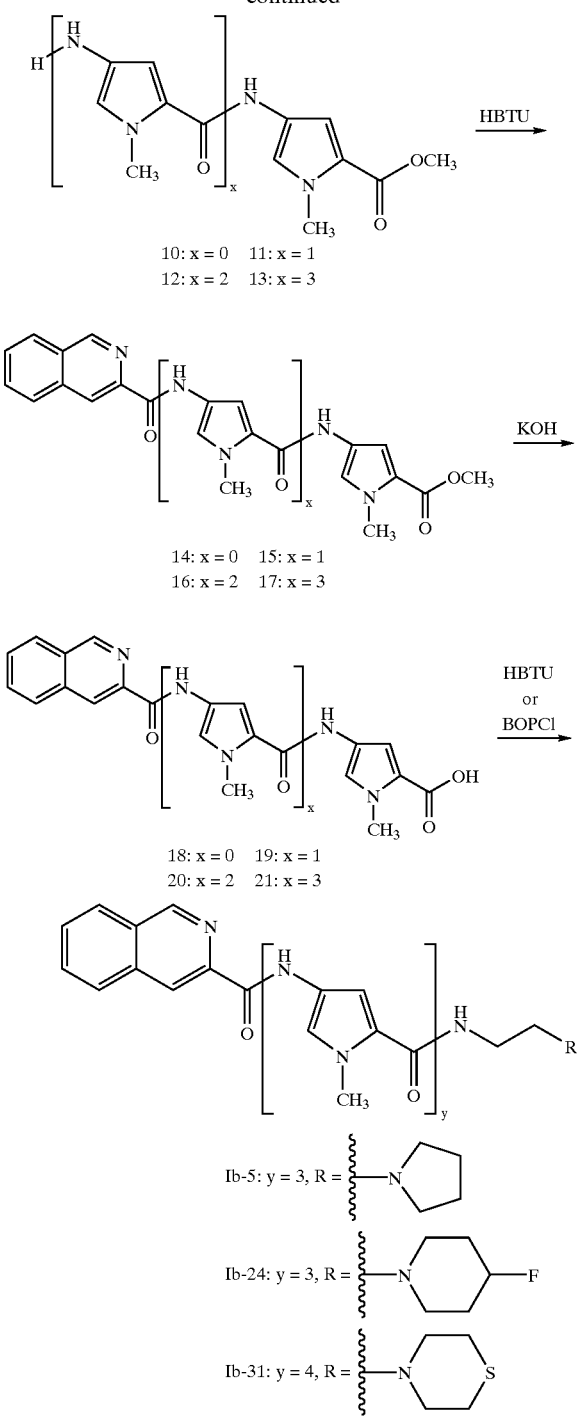

10: x = 0   11: x = 1
12: x = 2   13: x = 3

14: x = 0   15: x = 1
16: x = 2   17: x = 3

18: x = 0   19: x = 1
20: x = 2   21: x = 3

Ib-5: y = 3, R = pyrrolidinyl

Ib-24: y = 3, R = 4-fluoropiperidinyl

Ib-31: y = 4, R = thiomorpholinyl

Starting materials. Starting materials 10–13 are known compounds (CAS Reg. Nos. 180258-45-1, 126092-99-7, 162085-96-3, and 295805-47-9, respectively). Tetrame 13 was prepared by coupling Boc-protected acid 30 and ester 11 with HBTU followed by de-protection with HCl, as shown in Scheme A-2. (Acid 30 can be prepared from ester 11 by Boc-protecting the amino group and saponifying the ester group.)

Scheme A-2

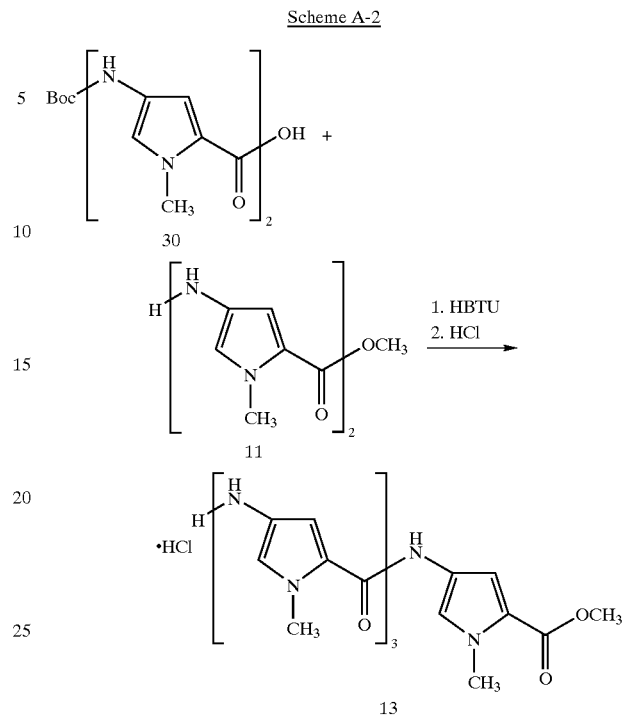

Compounds 15 and 19. A mixture of isoquinoline-3-carboxylic acid 5 (3.32 g, 1.2 equiv.) and HBTU (6.91 g, 1.14 equiv.) in DMF (30 mL) and DIEA (6 mL) was stirred at room temperature ("RT") for 45 min and added to a solution of amino ester 11 (5.00 g, 1.0 equiv.) in DMF (30 mL) and DIEA (6 mL). The mixture was stirred for 20 hr at RT and poured into ice-water (ca. 700 mL). The resulting precipitate was collected by filtration to yield crude compound 15. The precipitate was suspended in EtOH (100 mL) and $H_2O$ (100 mL). The mixture was treated with KOH (5 g), stirred at 70 to 80° C. for 17 hr, diluted with $H_2O$ (ca. 600 mL) and washed with ethyl acetate ("AcOEt") (1x). The aqueous layer was acidified to pH 3 with 1M aqueous HCl and the resulting solids collected by filtration and dried in vacuo to yield acid 19 (2.8 g, 42% yield over two steps, $^1$H-NMR).

Compounds 17 and 21. A mixture of isoquinoline-3-carboxylic acid 5 (4.47 g, 1.15 equiv.) and HBTU (9.36 g, 1.1 equiv.) in NMP (50 mL) and DIEA (10 mL) was stirred for 45 min at RT and added to a solution of amino ester 13 (12.51 g, 1.0 equiv.) in NMP (10 mL) and DIEA (2 mL). The mixture was stirred for 16 hr at RT and added dropwise to 10% aqueous $K_2CO_3$ (800 mL). The resulting precipitate of compound 17 ($^1$H-NMR) was collected by filtration. The filter cake was suspended in MeOH (200 mL) and 2M aqueous NaOH (200 mL) and stirred for 16 hr at 60° C. The mixture was diluted with $H_2O$ (500 mL) and acidified to pH 2 with ca. 4M aqueous HCl. The solids were collected by filtration and dried in vacuo to yield the carboxylic acid 21 (14.15 g, 89% over two steps).

Compound Ib-5. A mixture of acid 20 (140 mg, 1.0 equiv.) and HBTU (118 mg, 1.2 equiv.) in NMP (1 mL) and DIEA (0.3 mL) was stirred at 37° C. for 1 hr and treated with 1-(2-aminoethyl)pyrrolidine (0.4 mL). The mixture was stirred for 16 hr (37° C.), diluted with 50% aqueous AcOH (10 mL), washed with AcOEt (1x) and purified by HPLC to yield compound Ib-5 ($^1$H-NMR; mass spectrum).

Compound Ib-24. A mixture of acid 20 (100 mg, 1.0 equiv.) and BOPCl(58.2 mg, 1.2 equiv.) in NMP (1 mL) and DIEA (0.1 mL) was stirred at 37° C. for 45 min and treated with 1-(2-aminoethyl)-4-fluoropiperidine (0.08 mL, ca. 3 equiv.). The mixture was stirred for 16 hr (37° C.), diluted with 50% aqueous AcOH (10 mL) and purified by HPLC to yield compound Ib-24 ($^1$H-NMR; mass spectrum).

Compound Ib-31. A mixture of acid 21 (90 mg, 1.0 equiv.) and BOPCl (41.5 mg, 1.2 equiv.) in NMP (1 mL) and DIEA (0.1 mL) was stirred at 37° C. for 45 min and treated with 4-(2-aminoethyl)thiomorpholine (0.1 mL, ca. 5 equiv.). The mixture was stirred for 16 hr (37° C.), diluted with 50% aqueous AcOH (10 mL) and purified by HPLC to yield compound Ib-31 ($^1$H-NMR; mass spectrum).

EXAMPLE B

Scheme B-1 illustrates the synthesis of compounds having a heteroaromatic carboxamide residue other than Py—in this instance an isoxazole carboxamide residue—with compound Ib-60 as a prototype.

Scheme B-1

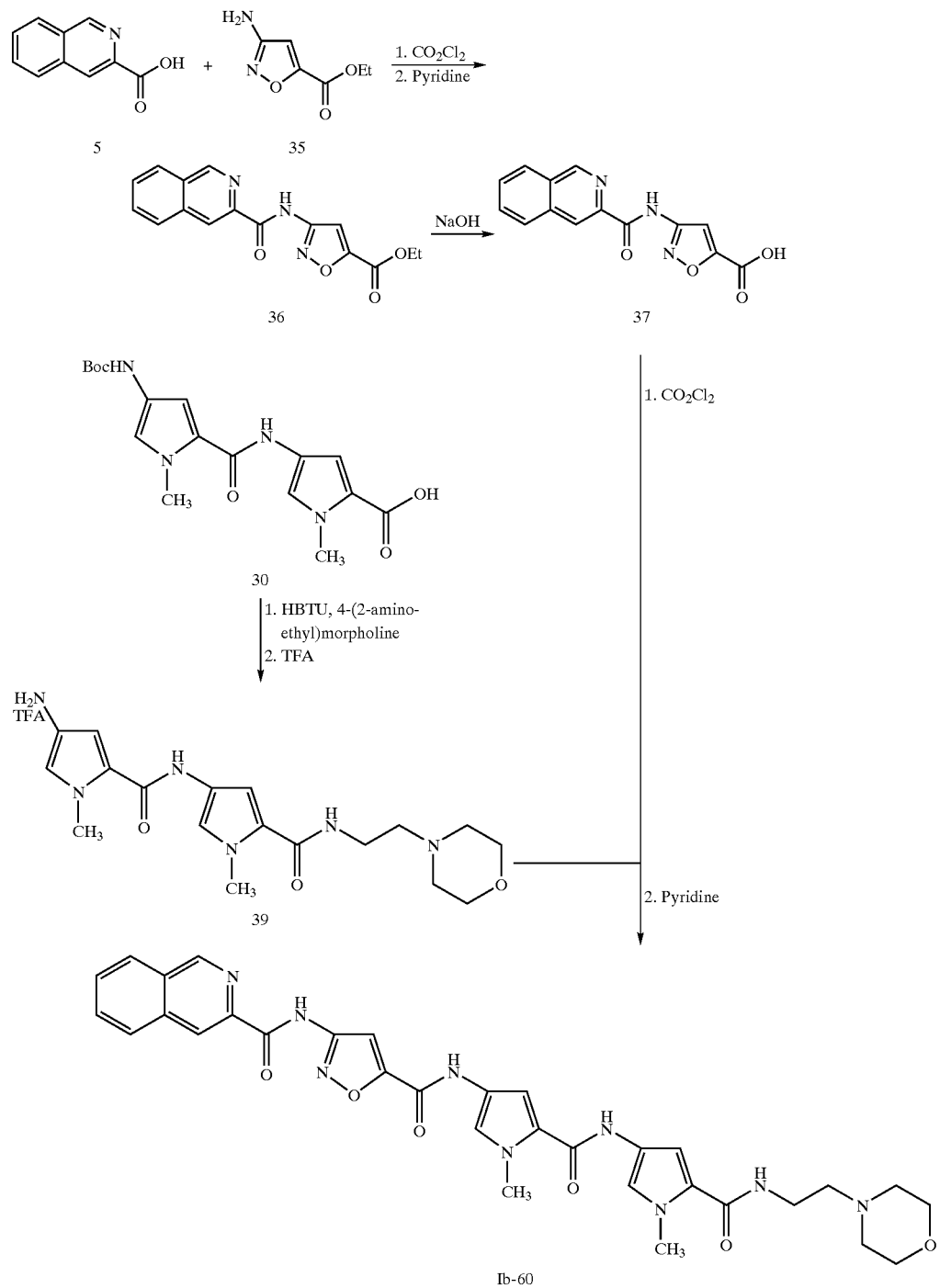

Ester amide 36. Oxalyl chloride (1.67 mL, 19.19 mmol) was added dropwise to a suspension of isoquinoline-3-carboxylic acid 5 (332.3 mg, 1.92 mmol) in THF (2 mL) and the reaction mixture was heated at reflux (85° C. oil bath) for 3 hr. All volatile components were removed in vacuo. The resulting solid (presumed acid chloride) was dissolved in NMP (1 mL) and pyridine (1 mL), and ethyl 3-aminoisoxazole-5-carboxylate 35 (Lepage et al., FR 2,750,425 (1998), 300 mg, 1.92 mmol) was added. The reaction mixture was stirred at RT for 3 hr and then added drop-wise to a rapidly stirred solution of ice-cold water (2 mL), causing precipitation of ester-amide 36 as a white solid (300 mg, 50%, $^1$H-NMR), which was collected by filtration and dried by lyophilisation.

Acid 37. Aqueous sodium hydroxide (1N, 2 mL, 2 mmol) was added to a solution of ester-amide 36 (250 mg, 0.803 mmol) in ethanol (2 mL). The reaction mixture was stirred for 30 minutes at RT, at which point TLC analysis indicated complete consumption of starting material. The mixture was then acidified to pH 2–3 with 2N aq. HCl, causing precipitation of the product acid 37 as a white solid (245 mg, quantitative yield, $^1$H-NMR), which was collected by filtration and dried by lyophilisation.

Amine 39. Carboxylic acid 30 (Scheme A-2) was converted to amide-amine 39 by activation with HBTU (0.95 eq.) in DMF/TEA at RT for 45 min, followed by addition of 4-(2-aminoethyl)morpholine (1.2 eq.) and reaction at 37° C. overnight. Volatiles were removed in vacuo, and TFA was added. The reaction mixture was stirred at RT for 3 hr. Work-up yielded amide-amine 39 as the trifluoroacetate salt.

Compound Ib-60. Oxalyl chloride (0.22 mL, 2.54 mmol) was added drop-wise to a suspension of acid 37 (72 mg, 0.254 mmol) in THF (1 mL) and the reaction heated at reflux (oil bath 85° C.) for 3 hours. All volatile components were removed in vacuo. The resulting solid (presumed acid chloride) was dissolved in NMP (0.5 mL) and pyridine (0.5 mL). A solution of amine 39 (105 mg, 0.254 mmol) in NMP (1 mL) and DIEA (0.5 mL) was added. The reaction mixture stirred at 60° C. for 12 hours, diluted with 50% acetic acid solution, and directly purified by HPLC to give the desired compound Ib-60 (25 mg, 16%, $^1$H-NMR).

EXAMPLE C

This example describes the synthesis of intermediates for the preparation of compounds of this invention having pyrrole carboxamide units in which the pyrrole nitrogen is substituted with a substituent other than methyl, as in the instance of compounds Ib-55 to Ib-57, Ib-63 to Ib-66, and Ib-68. The synthetic methodology is shown in Scheme C-1.

Scheme C-1

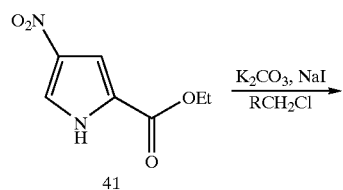

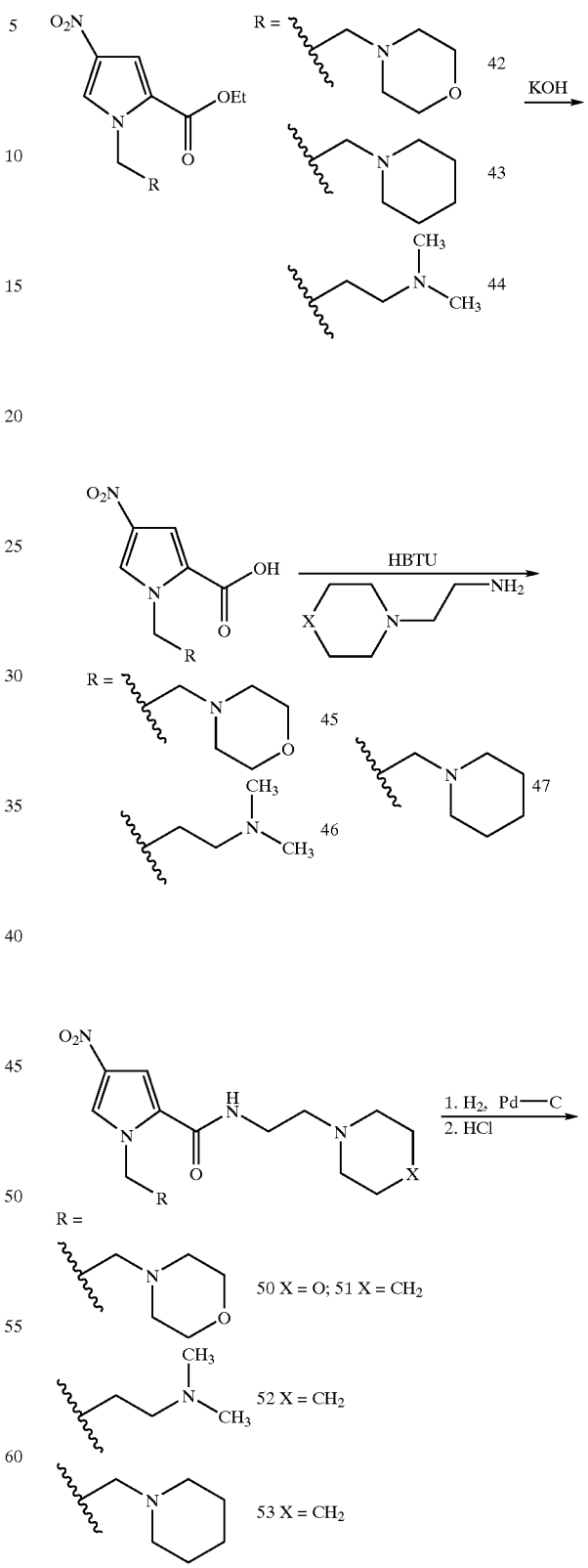

-continued

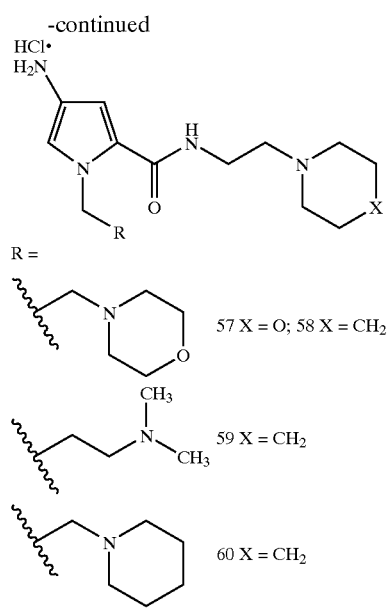

R =

57 X = O; 58 X = CH₂

59 X = CH₂

60 X = CH₂

Compounds 42–44. The synthesis of compounds 42–44 is illustrated with compound 42, the other compounds being analogously synthesizable. A mixture of ethyl 4-nitropyrrole-2-carboxylate 41 (20.00 g, 1.0 equiv.), 4-(2-chloroethyl)-mo-pholine hydrochloride (28.28 g, 1.4 equiv.), NaI (16.28 g, 1.0 equiv.) and K₂CO₃ (28.78 g, 1.92 equiv.) in DMF (200 mL) was stirred at 60° C. for 10.5 hr and poured into a mixture of H₂O and saturated aq. K₂CO₃ (550/50 mL). The resulting solution was extracted with AcOEt (4x, each 200 mL). The combined organic layers were dried (MgSO₄) and evaporated to give compound 42 as pale yellow crystals (31.4 g, 97%, ¹H-NMR).

Compounds 45. A suspension of ester 42 (31.4 g, 1.0 equiv.) and KOH (8.13 g, 2 equiv.) in EtOH (100 mL) and H₂O (100 mL) was stirred at RT for 16 hr (complete dissolution after 1 hr). The mixture was acidified with 1M aq. HCl to pH 3.0 and the resulting precipitate was collected by filtration and dried in vacuo to give compound 45 as a white solid (23.0 g, 81%, ¹H-NMR). Compounds 46 and 47 were analogously synthesized, except that workup was by neutralization to pH 7 with 1M HCl and evaporation.

Compounds 50–53 and 57–60. The synthesis of compounds 50–53 and 57–60 is illustrated with specific reference to compounds 50 and 57, the other compounds being analogously synthesizable. A mixture of the acid 45 (1.5 g, 1.0 equiv.) and HBTU (1.8 g, 1 equiv.) in DMF (8 mL) and DIEA (2 mL) was stirred at RT for 1 hr, treated with the 4-(2-aminoethyl)morpholine (0.70 mL, 1.1 equiv.) and stirred for 15 hr at RT. The solution was added dropwise to ice water (150 mL) and extracted with AcOEt (5x). The combined organic layers were dried (MgSO₄) and evaporated to give compound 50 as a brown solid (1.6 g, ¹H-NMR). The crude product was dissolved in AcOEt (50 mL) and MeOH (5 mL), treated with 10% Pd—C (ca. 100 mg), and stirred at RT under H₂ (1 atm) for 48 hr. The mixture was filtered through Celite and the solids washed with MeOH. The filtrate was concentrated in vacuo, diluted with Et₂O (250 mL) and AcOEt (50 mL), and treated with HCl (g) for 1 min. Evaporation of the solvents gave compound 57 hydrochloride as an orange solid (1.7 g), used without further purification.

EXAMPLE D

In this example, intermediates synthesized per Examples A and C are coupled to provide compounds of this invention. The synthetic scheme is summarized in Scheme D-1a, with compound Ib-56 as a representative example.

Scheme D-1

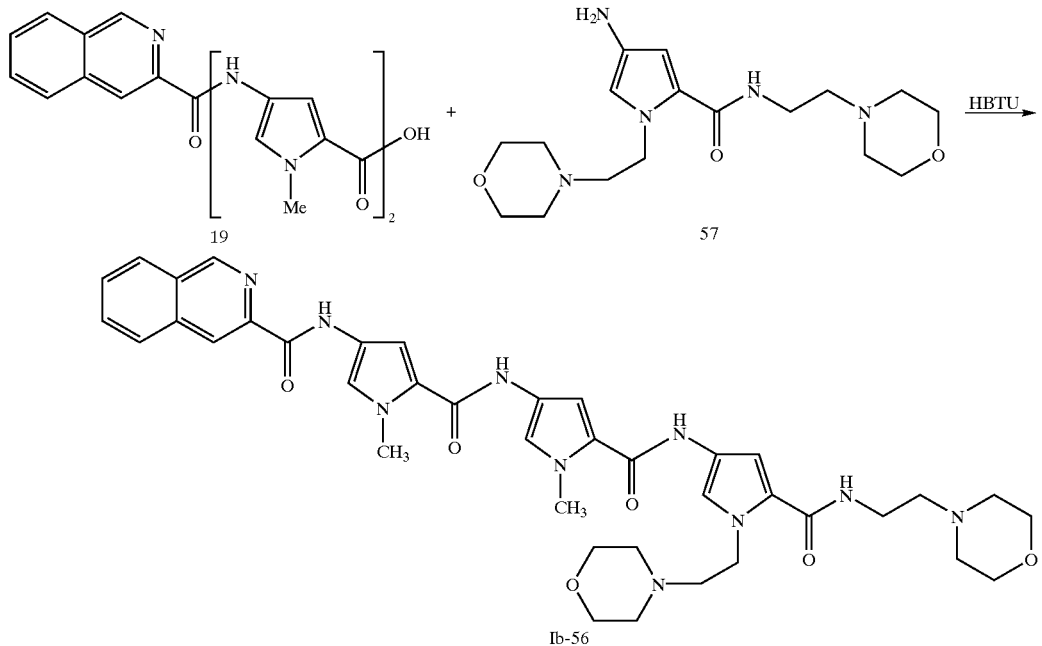

Compound Ib-56. Acid 19 (108.5 mg, 1.2 equiv.) and amine-amide 57 (100 mg, 1.0 equiv.) were coupled using HBTU/DIEA/NMP to give, after purification by HPLC, compound Ib-56 (¹H-NMR, mass spectrum). Compounds Ib-55, Ib-64, and Ib-68 were made by analogous methods.

EXAMPLE E

Scheme E-1 illustrates the synthesis of compounds having basic pendant side chains such as those found in compound Ib-73.

Amino ester 72. A suspension of the nitro ester 71 (15.0 g, 1 equiv.) and 10% Pd/C (1.0 g) in AcOEt (117 mL) and MeOH (13 mL) was stirred at RT under $H_2$ (120 psi) for 20 hr. The mixture was filtered through Celite and the solvent was evaporated from the filtrate. The resulting brown oil was

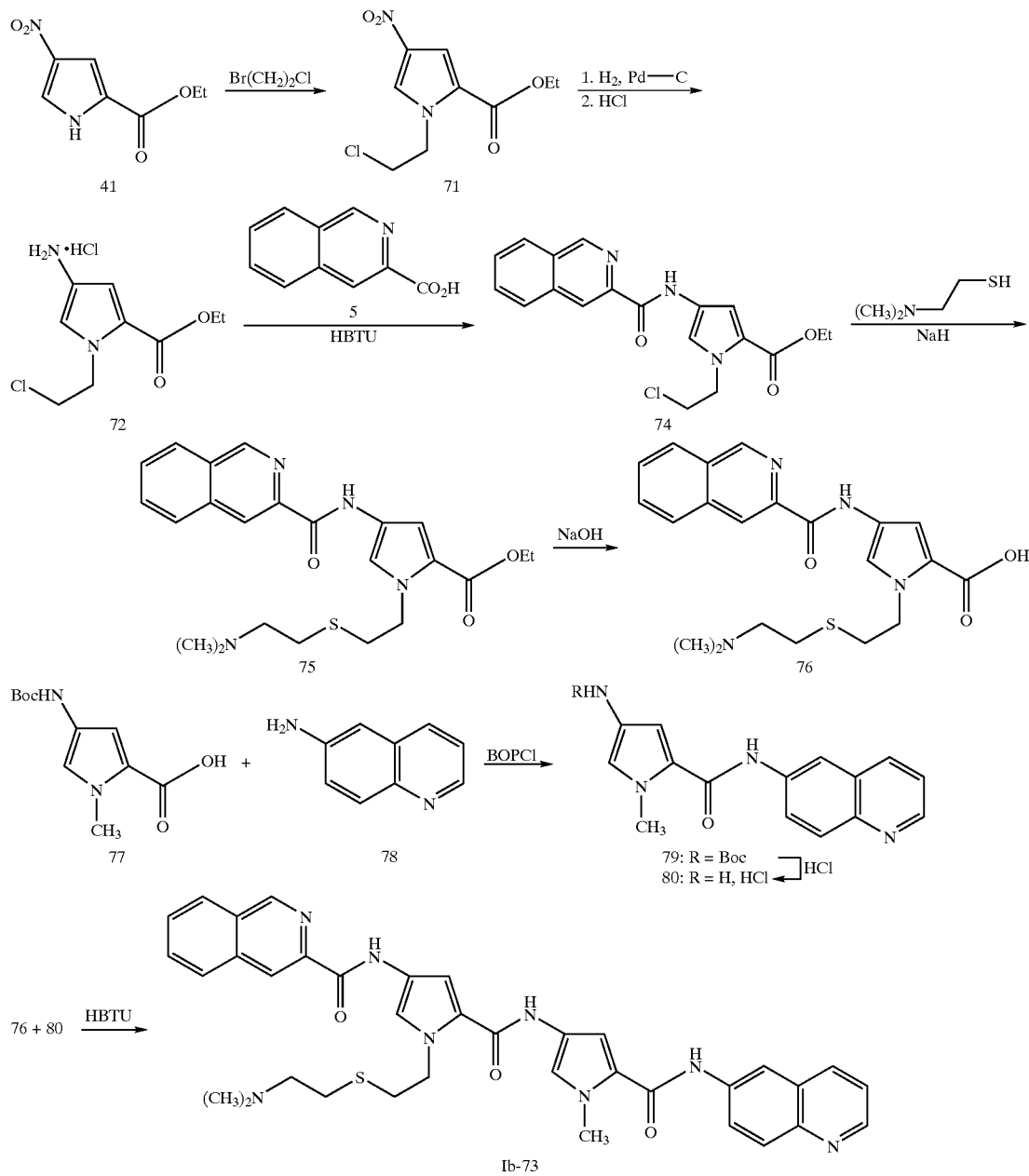

Scheme E-1

Nitro ester 71. A mixture of the pyrrole 41 (Example C) (20.00 g, 1.0 equiv.), NaI (16.28 g, 1.0 equiv.), $K_2CO_3$ (30.02 g, 2.0 equiv.) and 1-bromo-2-chloroethane (22.6 mL, 2.5 equiv.) in DMF (200 mL) was stirred at 75° C. for 2.5 hr and poured into $H_2O$ (500 mL). The mixture was treated with $Na_2S_2O_3$ (ca. 10 g) and extracted with $Et_2O$ (3x, each 300 mL). The organic layers were dried ($MgSO_4$) and evaporated to give a yellow oil. Drying at 75° C. (ca. 0.1 mbar) for 1.5 hr gave nitro ester 71 (26.77 g, 93%, $^1$H-NMR) as a crystalline yellow solid.

dissolved in $Et_2O$ (ca. 300 mL) and treated at 0° C. with HCl (g) for about 45 sec. The resulting precipitate was collected by filtration and dried to give amino ester 72 hydrochloride as a tan solid (14.03 g, 91%, $^1$H-NMR).

Isoquinoline ester 74. Isoquinoline-3-carboxylic acid 5 (Example A) (3.76 g, 1.1 equiv.) and amino pyrrole 72 (5.00 g, 1.0 equiv.) were coupled using HBTU/DIEA/DMF to give isoquinoline ester 74 as a tan solid (5.90 g, 80%, $^1$H-NMR), isolated by filtration.

Compound 75. A suspension of 2-(dimethylaminoethyl)mercaptan hydrochloride (350 mg, 2 equiv.) in DMF (5 mL) was treated at 0° C. under $N_2$ with NaH (60% disp., 200 mg, 4 equiv.). The mixture was stirred for 20 min at 0° C., treated dropwise with a solution of isoquinoline ester 74 (0.458 g, 1 equiv.) in DMF (5 mL), warmed to RT and stirred for 1 hr. The mixture was diluted with AcOEt (200 mL) and washed with sat. aqueous $K_2CO_3$ (2x, each 30 mL) and $H_2O$ (1x, 30 mL). The organic layer was dried ($MgSO_4$) and evaporated to give compound 75 as a dark solid (0.45 g, 83%, $^1$H-NMR).

Acid 76. Saponification of compound 75 (0.45 g, 1 equiv.) with NaOH/aq. MeOH at 60° C. for 3 hr gave acid 76 (0.40 g, 95%, $^1$H-NMR).

Compound 79. Acid 77 (5.00 g, 1.0 equiv.) and 6-aminoquinoline 78 (3.00 g, 1.0 equiv.) were coupled using BOPCl/DIEA/NMP to give compound 79 (3.73 g, ca. 49%), used without further purification or characterization.

Amine 80. A suspension of compound 79 (3.41 g, 1.0 equiv.) in AcOEt (100 mL, saturated with HCl gas) was stirred at 0° C. for 3 hr and poured into $Et_2O$ (300 mL). The solid was collected by filtration and dried in vacuo to give amine 80 as a dark solid (3.09 g). The crude product was used without further purification or characterization.

Compound Ib-73. Carboxylic acid 76 (50 mg, 1.1 equiv.) and amine 80 were coupled using HBTU/DIEA/NMP to yield compound Ib-73 ($^1$H-NMR, mass spectrum).

EXAMPLE F

This example illustrates the synthesis of compounds having condensed carboxamide moieties having condensed 6,5-heteroaromatic ring systems, as illustrated by compound Id-2. The synthetic approach is summarized in Scheme F-1.

Nitro ester 91. A mixture of the nitrobenzaldehyde 90 (3.00 g, 1.0 equiv.), sodium ethyl mercaptoacetate (3.10 g, 1.35 equiv.) and $Na_2CO_3$ (1.80 g, 105 equiv.) in DMSO (30 mL) was stirred at 90° C. for 15 hr and poured into $H_2O$ (350 mL). The solution was extracted with $Et_2O$ (4x). The combined organic layers were dried ($MgSO_4$) and evaporated to give the nitro ester 91 as a yellow-brown crystalline solid (3.60 g, 89%, $^1$H-NMR).

Amino ester 92. A suspension of the nitro ester 91 (2.50 g, 1.0 equiv.) and 10% Pd/C (200 mg) in AcOEt (75 mL) and MeOH (8 mL) was stirred at RT under $H_2$ atmosphere (150 psi) for 19 hr. The mixture was filtered through Celite. Evaporation of the solvent gave amino ester 92 as a yellow solid, used without further purification or characterization.

Boc-protected ester 93. Crude amino ester 92 was dissolved in DMF (16 mL) and DIEA (4 mL), treated with $(Boc)_2O$ (2.08 g, 1.5 equiv.) and stirred at RT for 8 hr. The mixture was poured into $H_2O$ (300 mL) and extracted with $Et_2O$ (4x). The combined organic layers were dried ($MgSO_4$) and evaporated to give Boc-protected ester 93 as a pale yellow solid (2.70 g, 81% yield over two steps, $^1$H-NMR).

Acid 94. Saponification of the ester 93 (2.70 g, 1 equiv.) using KOH/aq. EtOH at 65° C. for 4 hr gave acid 94 as a tan solid (2.28 g, 95%, $^1$H-NMR).

Amine 96. Acid 94 (600 mg, 1.0 equiv.) and 4-(2-aminoethyl)morpholine (280 mg, 1.05 equiv.) were coupled using HBTU/DIEA/NMP to give compound 95 as an orange tar. Crude compound 95 was dissolved in AcOEt (50 mL) and saturated with HCl (g) and stirred for 2 hr at RT. The resulting precipitate was collected by filtration and dried to give amine 96 as a tan solid (ca. 550 mg).

Compound Id-2. Acid 19 (Example A) (79.6 mg, 1.2 equiv.) and amine 96 (60 mg, 1.0 equiv.) were coupled using HBTU/DIEA/NMP to give, following HPLC purification, compound Id-2 ($^1$H-NMR, EI-mass spectrum).

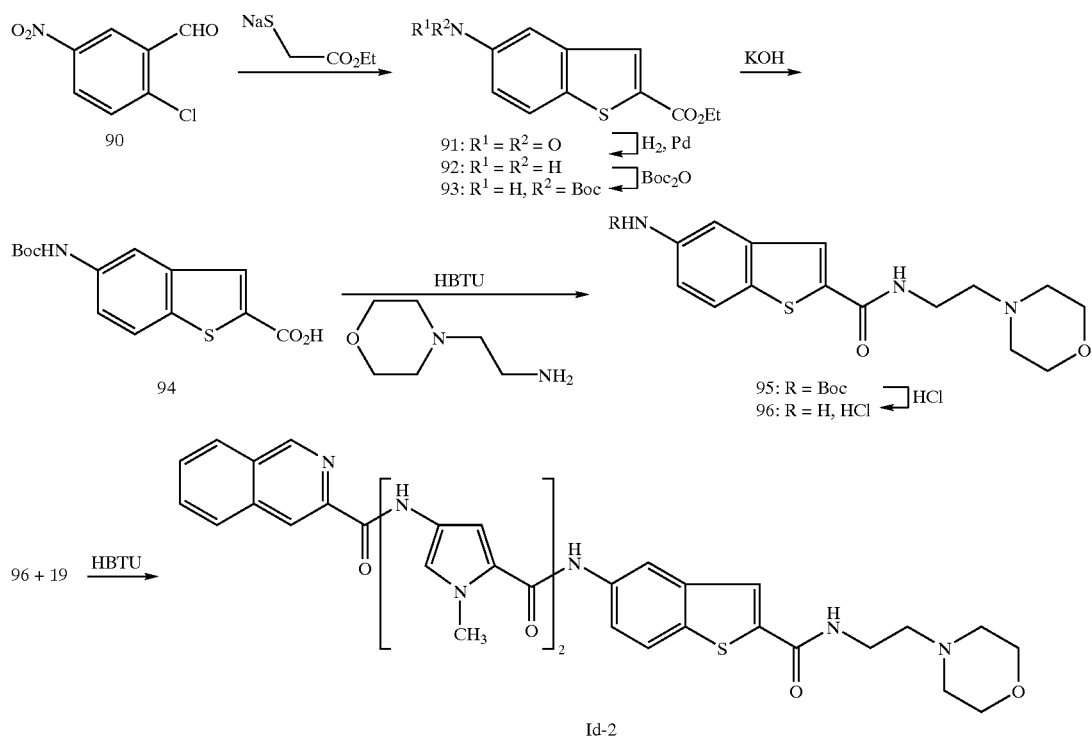

Scheme F-1

EXAMPLE G

This example illustrates the synthesis of compounds having an N-unsubstituted pyrrole carboxamide unit, examples of which are Ib-50, Ib-54, Ib-62, Ib-67 and Ib-69 to Ib-71.

Scheme G-1 illustrates, with compound Ib-75 as a model, the procedure for the instance in which an N-unsubstituted pyrrole carboxamide group has two consecutive Py groups attached to its carboxyl side.

Trimer 103. A mixture of ketone 101 (Bremer et al., Bioorg. Med. Chem. 2000, 8, 1947–1955) (6.00 g, 1 equiv.) and amine 11 (Example A) (7.27 g, 1 equiv.) in NMP (50 mL) and DIEA (9.5 mL) was stirred for 2 hr at RT and added dropwise to ice water (800 mL). The resulting solid was collected by filtration and dried in vacuo to give the trimer 103 (9.40 g, 97%, $^1$H-NMR).

Amine 104. Hydrogenation of trimer 103 (1.19 g, 1 equiv.) at 100 psi $H_2$ with 10% Pd—C (0.2 g) catalyst in AcOEt:MeOH (1:1 v/v) for 16 hr gave amine 104 hydro-

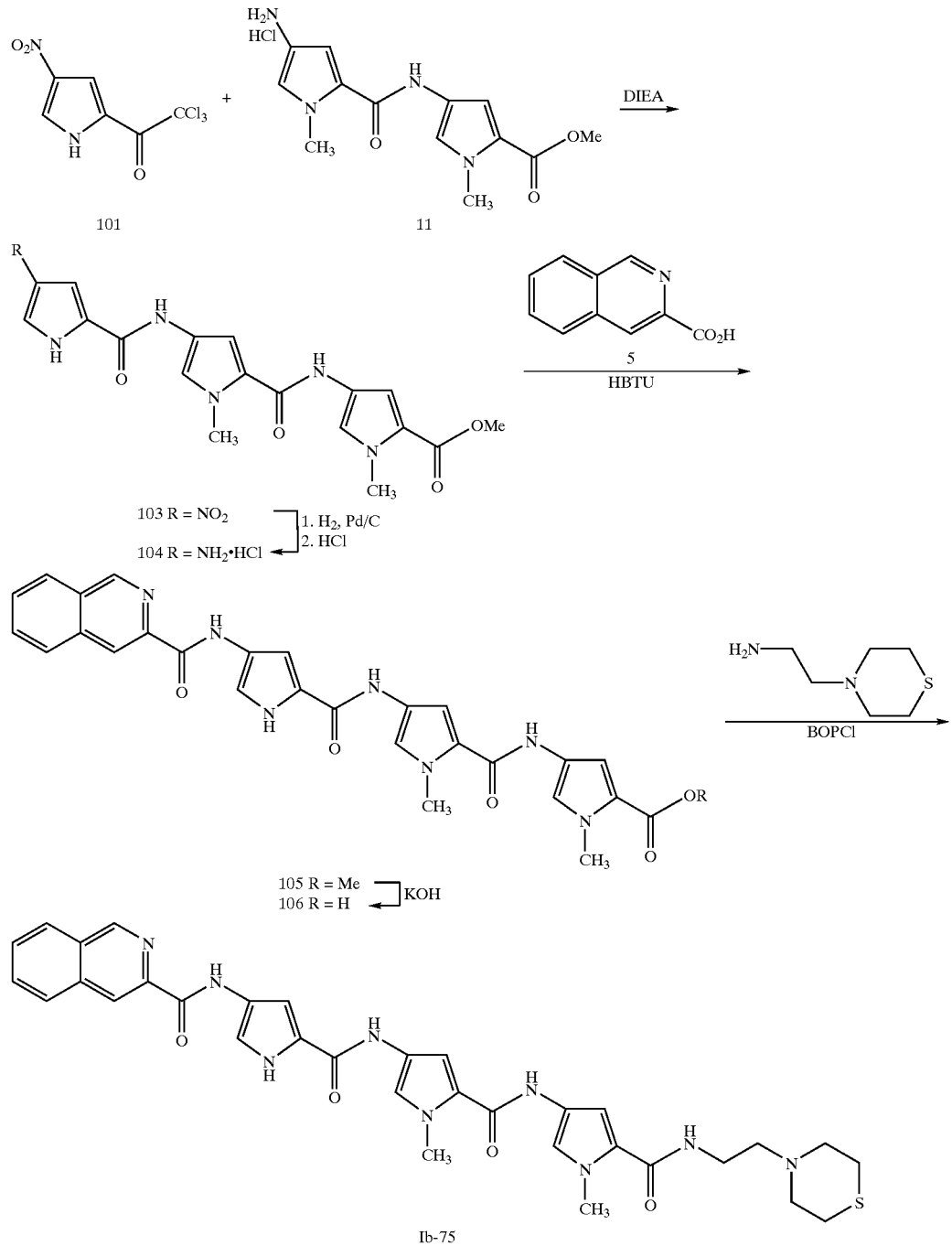

Scheme G-1 chloride (1.0 g, 83%, ¹H-NMR), collected by filtration after precipitation with HCl.

Tetrameric ester 105. Isoquinoline-3-carboxylic acid 5 (1.33 g, 1.2 equiv.) and amine 104 (2.90 g, 1.0 equiv.) were coupled using HBTU/DIEA/NMP to give, after work-up and collection by filtration, tetrameric ester 105 (3.5 g, 96%, ¹H-NMR).

Tetrameric acid 106. Saponification of tetrameric ester 105 (3.50 g, 1 equiv.) with KOH/aq. EtOH for 8 hr at 60° C. gave, after acidification and work-up, tetrameric acid 106 (2.34 g, 68%, ¹H-NMR).

Compound Ib-75. Tetrameric acid 106 (80 mg, 1 equiv.) and 4-(2-aminoethyl)-thiomorpholine (0.1 mL) were coupled using HBTU/DIEA/NMP (65 mg, 1.1 equiv.) to give, after preparative HPLC, compound Ib-75 (¹H-NMR, mass spectrum).

Scheme G-2 below illustrates the preparation intermediates for the synthesis of compounds such as Ib-67, wherein an N-unsubstituted pyrrole carboxamide has a single Py group attached to its carboxyl side.

Scheme G-2

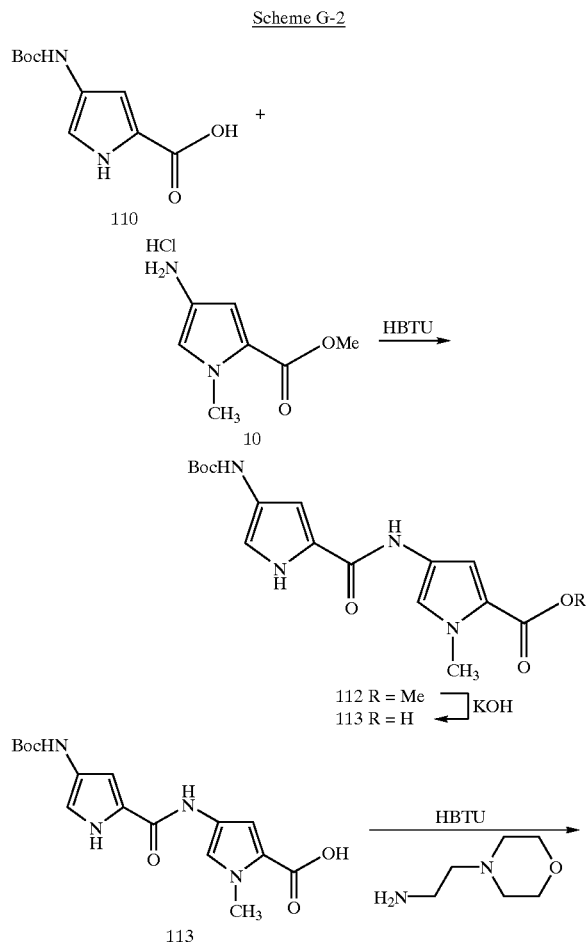

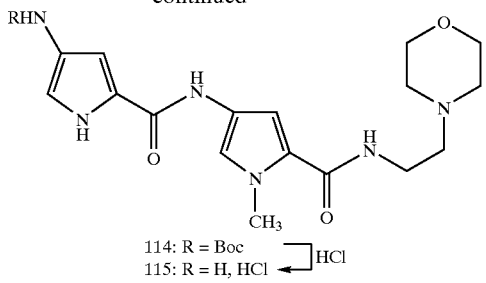

Dimer 112. Acid 110 (19.58 g, 1.1 equiv.) and amine 10 (Example A) (15.0 g, 1.0 equiv.) were coupled using HBTU/DIEA/DMF to give dimer 112 as an orange brown oil (¹H-NMR).

Acid 113. Saponification of the dimer 112 (10.0 g, 1 equiv.) in KOH/EtOH/H₂O gave, after acidification and work-up, acid 113 as a brown solid (¹H-NMR).

Amine 115. Acid 113 (4.00 g, 1.1 equiv.) and 4-(2-aminoethyl)morpholine (1.37 mL, 1.0 equiv.) were coupled using HBTU/DIEA/DMF to give intermediate 114 (mass spectrum). Crude intermediate 114 was dissolved in AcO-Et:MeOH (2:1 v/v), saturated with HCl (g) and stirred for 1.5 hr. Evaporation of the solvent left a brown oil that was dissolved in MeOH (25 mL) with sonication. The solution was added dropwise to Et₂O (250 mL) upon which a brown solid precipitated. Decantation of the solvent and drying gave amine 115 (¹H-NMR).

EXAMPLE H

Scheme H-1 below describes the synthesis of a building block for compounds having an N-unsustituted pyrrole carboxamide group at the C-terminus, such as compound Ib-54.

Scheme H-1

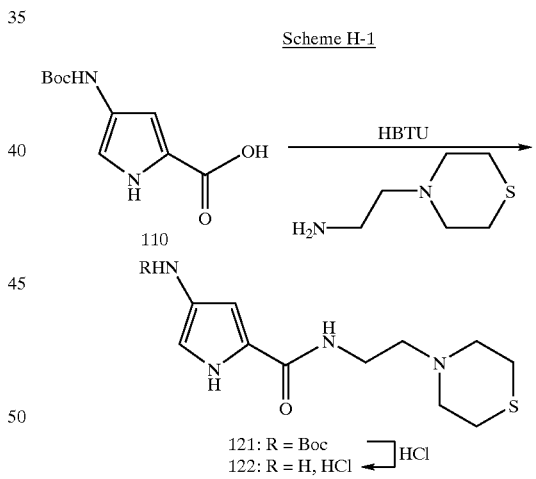

Amine 122. Acid 110 (Scheme G-2) (2.00 g, 1.0 equiv.) and 4-(2-aminoethyl)thiomorpholine (1.68 g, 1.3 equiv.) were coupled using HBTU/DIEA/DMF to give, after flash chromatography (1%TEA, CH₂Cl₂ to CH₂Cl₂/MeOH (9:1) gradient), intermediate 121 as a glassy yellow solid (320 mg). Intermediate 121 was dissolved in AcOEt (30 mL), treated with HCl-saturated AcOEt (75 mL) and stirred for 2 hr at RT. Evaporation of the solvent left amine 122 hydrochloride as a white solid (300 mg, ¹H-NMR, mass spectrum), used to make compound Ib-54.

EXAMPLE I

Scheme I-1 below illustrates the synthesis of intermediates usable for the preparation of compounds of this invention having isothiazole carboxamide residues

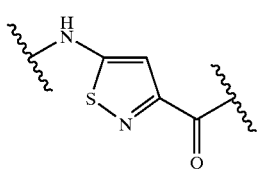

as exemplified by compounds Ib-52 and Ib-53.

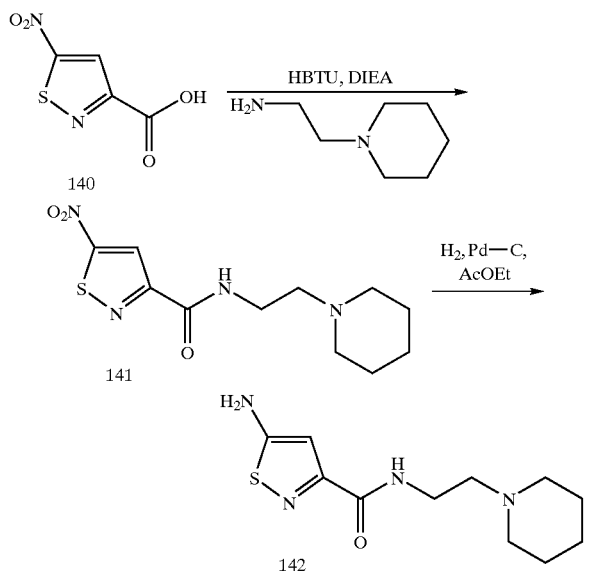

Nitro compound 141. Nitro acid 140 (300 mg, 1.2 equiv., Heindl et al., *Eur. J Med. Chem.—Chimica Therapeutica*, 1975, 10, 591–593) and 1-(2-aminoethyl)piperidine (204 μL, 1.0 equiv.) were coupled using HBTU/DIEA/DMF to give nitro compound 141 (400 mg, 98%, $^1$H-NMR).

Amine 142. Nitro compound 141 (400 mg) was hydrogenated under 1 atm $H_2$ using 10% Pd—C (ca. 500 mg) in AcOEt (30 mL) at RT for 24 hr to give amine 142 as a light yellow powder (10 mg, 27%, ca. 90 to 95% pure by $^1$H-NMR). Without further purification, this material was used for the synthesis of compounds Ib-52 and Ib-53.

Analogous compounds such as 143 and 144

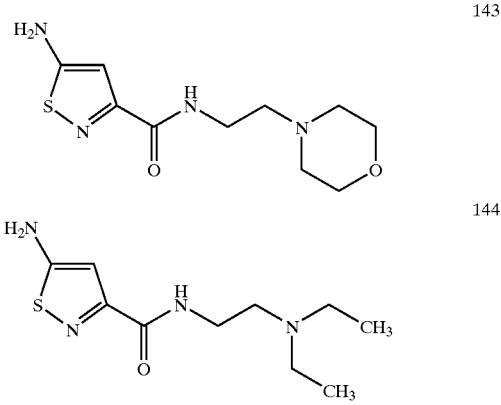

were prepared by replacing the 1-(2-aminoethyl)piperidine with a different amine.

EXAMPLE J

Scheme J-1 below describes the preparation of an intermediate for the synthesis of compounds such as Ib-72.

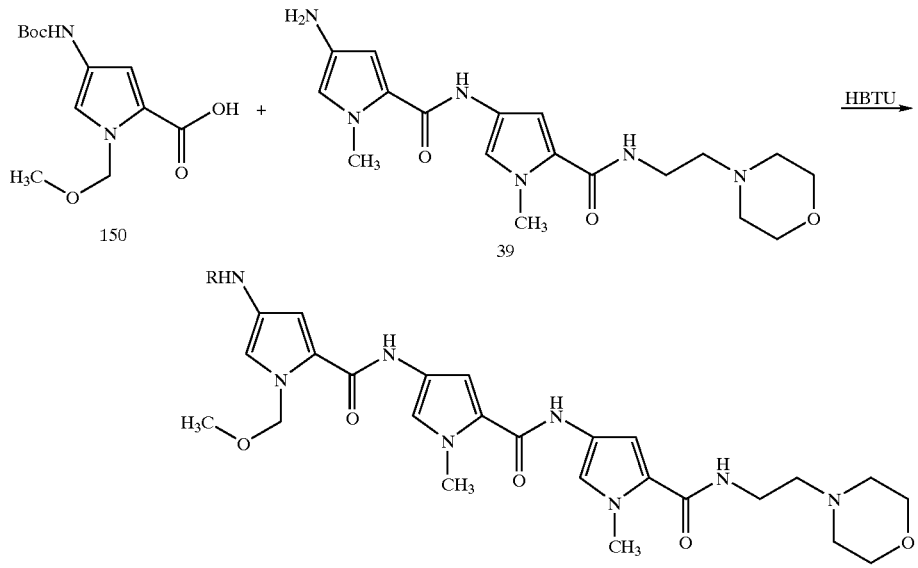

Acid 150. Acid 150 was prepared by alkylation of nitro pyrrole ester 41 (Example C) with MOMCl followed by hydrogenation (H₂, Pd) and Boc-protection (Boc₂O). The Boc-protected amino ester was saponified to give acid 150.

Compound 152. Acid 150 (1.66 g, 1.1 equiv.) and amine 39 (Example B) (2.50 g, 1.0 equiv.) were coupled using HBTU/DIEA/DMF to give, after flash chromatography (CH₂Cl₂ and 0 to 15% MeOH gradient) of the crude product, compound 151 (1.7 g) as a glassy solid. Compound 151 was dissolved in AcOEt (50 mL), treated with HCl-saturated AcOEt (50 mL) and stirred at 0° C. for 1.5 hr. Evaporation of the solvent gave compound 152 as a tan solid (1.49 g, mass spectrum). The ¹H-NMR was consistent with assigned structure, but showed signals of minor impurities, which were not further characterized.

EXAMPLE K

Scheme K-1 below depicts the synthesis of amine 162, used in the synthesis of compound Ib-58.

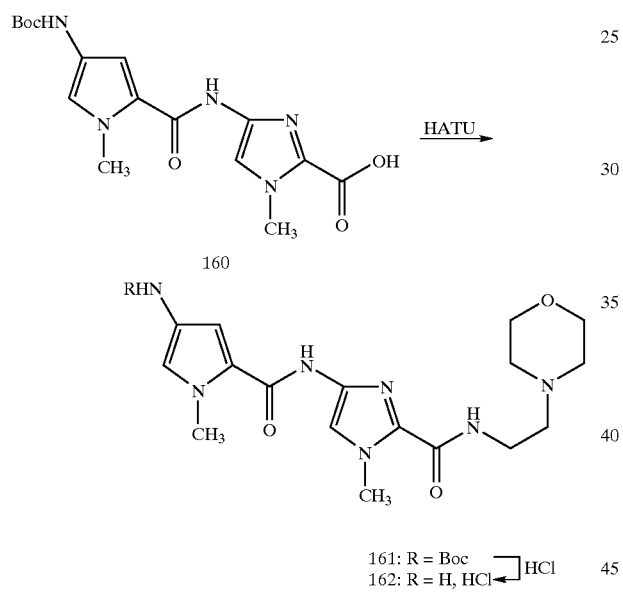

Compound 161. A mixture of dimeric acid 160 (U.S. Pat. No. 6,090,047) (0.50 g, 1.2 equiv.) and HATU (0.496 g, 1.14 equiv.) in DMF (5 mL) and DIEA (0.5 mL) was stirred at RT for 30 min and treated with 4-(2-aminoethyl)morpholine (150 mg, 1 equiv.). The mixture was stirred for 21 hr at RT, diluted with H₂O (ca. 150 mL) and extracted with AcOEt (4×50 mL). The combined organic layers were dried (MgSO₄) and evaporated to give compound 161 (ca. 640 mg, ¹H-NMR (minor impurities)), used without further purification.

Amine 162. A solution of compound 161 (640 mg, 1.0 equiv.) in AcOEt (20 mL) and Et₂O (15 mL) was saturated at RT with HCl (g). The resulting solids were collected by filtration and dried to give amine 162 (¹H-NMR).

EXAMPLE L

Scheme L-1 below shows the synthesis of intermediate amine 172, used in the preparation of compound Ib-57.

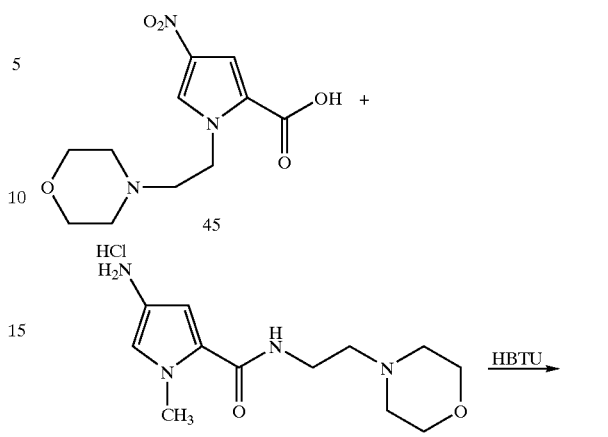

Amine 172. Nitro acid 45 (Example C) (1.05 g, 1.1 equiv.) and amine 170 (prepared from acid 77 (Example E) by analogy to the conversion of compound 30 to compound 39 in Example B) (1.00 g, 1.0 equiv.) were coupled using HBTU/DIEA/DMF to give compound 171 as a brown tar. Hydrogenation of crude compound 171 (150 psi H₂, 10% Pd—C, AcOEt:MeOH (9:1 v/v), RT, 23 hr) gave amine 172 as a brown solid (¹H-NMR), isolated as the hydrochloride salt.

Amine 172 was reacted with dimeric acid 18 (Example A) using HBTU/DIEA in NMP to yield compound Ib-57 (¹H-NMR, mass spectrum).

EXAMPLE M

Scheme M-1 below summarizes the synthesis of a carboxamide building block having a thiophene ring, suitable for making compounds such as Ib-51.

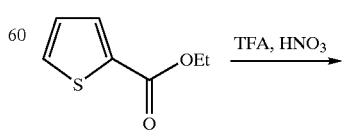

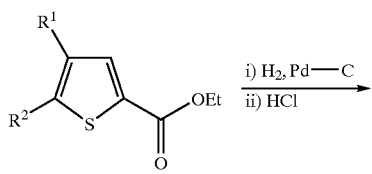

176: R¹ = NO₂, R² = H
177: R¹ = H, R² = NO₂

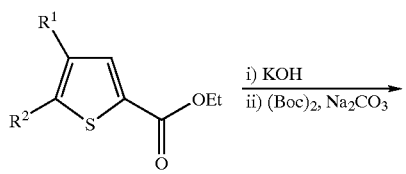

178: R¹ = NH₃Cl, R² = H
179: R¹ = H, R² = NH₃Cl

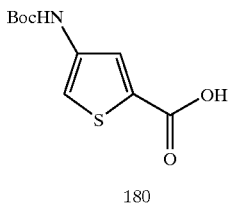

180

Nitro esters 176/177. A solution of ethyl-2-thiophene carboxylate 175 (200 g, 1 mol) in TFA (200 mL) was slowly added to a mixture of TFA (900 mL) and fuming nitric acid (200 mL) at 5° C. The cooling was removed and the reaction mixture stirred at 45° C. for ca. 14 hr, cooled to ca. 10° C., and poured into vigorously stirred ice water (4 L). The resulting precipitate was collected by filtration and washed with ice water (2x). Lyophilization of the resulting solids gave a mixture of nitro esters 176 and 177 (2:3, as evidenced by ¹H-NMR, 194.2 g, 79%).

Amines 178/179. A mixture of nitro esters 176 and 177 (2:3, 20 g) was hydrogenated (100 psi H₂, 10% Pd—C, EtOAc:MeOH (9:1 v/v), RT, 6 days) to give a mixture of amines 178 and 179 (0.9:1 as evidenced by 1H-NMR, 19.02 g, 93%).

Acid 180. Amine 178 was selectively saponified by treating a mixture of amines 178 and 179 (0.9/1, 15 g) in methanol (500 mL) at 0° C. with a solution of KOH (9 g) in H₂O (75 mL), with stirring, for 3 hr. The reaction mixture was then diluted with H₂O (400 mL) and washed with EtOAc (3x, 200 mL). The aqueous layer was neutralized to pH 6.5 with a 1M aq. HCl solution, treated with Na₂CO₃ (15 g) and a solution of Boc-anhydride (15 g) in dioxane (150 mL) and stirred for 24 hr at RT. The reaction mixture was washed with EtOAc (3x, 200 mL), cooled to 0° C., acidified to pH 2.8 with aqueous HCl (50%), and extracted with EtOAc (3x, 200 mL). The combined organic layers were dried (MgSO₄) and evaporated. The remaining oil was dissolved in methanol and treated with activated carbon (5 g). The mixture was filtered through Celite and the filtrate evaporated to yield acid 180 free of the other isomers.

EXAMPLE N

This example describes the synthesis of compound Ic-1, representative of molecules containing an amino benzamide unit. The synthetic route is summarized in Scheme N-1. Compounds having other C-terminal amino groups, such as Ic-4, can be prepared analogously.

Scheme N-1

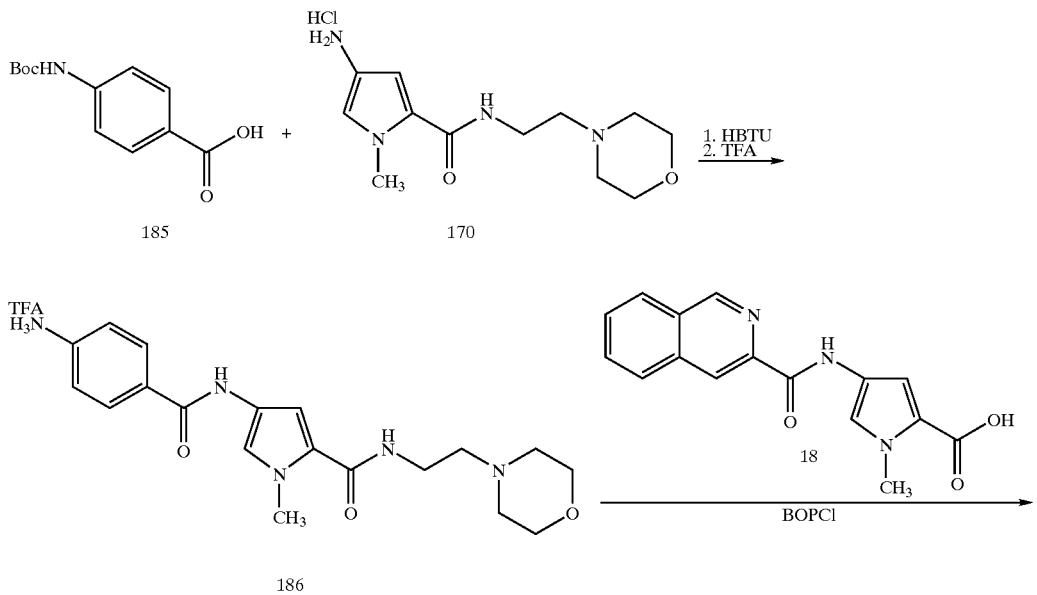

-continued

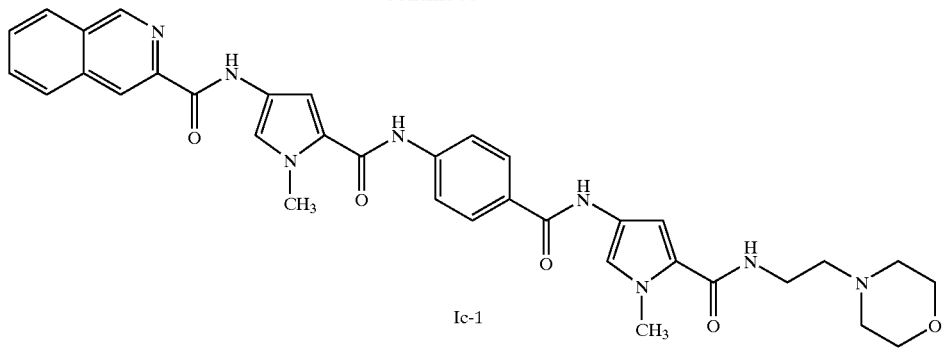

Ic-1

Amine 186. 4-Boc-aminobenzoic acid 185 (0.85 g, 3.6 mmol) and amine 170 (Example L) were coupled using HBTU/DIEA/NMP to give crude Boc-protected product. Treatment with TFA (10 mL, excess) at room temperature for 1 hour removed the Boc group. Volatile components were then removed under vacuum to give amine 186 as the TFA salt, which was used without further purification.

Compound Ic-1. BOPCl (140 mg, 0.55 mmol) and acid 18 (Example A) (177 mg, 0.6 mmol) were dissolved in NMP (4 mL) and DIEA (0.7 mL, 2 mmol) and the reaction stirred at 40° C. for 30 minutes. Amine 186 (0.5 mL, 1M solution in NMP, 0.5 mmol) was then added and the reaction shaken at 60° C. overnight. The reaction was diluted in 40% acetic acid solution to a total volume of 15 mL and the product obtained from HPLC purification of the reaction mixture. Compound Ic-1 was obtained as a pale yellow solid ($^1$H-NMR).

EXAMPLE O

The synthesis of a compound of this invention having a quatemized nitrogen group is illustrated, with specific reference to compound Ib-74 (Scheme O-1).

Scheme O-1

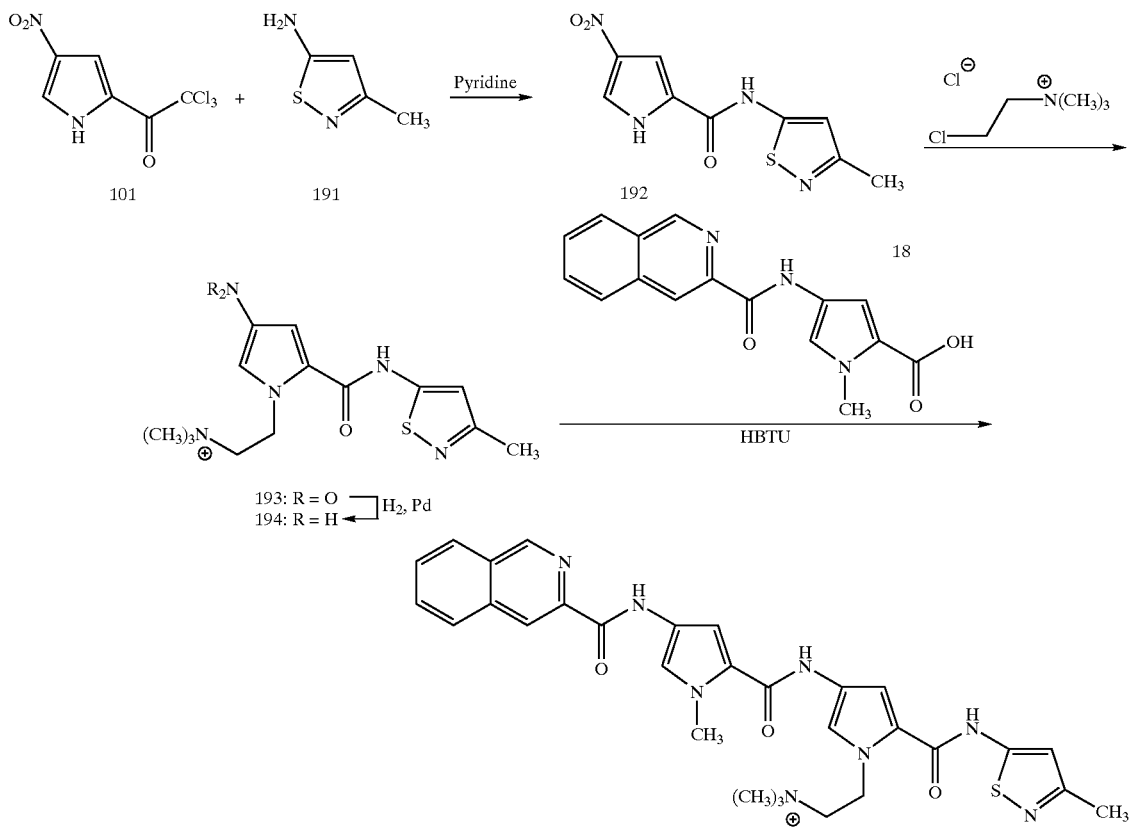

Ib-74

Compound 192. A mixture of the trichloromethyl ketone 101(Example G) (50.00 g, 1.05 equiv.) and 5-amino-3-methylisothiazole 191 (29.15 g, 1.0 equiv.) in DMF (300 mL) and pyridine (75 mL) was stirred at 65° C. for 22 hr. The mixture was poured into ice-water (3.6 L) and the resulting precipitate collected by filtration, washed with $H_2O$ and dried in vacuo to give compound 192 as a light tan solid (48.9 g, >95%, $^1$H-NMR).

Compound 193. A mixture of the compound 192 (2.00 g, 1.0 equiv.), 2-chloroethyltrimethylammonium chloride (3.14 g, 2.5 equiv.), NaI (1.19 g, 1.0 equiv.) and $K_2CO_3$ (3.29 g, 3.0 equiv.) in NMP (80 mL) was stirred at 65–80° C. for 24 hr, treated with additional chloroethyltrimethylammonium chloride (1.2 g) and stirred for 3 hr at 80° C. The mixture was diluted with $H_2O$ (150 mL) and washed with AcOEt (6x). The crystalline material formed in the aqueous phase was collected by filtration to give compound 193 as orange crystals (360 mg, 13%, $^1$H-NMR, mass spectrum).

Compound 194. Compound 193 (360 mg, 1 equiv.) was hydrogenated (1 atm $H_2$, 10% Pd—C, AcOEt:MeOH (1:9 v/v), RT, 7 hr) to give compound 194 as an orange solid ($^1$H-NMR, mass spectrum).

Compound Ib-74. Carboxylic acid 18 (Example A) (50.3 mg, 1.3 equiv.) and compound 194 (45 mg, 1.0 equiv.) were coupled using HBTU/DIEA/NMP to give, after purification by HPLC, compound Ib-74 ($^1$H-NMR, mass spectrum), presumably as the acetate salt.

EXAMPLE P

This example describes a generally applicable protocol for the guanidylation of primary amines, using compound Ib-23 as a model.

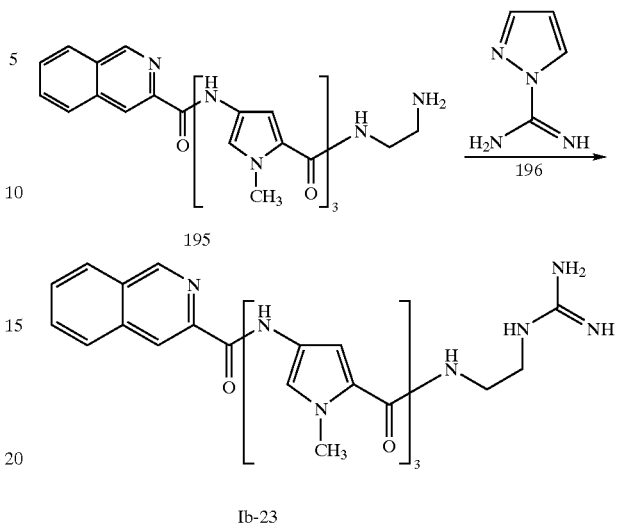

Scheme P-1

A mixture of primary amine 195 and pyrazole 196 (ca. 6 equiv.) in DMF and DIEA was stirred at RT for ca. 16 hr. The reaction mixture was diluted with 50% aqueous AcOH and purified by HPLC to yield compound Ib-23 ($^1$H-NMR, mass spectrum).

EXAMPLE Q

This example illustrates the synthesis of a compound having quatemized nitrogen group at the C-terminus, with specific reference in Scheme Q-1 to compound Ib-34.

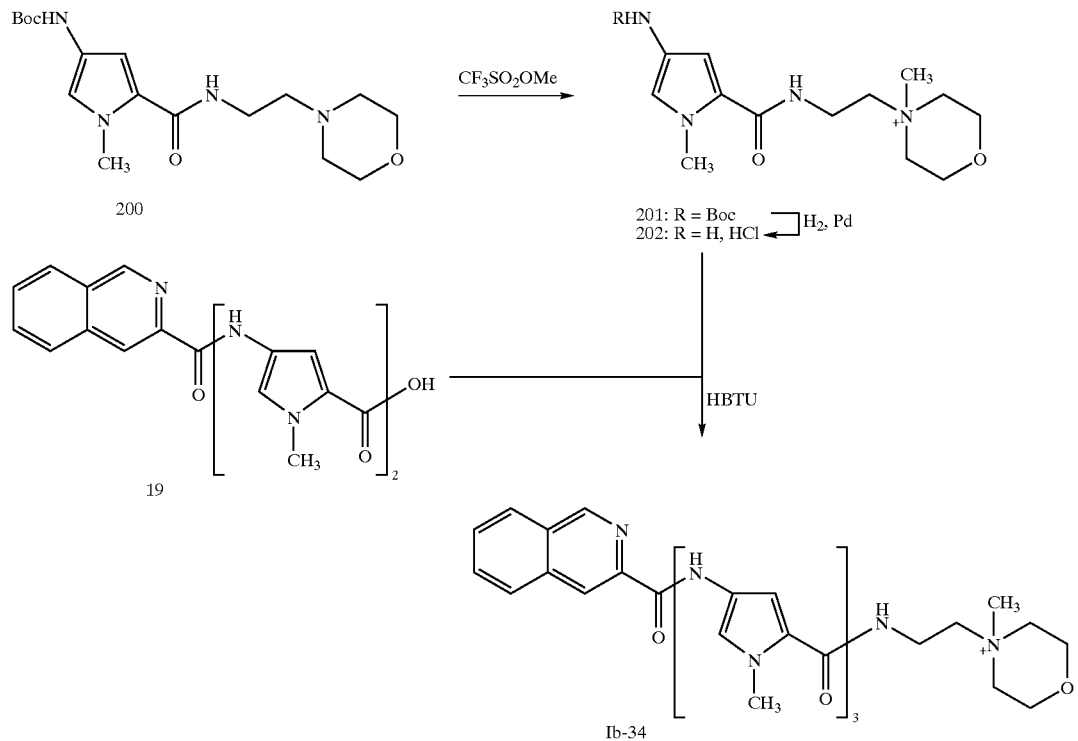

Scheme Q-1

Compound 201. A solution of compound 200 (1.00 g, 1.0 equiv.) in CH$_2$Cl$_2$ (10 mL) was treated at RT with methyl triflate (0.337 mL, 1.05 equiv.) and stirred for 2 hr. The mixture was treated with DIEA (0.5 mL) and additional methyl trifluoromethanesulfonate (0.3 mL). Stirring was continued for 1.5 hr and the solvent was evaporated. The $^1$H-NMR of the crude product was in agreement with the structure of compound 201, but showed minor impurities. The material was used without further purification.

Compound 202. A solution of crude compound 201 in MeOH (ca. 40 mL) was saturated with HCl (g) for about 20 seconds and stirred at RT for 1 hr. Evaporation of the solvent gave compound 202 ($^1$H-NMR, mass spectrum).

Compound Ib-34. Carboxylic acid 19 (Example A) (88.7 mg, 1.2 equiv.) and compound 202 (60 mg, 1.0 equiv.) were coupled using HBTU/DIEA/NMP to give, after purification by HPLC, compound Ib-34 ($^1$H-NMR, mass spectrum), presumably as the is acetate salt.

EXAMPLE R

This example relates to compounds in which —Z(R$^2$)$_n$ is

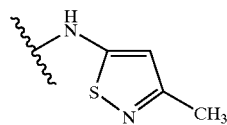

(e.g., Ib-65, Ib-66 and Ib-74). Generally, they are made by coupling commercially available 5-amino-3-methylisothiazole with a complementary carboxylic acid intermediate. The coupling preferably is effected with HATU, which produces a more reactive activated ester than HBTU, compensating for the diminished reactivity of the isothiazole amine group. Also, it may be desirable to run the coupling reaction at a higher temperature.

Scheme R-1 below shows a procedural variant employed in the synthesis of compound Ib-63.

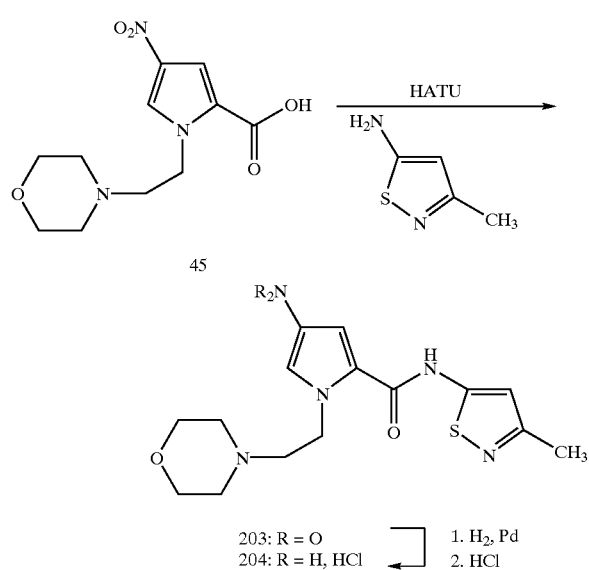

Compound 204. A mixture of the carboxylic acid 45 (Example C) (1.57 g, 1.0 equiv.) and HATU (2.21 g, 1.0 equiv.) in DMF (8 mL) and DIEA (1.5 mL) was stirred at RT for 30 min and added to a solution of 5-amino-3-methylisothiazole (0.88 g, 1.0 equiv.) in DMF (5 mL) and DIEA (1 mL). The mixture was stirred for 8 hr at 60° C. and 12 hr at is RT, treated with H$_2$O and extracted with AcOEt (3x). The combined organic layers were dried (MgSO$_4$) and evaporated to give compound 203 ($^1$H-NMR). Crude compound 203 was hydrogenated (100 psi H$_2$, 10% Pd—C, AcOEt:MeOH (1:1 v/v), RT, 24 hr) to give compound 204, used without further purification.

Scheme R-2 below shows another procedural variation, applicable for making precursors of compounds such as Ib-65 and Ib-66.

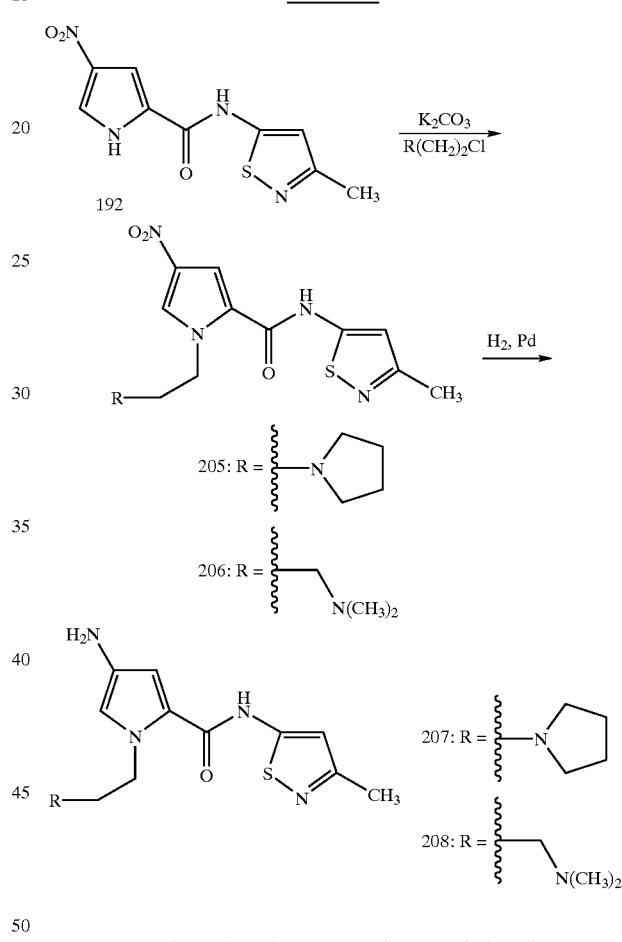

Compounds 205 and 207. A mixture of the dimer 192 (Example O) (3.0 g, 1.0 equiv.), 1-(2-chloroethyl)pyrrolidine hydrochloride (2.83 g, 1.4 equiv.), NaI (1.96 g, 1.1 equiv.) and K$_2$CO$_3$ (3.29 g, 2.0 equiv.) in DMF (30 mL) was stirred at 65° C. for 23 hr, treated with additional 1-(2-chloroethyl)pyrrolidine hydrochloride (3.0 g) and stirred for 24 hr. The reaction mixture was poured into a mixture of H$_2$O (150 mL) and sat. aqueous K$_2$CO$_3$ and extracted with AcOEt (5x). The combined organic layers were dried (MgSO$_4$) and evaporated to give a tar (3.36 g). The $^1$H-NMR indicated the presence of two products. The material was used without further purification. Crude compound 205 was hydrogenated (150 psi H$_2$, 10%Pd—C, AcOEt/MeOH (1:1 v/v), RT, 19 hr) to give compound 207 as a tan solid (3.09 g).

Compounds 206 and 208 were analogously synthesized.

EXAMPLE S

Scheme S-1 below relates to the synthesis of intermediates for the preparation of compounds of this invention having a C-terminal ester group.

Scheme S-1

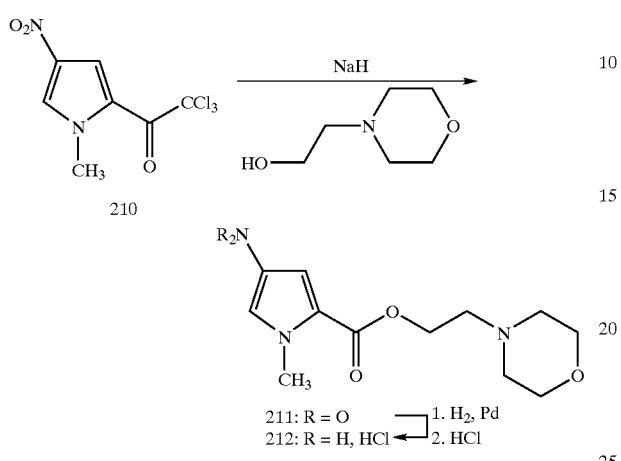

211: R = O  ⎤ 1. H₂, Pd
212: R = H, HCl ⎦ 2. HCl

Amine 212. A solution of 4-(2-hydroxyethyl)morpholine (3.4 mL, 3.0 equiv.) in THF (20 mL) was treated at 0° C. portionwise with NaH (0.37 g, 1.0 equiv., 60% in dispersion). The mixture was stirred for 20 min until a clear solution was observed and treated with a solution of the trichloromethyl ketone 210 (Baird et al., J. Am. Chem. Soc. 1996, 118, 6141–6146) (2.52 g, 1.0 equiv.) in THF (10 mL). The mixture was stirred for 3 hr at 0° C., carefully diluted with sat. aqueous K₂CO₃ and AcOEt. The layers were separated and the aqueous phase extracted with AcOEt (3x). The combined organic layers were dried (MgSO₄) and evaporated to give nitro compound 211 ($^1$H-NMR, mass spectrum). Crude compound 211 was dissolved in AcOEt (15 mL) and MeOH (15 mL), treated with 10%Pd—C (0.10 g) and stirred at RT under H₂ atmosphere (120 psi) for 12 hr. The mixture was filtered through Celite and the filtrate evaporated, dissolved in Et₂O, treated with HCl (g) and evaporated to give amine 212 (as the hydrochloride), which was used without further purification in the synthesis of compound Ib-7.

EXAMPLE T

The preparation of the methylenedioxy substituted isoquinoline building block 258 is described in SchemeT. This building block can be incorporated into compounds such as Ib-39 and I-19 using standard amide bond formation conditions (e.g., HBTU or BOPCl activation).

The dialdehyde 255 was prepared in four steps from the commercially available aldehyde 250 by bromination (Harrowven et al., *Tetrahedron Lett.* 1998, 39, 6757), acetalization/formylation (Boger et al., *J. Org. Chem.* 2000, 65, 9120), and deprotection (according to Dallacker et al., *Z. Naturforsch. B Anorg. Chem. Org. Chem.* 1986, 41, 1273). Treatment of dialdehyde 255 with methyl glycinate 256 and DBU in dioxane gave the isoquinoline ester 257 that was saponified to yield the acid 258.

Scheme T

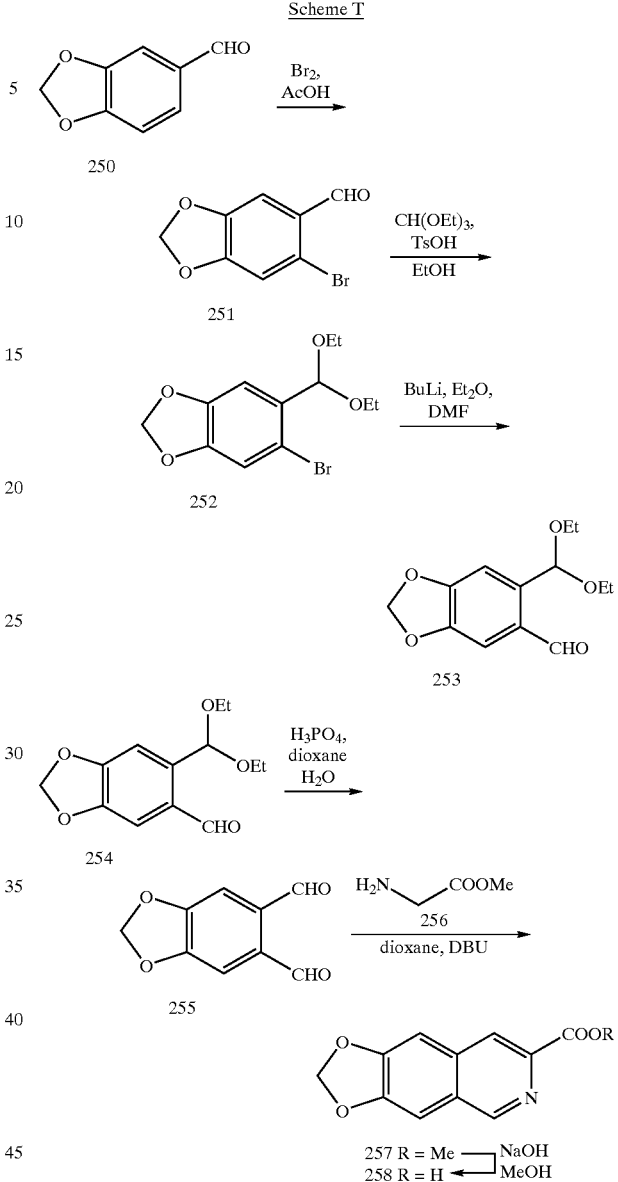

Synthesis of compound 257. A mixture of dialdehyde 255 (1.48 g) and methyl glycinate hydrochloride (0.84 g, 1 equiv.) in dioxane (100 ml) and DBU (1,8-diaza-bicyclo [2.2.2]undec-7-ene, 20 ml) as refluxed for 2 h and solvent was evaporated. The residue was dissolved in AcOEt (300 ml), washed with H₂O, aqueous NH₄Cl, H₂O, brine, dried (Na₂SO₄) and evaporated. Flash chromatography of the crude product (Hex/AcOEt 4:1 to 1:1) gave compound 257 as a solid (200 mg, 10%).

Synthesis of compound 258. A mixture of ester 257 (200 mg) in MeOH (2 ml) and 2M aqueous NaOH (10 ml) was stirred at 70° C. for 12 h, cooled to 0° C., and neutralized to pH≅5 using 6M aqueous HCl. The resulting precipitate was collected by centrifugation, washed with H₂O (2x, each 30 ml) and Et₂O (5 ml), and dried in vacuo to give acid 117 (80 mg, 43%, structure confirmed by $^1$H-NMR).

EXAMPLE U

A 4-nitro-pyrrole bearing a carboxylic ester or an amide function at position 2 can be alkylated at the ring nitrogen. The experimental details for the preparation of the pegylated pyrrole dimer 263 are described below. This dimer was used for the preparation of compound Ib-83 (standard HBTU-mediated coupling of the acid 18 and 263). Other nitro pyrroles, for instance the ethyl 4-nitro-pyrrole-2-carboxylate 41, can be substituted (pegylated) analogously.

dried ($MgSO_4$) and evaporated. Flash chromatography of the resulting oil ($CH_2Cl_2$: 0 to 15% MeOH) gave compound 262 as a yellow solid (785 mg, 57%, structure confirmed by $^1$H-NMR and MS).

Synthesis of amine 263. A suspension of compound 262 (780 mg) and 10% Pd—C (200 mg) in AcOEt (36 ml) and MeOH (4 ml) was stirred at RT under $H_2$ (1 atm) for 22 h and filtered through Celite. The filtrate was treated with HCl

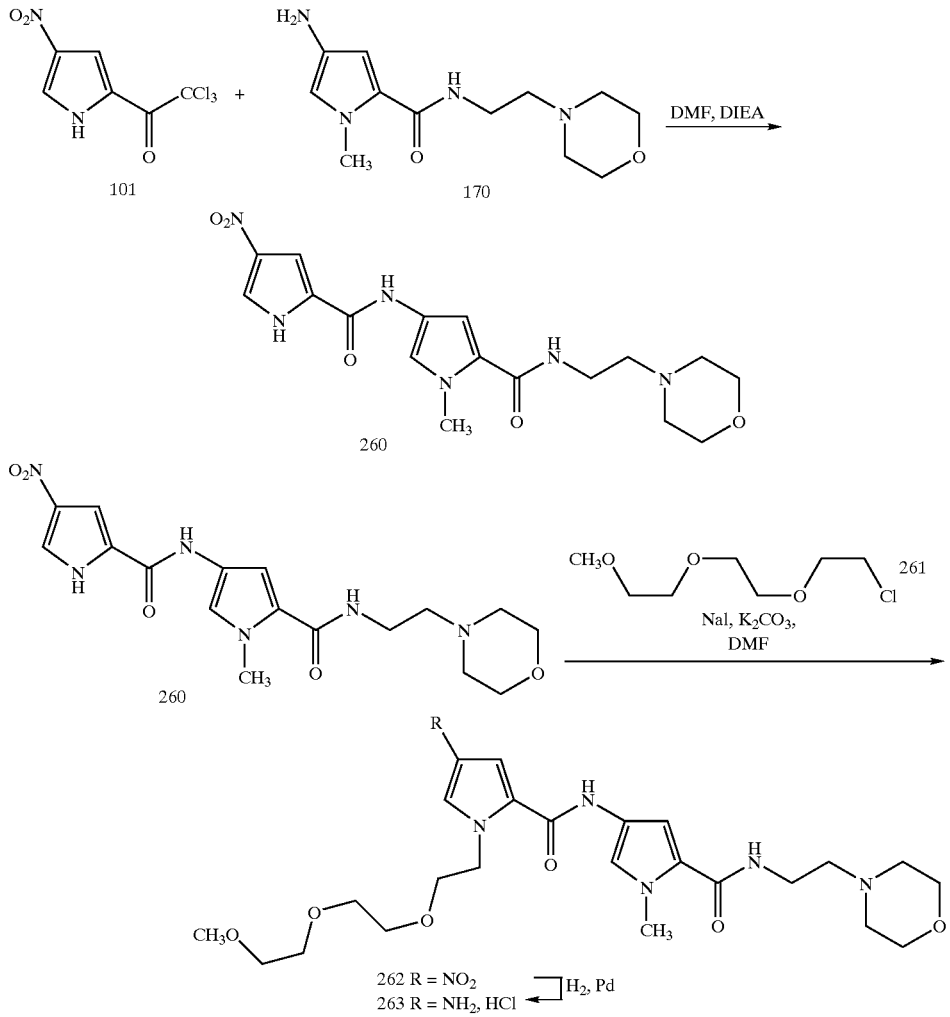

Scheme U

Synthesis of nitro compound 260. A mixture of trichloroketone 101 (11.32 g, 1.0 equiv.), amine 170 (15.00 g, 1.0 equiv.) in DMF (80 ml) and DEA (20 ml) was stirred at RT for 20 h and poured into $H_2O$ (ca. 600 ml) and sat. aqueous $K_2CO_3$. The solution was extracted with AcOEt (6x) and the organic layers were dried ($MgSO_4$) and evaporated to give nitro compound 260 as a yellow solid (structure confirmed by $^1$H-NMR).

Synthesis of pegylated nitro compound 262. A mixture of dimer 260 (1.00 g, 1.0 equiv.), chloride 261 (3.67 g, 2.5 equiv.), NaI (576 mg, 1.5 equiv.), and $K_2CO_3$ (884 mg, 2.5 equiv.) in DMF (ca. 30 ml) was stirred at 65° C. for 48 h, diluted with AcOEt (150 ml), and washed with sat. aqueous $K_2CO_3$ and $H_2O$ (2x). The combined organic layers were (g) for ca. 15 seconds and evaporated to give amine 263 as a tan solid (804 mg, structure confirmed by $^1$H-NMR and MS).

EXAMPLE V

This example describes the synthesis of compounds having a C-terminal quinoline, an N-terminal isoquinoline, and two internal pyrrole units, where one of the internal pyrroles bears an amino alkyl unit. This synthetic strategy allows a broad variation of the nature of the amino alkyl group.

Hydroxypropylated pyrrole intermediate 270 was prepared by alkylation of nitro pyrrole 41 (similarly to intermediates 42–44), followed by reduction of the nitro compound to an amine. Standard HBTU-mediated coupling of the amine and isoquinoline-3-carboxylic acid, followed by saponification afforded dimer 271. Standard HBTU-coupling of dimer 271 with the previously described dimeric amine 80 gave the tetrameric alcohol 272. In situ mesylation of alcohol 272 and nucleophilic aromatic substitution of the mesyloxy group by an amine gave the final compounds (piperidine for Ib-90; pyrrolidine for Ib-91). Experimental details for the synthesis of Ib-90 from 272 are given below.

11778), *Staphylococcus aureus* (ATCC 27660, a methicillin resistant strain (MRSA); ATCC 13709, a methicillin sensitive strain (MSSA)); *Streptococcus pneumoniae* (ATCC 51422, a penicillin resistant strain (PRSP)), *Enterococcus faecium* (ATCC 51559, a vancomycin resistant strain (VRE)), and *Staphylococcus epidermidis* (ATCC 12228). Additionally, antifungal activity data were collected for *Candida albicans* (ATCC 38247). Compounds of this inven- Scheme V

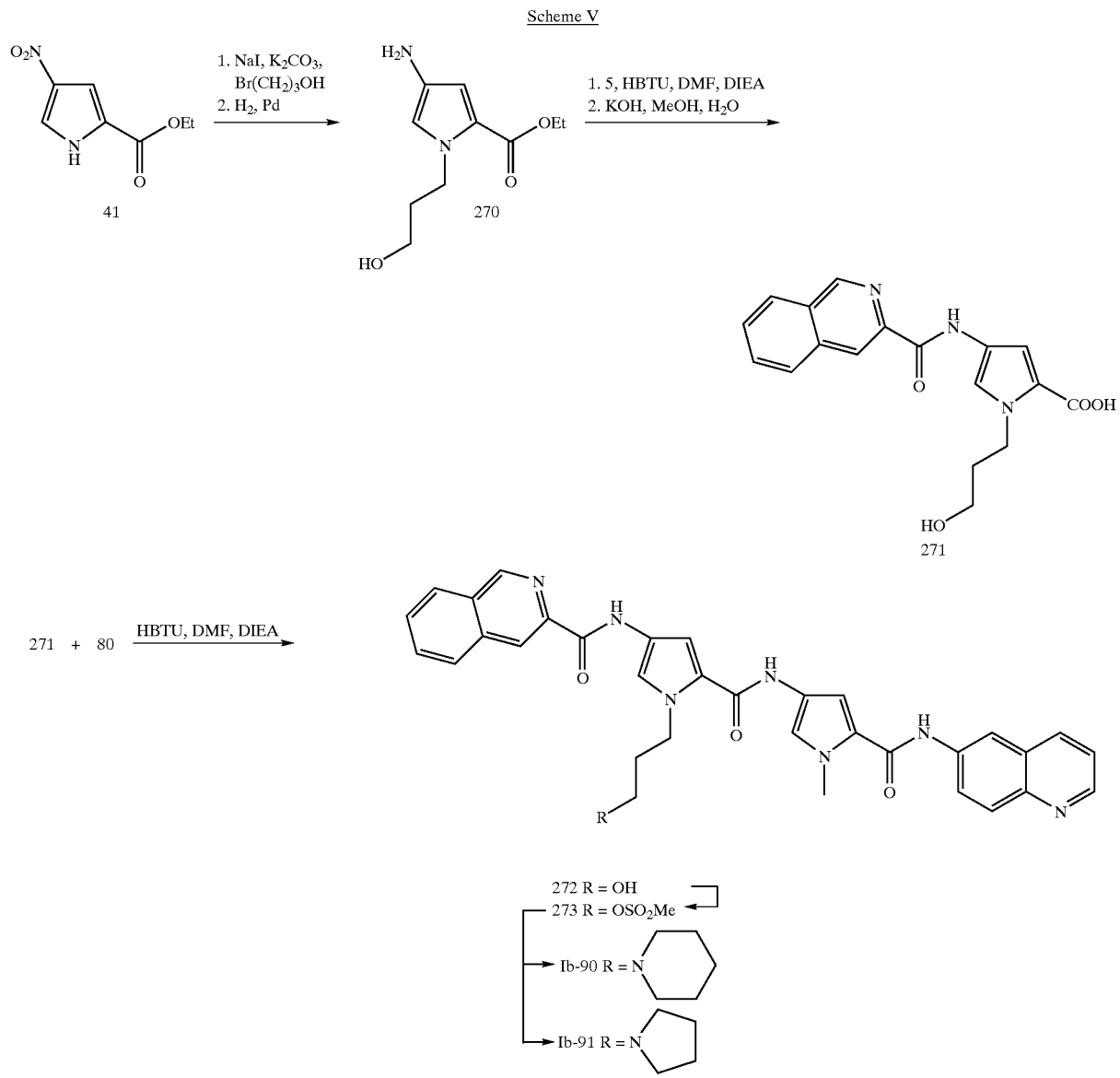

Synthesis of compound Ib-90. A solution of alcohol 272 (100 mg) in DMF (1 ml, dried over 4 Å molecular sieves) and DIEA (0.2 ml) was treated at RT under $N_2$ with methanesulfonyl chloride (freshly destilled, 0.10 ml) and stirred for 1 h. The mixture was treated with piperidine (0.25 ml), stirred for 12 h at 60° C. and diluted with 50% aqueous AcOH (10 ml). Purification by RP-HPLC gave compound Ib-90 (structure confirmed by $^1$H-NMR and MS).

In Vitro Biological Activity

In vitro biological activity data were collected for a variety of microorganisms, including *Bacillus cereus* (ATCC tion preferably have an MIC of 4 or less against a drug resistant bacterial strain, such as one of the foregoing.

Compounds according to this invention were screened for their in vitro activities against selected species of bacteria and fungi. The minimal inhibition concentration ((MIC) of these compounds was determined using the National Committee for Clinical Laboratory Standards (NCCLS) broth microdilution assay in microtiter plates, as set forth in: (1) the guidelines of the National Committee for Clinical Laboratory Standards (NCCLS) Document M7-A4 (NCCLS, 1997); (2) the guidelines of the National Committee for Clinical Laboratory Standards (NCCLS) Document M11-

A4 (NCCLS, 1997); and (3) the guidelines and reference method of the National Committee for Clinical Laboratory Standards (NCCLS) Document M27-T (NCCLS, 1995). For antifungal assays, the method recommended in Murray, P.R., 1995 *Manual of Clinical Microbiology* (ASM Press, Washington, D.C.), was employed. The results are presented in Table B below, which is keyed as follows:

Key to organisms tested against:

A = *B. cereus* ATCC 11778  B = *C. albicans* ATCC 38247
C = *E. faecalis* ATCC 29212  D = *E. faecium* ATCC 51559
E = *S. aureus* ATCC 13709  F = *S. aureus* ATCC 27660
G = *S. epidermidis* ATCC 12228  H = *S. pneumoniae* ATCC 49619
I = *S. pneumoniae* ATCC 51422
Key to activity:

+++ = MIC ≤ 4  ++ = 4 < MIC < 12
+ = 12 ≤ MIC ≤ 32  ND = not determined
>32 = preliminary data indicates MIC greater than 32

TABLE B

| Cpd. Ref. | A | B | C | D | E | F | G | H | I |
|---|---|---|---|---|---|---|---|---|---|
| Ib-1 | +++ | >32 | +++ | ND | ND | ND | ND | +++ | ND |
| Ib-2 | +++ | >32 | +++ | +++ | +++ | +++ | +++ | +++ | +++ |
| Ib-3 | +++ | >32 | +++ | +++ | +++ | +++ | +++ | +++ | +++ |
| Ib-4 | +++ | ++ | +++ | +++ | +++ | +++ | +++ | +++ | +++ |
| Ib-5 | +++ | +++ | +++ | ND | +++ | +++ | ND | +++ | ND |
| Ib-6 | +++ | >32 | +++ | ++ | +++ | +++ | ++ | +++ | +++ |
| Ib-7 | +++ | >32 | +++ | +++ | +++ | +++ | +++ | +++ | +++ |
| Ib-8 | +++ | >32 | +++ | ND | +++ | +++ | ND | +++ | ND |
| Ib-9 | +++ | >32 | +++ | ND | +++ | +++ | ND | +++ | ND |
| Ib-10 | +++ | >32 | +++ | ND | +++ | +++ | ND | +++ | ND |
| Ib-11 | ++ | >32 | ++ | + | ++ | ++ | ++ | +++ | ++ |
| Ib-12 | +++ | + | +++ | ND | +++ | +++ | ND | +++ | ND |
| Ib-13 | +++ | >32 | +++ | +++ | +++ | +++ | +++ | +++ | +++ |
| Ib-14 | +++ | >32 | +++ | ND | +++ | +++ | ND | +++ | ND |
| Ib-15 | + | >32 | + | ND | ++ | ++ | ND | ++ | ND |
| Ib-16 | +++ | >32 | +++ | ND | +++ | +++ | ND | +++ | ND |
| Ib-17 | +++ | >32 | +++ | ND | +++ | +++ | ND | +++ | ND |
| Ib-18 | +++ | >32 | +++ | +++ | +++ | +++ | ++ | +++ | +++ |
| Ib-19 | +++ | >32 | +++ | + | +++ | +++ | +++ | +++ | +++ |
| Ib-20 | +++ | + | +++ | ND | +++ | +++ | ND | +++ | ND |
| Ib-21 | +++ | ++ | +++ | +++ | +++ | +++ | +++ | +++ | +++ |
| Ib-22 | +++ | >32 | +++ | ND | ++ | +++ | ND | +++ | ND |
| Ib-23 | +++ | + | + | ND | +++ | +++ | ND | + | ND |
| Ib-24 | +++ | >32 | +++ | ND | +++ | +++ | ND | +++ | ND |
| Ib-25 | + | >32 | ++ | ND | + | ++ | ND | +++ | ND |
| Ib-26 | +++ | >32 | +++ | ND | +++ | +++ | ND | +++ | ND |
| Ib-27 | +++ | >32 | +++ | ND | +++ | +++ | ND | +++ | ND |
| Ib-28 | + | >32 | + | ND | ++ | +++ | ND | +++ | ND |
| Ib-29 | +++ | >32 | +++ | ND | +++ | +++ | ND | +++ | ND |
| Ib-30 | +++ | >32 | +++ | ND | +++ | +++ | ND | +++ | ND |
| Ib-31 | +++ | >32 | +++ | ND | +++ | +++ | ND | +++ | ND |
| Ib-32 | ++ | >32 | +++ | ND | ++ | + | ND | +++ | ND |
| Ib-33 | >32 | >32 | >32 | ND | + | + | ND | +++ | ND |
| Ib-34 | +++ | + | ++ | ND | ++ | +++ | ND | +++ | ND |
| Ib-35 | +++ | >32 | +++ | ND | +++ | +++ | +++ | +++ | +++ |
| Ib-36 | +++ | >32 | +++ | +++ | +++ | +++ | +++ | +++ | +++ |
| Ib-37 | +++ | >32 | +++ | +++ | +++ | +++ | +++ | +++ | +++ |
| Ib-38 | +++ | >32 | +++ | ND | +++ | +++ | ND | +++ | ND |
| Ib-50 | +++ | >32 | +++ | +++ | +++ | +++ | +++ | +++ | +++ |
| Ib-51 | +++ | ++ | +++ | ++ | +++ | +++ | ++ | +++ | + |
| Ib-52 | +++ | >32 | +++ | +++ | +++ | +++ | +++ | +++ | +++ |
| Ib-53 | +++ | >32 | +++ | ND | +++ | +++ | ND | +++ | ND |
| Ib-54 | +++ | >32 | +++ | +++ | +++ | +++ | ++ | +++ | +++ |
| Ib-55 | +++ | >32 | +++ | ++ | +++ | +++ | +++ | +++ | +++ |
| Ib-56 | +++ | >32 | +++ | ++ | +++ | +++ | +++ | +++ | +++ |
| Ib-57 | +++ | >32 | +++ | ND | +++ | +++ | ND | +++ | ND |
| Ib-58 | >32 | >32 | +++ | ND | ++ | >32 | ND | +++ | ND |
| Ib-59 | +++ | >32 | +++ | +++ | +++ | +++ | +++ | +++ | +++ |
| Ib-60 | +++ | >32 | +++ | ND | +++ | ND | ND | +++ | ND |
| Ib-61 | >32 | >32 | +++ | ND | + | +++ | ND | +++ | ND |
| Ib-62 | +++ | >32 | +++ | ND | ++ | +++ | ND | +++ | ND |
| Ib-63 | +++ | >32 | +++ | ND | +++ | +++ | ND | +++ | ND |
| Ib-64 | +++ | +++ | +++ | ND | +++ | +++ | ND | +++ | ND |
| Ib-65 | +++ | >32 | +++ | ND | +++ | +++ | ND | +++ | ND |
| Ib-66 | +++ | +++ | +++ | ++ | +++ | +++ | +++ | +++ | +++ |
| Ib-67 | +++ | >32 | +++ | ND | +++ | +++ | ND | +++ | ND |
| Ib-68 | +++ | + | +++ | ND | +++ | +++ | ND | +++ | ND |
| Ib-69 | +++ | >32 | +++ | ND | +++ | +++ | ND | +++ | ND |
| Ib-70 | +++ | >32 | +++ | ND | +++ | +++ | ND | +++ | ND |
| Ib-71 | +++ | >32 | +++ | ND | +++ | +++ | ND | +++ | ND |
| Ib-72 | +++ | >32 | +++ | ND | +++ | +++ | ND | +++ | ND |
| Ib-73 | +++ | +++ | +++ | ND | +++ | +++ | ND | +++ | ND |
| Ib-74 | >32 | >32 | >32 | ND | >32 | >32 | ND | >32 | ND |
| Ib-75 | +++ | >32 | +++ | ND | +++ | +++ | ND | +++ | ND |
| Ib-76 | +++ | >32 | +++ | ND | +++ | +++ | ND | +++ | ND |
| Ib-77 | +++ | >32 | +++ | ND | +++ | +++ | ND | +++ | ND |
| Ib-78 | +++ | >32 | +++ | +++ | +++ | +++ | +++ | +++ | +++ |
| Ib-79 | +++ | >32 | +++ | ND | +++ | +++ | ND | +++ | ND |
| Ib-80 | +++ | +++ | +++ | ND | +++ | +++ | ND | +++ | ND |
| Ib-81 | +++ | + | +++ | ND | +++ | +++ | ND | +++ | ND |
| Ib-82 | +++ | + | +++ | ND | +++ | +++ | ND | +++ | ND |
| Ib-83 | +++ | >32 | +++ | +++ | +++ | +++ | +++ | +++ | +++ |
| Ib-84 | +++ | + | +++ | +++ | +++ | +++ | +++ | +++ | +++ |
| Ib-85 | +++ | + | +++ | +++ | +++ | +++ | +++ | +++ | +++ |
| Ib-86 | +++ | ++ | +++ | +++ | +++ | +++ | +++ | +++ | +++ |
| Ib-87 | +++ | >32 | +++ | +++ | +++ | +++ | +++ | +++ | +++ |
| Ib-88 | +++ | >32 | +++ | +++ | +++ | +++ | +++ | +++ | +++ |
| Ib-89 | +++ | + | +++ | ND | +++ | +++ | ND | +++ | ND |
| Ib-90 | +++ | + | +++ | ND | +++ | +++ | ND | +++ | ND |
| Ib-91 | +++ | >32 | +++ | ND | +++ | +++ | ND | +++ | ND |
| Ib-92 | +++ | >32 | +++ | ND | +++ | +++ | ND | +++ | ND |
| Ib-93 | +++ | >32 | +++ | +++ | +++ | +++ | +++ | +++ | +++ |
| Ic-1 | +++ | >32 | +++ | +++ | +++ | +++ | +++ | +++ | +++ |
| Ic-2 | +++ | >32 | +++ | ND | +++ | +++ | ND | +++ | ND |
| Ic-3 | +++ | >32 | +++ | +++ | +++ | +++ | +++ | +++ | +++ |
| Ic-4 | +++ | >32 | +++ | +++ | +++ | +++ | +++ | +++ | +++ |
| Ic-5 | + | >32 | +++ | ND | +++ | +++ | ND | +++ | ND |
| Ic-6 | +++ | >32 | +++ | ND | +++ | +++ | ND | +++ | ND |
| Ic-7 | +++ | >32 | +++ | +++ | +++ | +++ | +++ | +++ | +++ |
| Ic-8 | +++ | >32 | +++ | ND | +++ | +++ | ND | +++ | ND |
| Ic-9 | +++ | >32 | +++ | ND | +++ | +++ | ND | +++ | ND |
| Ic-10 | +++ | >32 | +++ | ND | +++ | +++ | ND | +++ | ND |
| Ic-11 | >32 | >32 | +++ | ND | +++ | +++ | ND | +++ | ND |
| Ic-12 | >32 | >32 | +++ | +++ | +++ | +++ | +++ | +++ | +++ |
| Ic-13 | +++ | >32 | +++ | +++ | +++ | +++ | +++ | +++ | +++ |
| Ic-14 | >32 | >32 | >32 | ND | +++ | +++ | ND | +++ | ND |
| Ic-15 | >32 | >32 | >32 | ND | +++ | +++ | ND | +++ | ND |
| Ic-16 | +++ | >32 | +++ | ND | +++ | +++ | ND | +++ | ND |
| Ic-17 | +++ | >32 | +++ | ND | +++ | +++ | ND | +++ | ND |
| Ic-18 | +++ | >32 | +++ | ND | +++ | +++ | ND | +++ | ND |
| Id-1 | +++ | >32 | +++ | ND | +++ | +++ | ND | +++ | ND |

In Vivo Biological Data

This example demonstrates in vivo efficacy against infection by methicillin resistant Staphylococcus aureus ATCC 33591, using a murine neutropenic thigh model.

A *S. aureus* ATCC 33591 culture was grown to log phase overnight and diluted in phosphate buffered saline (pH 7.2) to an optical density of about 0.1 at 600 nm, giving an approximate concentration of $10^8$ cfu/mL. The suspension was diluted 1:100 in phosphate buffered saline (pH 7.2) for a final concentration of $10^6$ cfu/mL.

Outbred female CF1 mice (approx. 20 gram body weight) were rendered neutropenic by treatment with cyclophosphamide (200 mg/kg body weight, intraperitoneal injection) at 2 and 4 days prior to inoculation. Groups of 5 mice were inoculated with 0.05 mL of the bacteria (approx. $10^6$ cfu/mL) into the anterior thigh. Each group was treated intravenously two hours post infection with vehicle (phosphate buffered saline) or test compound. The mice were sacrificed at either 6 or 24 hrs after treatment and thighs were collected aseptically. Each thigh was weighed, placed into sterile saline, and homogenized. The tissue homogenates were diluted appropriately for plating on agar plates. Colony counts were recorded (cfu/gram) and compared to control groups. The data are presented in Table C below:

TABLE C

Murine Neutropenic Thigh Model

| Compound No. | Dose | Colony Count (log cfu/gram) | |
|---|---|---|---|
| (Time) | (mg/kg) | Compound | Vehicle |
| Ib-4 (6 hr) | 50 | 7.73 | 8.76 |
| Ib-8 (6 hr) | 50 | 5.41 | 8.29 |
| Ib-55 (6 hr) | 50 | 5.73 | 8.29 |
| Ib-55 (6 hr) | 25 | 6.54 | 7.74 |
| Ib-66 (6 hr) | 50 | 6.66 | 7.99 |
| Ib-67 (6 hr) | 50 | 5.79 | 7.88 |
| Ib-67 (6 hr) | 25 | 6.61 | 7.74 |
| Ib-68 (6 hr) | 50 | 6.36 | 7.88 |

In vivo efficacy was shown by a decrease in colony count (log cfu/gram of tissue) in the compound-treated animals when compared against the colony count in animals given only the vehicle.

DNA Binding

This example illustrates the DNA binding properties of compounds of this invention using a DNase I footprinting technique. Generally, the procedure described in Dervan, WO 98/50582 (1998), was followed.

Double stranded circular plasmids A and B were used to prepare double stranded DNA-binding probes containing the target sequences for the DNase I footprint titration experiments.

Plasmid A was prepared by hybridizing two sets of 5'-phosphorylated complementary oligonucleotides, the first set being
5'-CTAGATGCCGCTAAGTACTATGCCGCTAACTACTATGCCGCTAAT TACTATGCCGC-3' (SEQ ID NO:3) and
5'-CATAGTAATTAGCGGCATAGTAGTTAGCGGCATAGTACTTAGCGGC-3' (SEQ ID NO:4); and the second set being
5'-TAAATACTATGCCGCTAACTAGTATGCCGCTATGCA-3' (SEQ ID NO:5) and
5'-TAGCGGCATACTAGTTAGCGGCATAGTATTTAGCGG-3' (SEQ ID NO:6), and ligating the resulting duplexes to the large pUC19 XbaI/PstI restriction fragment.

Plasmid B was the plasmid pTrc99a, obtained from Amersham Pharmacia Biotech, Inc.

The 3'-$^{32}$P end-labeled EcoRI/PvuII fragments from each plasmid were prepared by digesting the plasmids with EcoRI and PvuII with simultaneous fill-in using Sequenase v. 2.0, [alpha-$^{32}$P]-deoxyadenosine-5'-triphosphate, and [alpha-$^{32}$P]-thymidine-5'-triphosphate, and isolating the cloned fragments by nondenaturing gel electrophoresis. A and G sequencing reactions were carried out as described (See Maxam and Gilbert, *Methods Enzymol.*, 1980, 65, 499–560; Iverson and Dervan, *Methods Enzymol.*, 1987, 15, 7823–7830; Sambrook et al., 1989, *Molecular Cloning*, 2$^{nd}$ ed., Cold Spring Harbor Laboratory Press: Cold Spring Harbor, N.Y.) Standard methods were used for all DNA manipulations (Sambrook et al., ibid.)

The 310 base pair dsDNA restriction fragment (SEQ ID NO:1) of Plasmid A contained a target sequence AGTACT. The 352 base pair dsDNA restriction fragment (SEQ ID NO:2) of Plasmid B contained target sequences ACAATTAT and AATTAATCAT (SEQ ID NO:7). These fragments were used for quantitative DNase I footprinting experiments. The target sequences were selected for their identity with, or similarity to, promoter sites for bacterial genes.

Quantitative DNase I footprint titration experiments were carried out as described previously (Dervan, WO 98/50582, 1998) with the following changes. All reactions were carried out in a total volume of 400 µL, with compound stock solution or water added to 15,000 cpm radiolabeled restriction fragment affording final solution conditions of 10 mM TrisHCl, 10 mM KCl, 10 mM MgCl$_2$, 5 mM CaCl$_2$, pH 7.0 and 0.01 nM, 0.1 nM, 1.0 nM, 10.0 nM compound or no compound for reference lanes. The compounds were allowed to equilibrate at 22° C. for 16 hr. Footprinting reactions were initiated with addition of 10 µL of a DNase I stock solution (at the appropriate concentration to give ~50% intact DNA) containing 1 mM DTT and allowed to proceed for 7 min at 22° C. The reactions were stopped, ethanol precipitated, resuspended in loading buffer, heat denatured, and placed on ice as described previously (Dervan WO 98/50582, 1998). The reaction products were separated on a precast 8% polyacrylamide denaturing sequencing Castaway gel with 32 preformed wells from Stratagene in 1×TBE at 2000 V. Gels were dried according to the manufacturer and exposed to a storage phosphor screen (Molecular Dynamics). Quantitation and data analysis were carried out as described in Dervan, WO 98/50582, 1998.

dsDNA binding results are provided in Table C:

TABLE 7 dsDNA Binding

| Compound | Target Sequence | Dissociation Constant K$_d$ (nM) | Target Location (Fragment/Plasmid) |
|---|---|---|---|
| Ib-19 | AGTACT | 50 | 310 bp/A |
| Ib-19 | ACAATTAT | 5 | 352 bp/B |
| Ib-56 | AGTACT | <100 | 310 bp/A |
| Ib-56 | AATTAATCAT | 5 | 352 bp/B |
| Ib-59 | AGTACT | 50 | 310 bp/A |
| Ib-59 | ACAATTAAT | 1 | 352 bp/B |
| Ib-60 | AGTACT | 10 | 310 bp/A |
| Ib-60 | AATTAATCAT | 5 | 352 bp/B |

SEQUENCE LISTINGS (310 bp EdoRI/PvuII restriction fragment from Plasmid A; only one strand shown)

SEQ ID NO.I
AATTCGAGCTCGGTACCCGGGGATCCTCTAGATGCCGCTAAGTACTATGC

CGCTAACTACTATGCCGCTAATTACTATGCCGCTAAATACTATGCCGCTA

ACTAGTATGCCGCTATGCAGGCATGCAAGCTTGGCGTAATCATGGTCATA

GCTGTTTCCTGTGTGAAATTGTTATCCGCTCACAATTCCACACAACATAC

GAGCCGGAAGCATAAAGTGTAAAGCCTGGGGTGCCTAATGAGTGAGCTAA

CTCACATTAATTGCGTTGCGCTCACTGCCCGCTTTCCAGTCGGGAAACCT

GTCGTGCCAG (352 bp EdoRI/PvuII restriction fragment from Plasmid B; only one strand shown)

SEQ ID NO.II
CTGGCACGACAGGTTTCCCGACTGGAAAGCGGGCAGTGAGCGCAACGCAA

TTAATGTGAGTTAGCGCGAATTGATCTGGTTTGACAGCTTATCATCGACT

-continued

SEQUENCE LISTINGS

GCACGGTGCACCAATGCTTCTGGCGTCAGGCAGCCATCGGAAGCTGTGGT

ATGGCTGTGCAGGTCGTAAATCACTGCATAATTCGTGTCGCTCAAGGCGC

ACTCCCGTTCTGGATAATGTTTTTTGCGCCGACATCATAACGGTTCTGGC

AAATATTCTGAAATGAGCTGTTGACAATTAATCATCCGGCTCGTATAATG

TGTGGAATTGTGAGCGGATAACAATTTCACACAGGAAACAGACCATGGAA

TT

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

---

What is claimed is:

1. A compound according to the formula

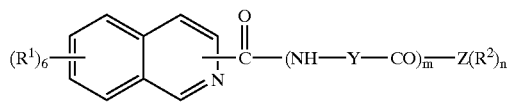

and the pharmaceutically acceptable salts thereof, wherein each $R^1$ is independently H, F, Cl, Br, I, CN, OH, $NO_2$, $NH_2$, a substituted or unsubstituted $(C_1–C_{12})$alkyl group, a substituted or unsubstituted $(C_1–C_{12})$alkoxy group, or a substituted or unsubstituted $(C_1–C_{12})$ heteroalkyl group;

m is an integer from 1 to 25, inclusive;

each Y is independently a branched or unbranched, substituted or unsubstituted $(C_1–C_5)$alkylene group or a substituted or unsubstituted, aromatic or heteroaromatic ring system, wherein the ring system has a 5- or 6-member aromatic or heteroaromatic rings or fused 6,6 or 6,5 aromatic or heteroaromatic rings, wherein at least one residue Y is a 5- or 6-member heteroaromatic ring;

Z is either O or N;

n is 1 if Z is O and 2 if Z is N; and each $R^2$ is independently H, a substituted or unsubstituted $(C_1-C_{12})$alkyl group, or a substituted or unsubstituted $(C_1-C_{12})$heteroalkyl group;

the compound having a basic group having a $pK_b$ of 12 or less or a quaternized nitrogen group.

2. A compound of the formula

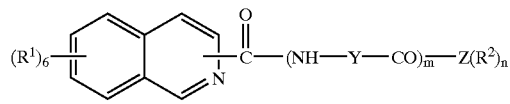

and the pharmaceutically acceptable salts thereof, wherein m is an integer from 1 to 25, inclusive;

each moiety —(NH—Y—CO)— is independently selected from the group consisting of
(a) moieties $M^1$ of the formula

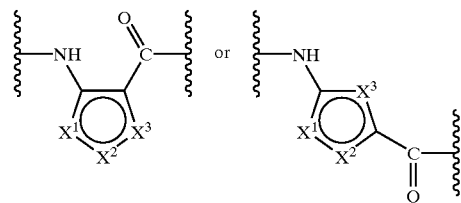

wherein one of $X^1$, $X^2$, and $X^3$ is a ring vertex selected from the group consisting of —O—, —S—, and —$NR^2$—, and the other two of $X^1$, $X^2$, and $X^3$ are ring vertices selected from the group consisting of =N— and =$CR^1$—;
(b) moieties $M^2$ of the formula

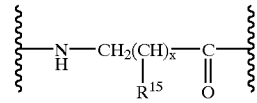

wherein x is 0 or 1 and each $R^{15}$ is independently H, OH, $NH_2$, or F;
(c) moieties $M^3$ of the formula

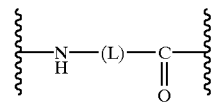

wherein each L is independently a divalent moiety separating —NH— and —(C=O)— by 3 or 4 atoms; and (d) moieties $M^4$ of the formula

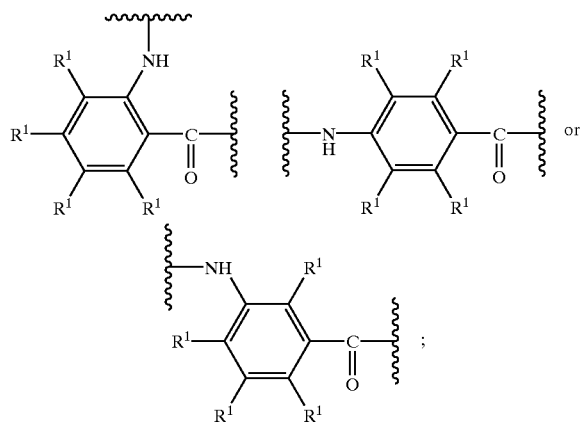

wherein at least one moiety —(NH—Y—CO)— is $M^1$;

Z is O or N;

n is 1 if Z is O and 2 if Z is N;

each $R^1$ is independently H, F, Cl, Br, I, CN, OH, $NO_2$, $NH_2$, a substituted or unsubstituted $(C_1-C_{12})$alkyl group, a substituted or unsubstituted $(C_1-C_{12})$alkoxy group, or a substituted or unsubstituted $(C_1-C_{12})$ heteroalkyl group; and each $R^2$ is independently H, a substituted or unsubstituted $(C_1-C_{12})$alkyl group, or a substituted or unsubstituted $(C_1-C_{12})$heteroalkyl group;

the compound having a basic group having a $pK_b$ of 12 or less or a quaternized nitrogen group.

3. A compound according to claim 2, wherein the residue $Z(R^2)_n$ contains a basic group having a $pK_b$ of 12 or less or a quaternized nitrogen group.

4. A compound according to claim 2, wherein the residue

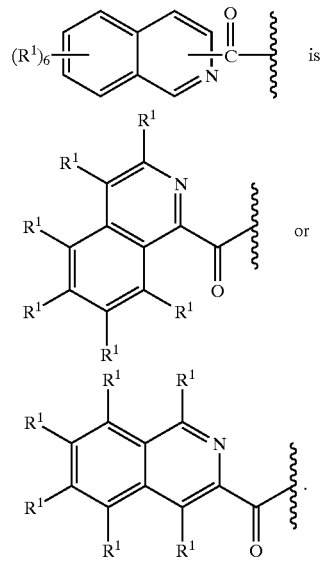

5. A compound according to claim 4, wherein each $R^1$ is H.

6. A compound according to claim 2, wherein the residue

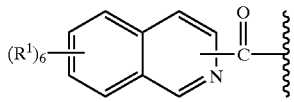

is

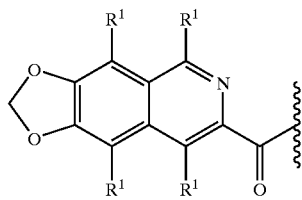

7. A compound according to claim 6, wherein each $R^1$ is H.

8. A compound according to claim 2, having the formula

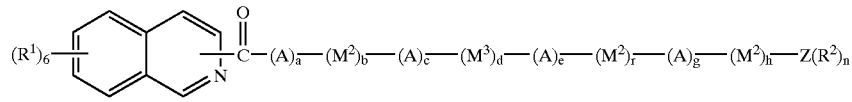

wherein $M^2$, $M^3$, $R^1$, $R^2$, Z and n have the meanings assigned in claim 3; each A is independently $M^1$ or $M^4$ as defined in claim 4; each of a, c, e, g and h is an integer independently from 0 to 5, inclusive; and each of b, d, and f is independently 0 or 1; with the sum of a, c, e, and g being at least 2.

9. A compound according to claim 2, having the formula

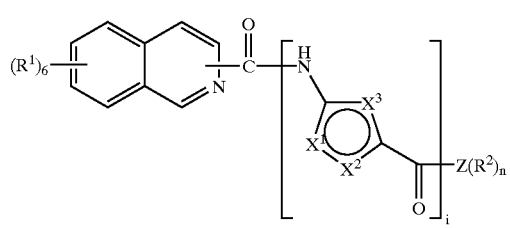

wherein $X^1$, $X^2$, $X^3$, $R^1$, $R^2$, Z, and n have the meanings assigned in claim 3 and i is an is integer between 2 and 4, inclusive.

10. A compound according to claim 9, wherein a residue

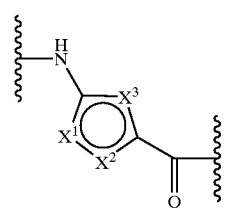

has a basic group having a $pK_b$ of 12 or less or a quaternized nitrogen group.

11. A compound according to claim 9, wherein each residue

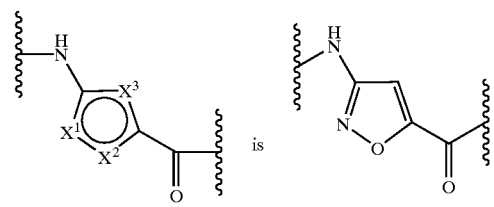

is

12. A compound according to claim 9, wherein at least one residue

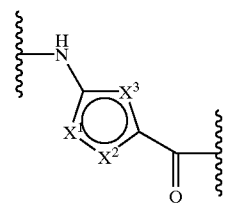

is selected from the group consisting of

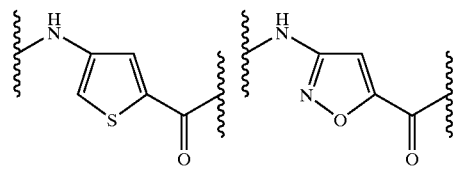

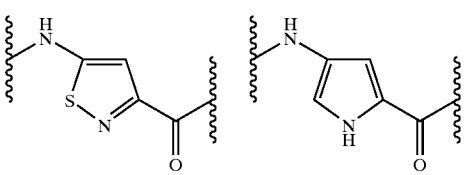

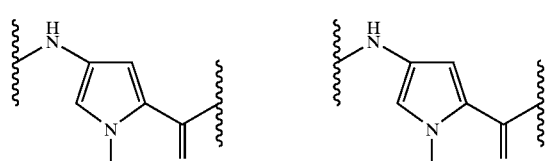

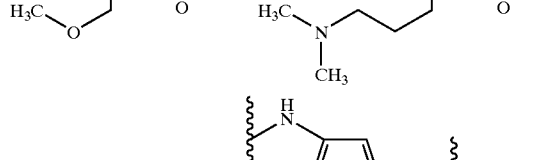

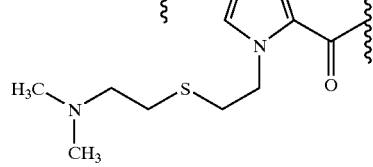

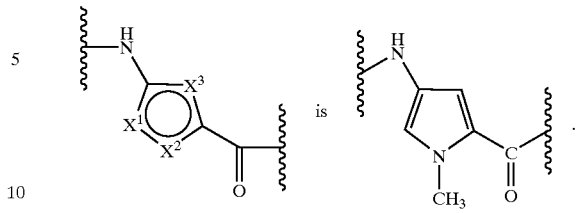

14. A compound according to claim 2, having the formula

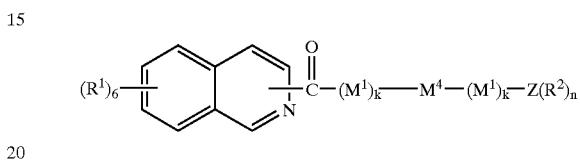

wherein $M^1$, $M^4$, $R^1$, $R^2$, Z, and n are as defined in claim 2 and each k is independently an integer from 0 to 4, inclusive.

15. A compound according to claim 14, having the formula

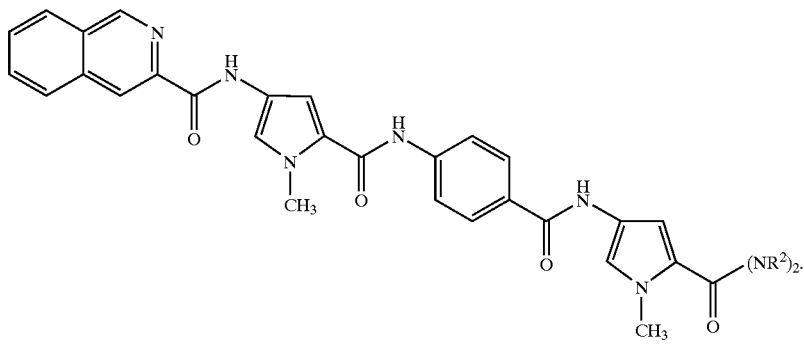

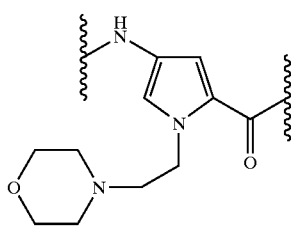

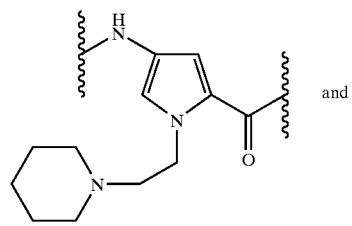
and

-continued

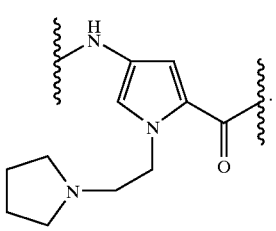

13. A compound according to claim 9, wherein at least one residue

16. A method of treating a bacterial infection in a mammal, comprising administering to a patient in need of such treatment an effective amount of a compound according to claim 1.

17. A method according to claim 16, wherein the bacterial infection is an infection by Gram-positive bacteria.

18. A method according to claim 16, wherein the bacterial infection is an infection by drug resistant bacteria.

19. A method according to claim 18, wherein the drug resistant bacteria is MRSA, MRSE, PRSP, or VSE.

20. A method of treating a bacterial infection in a mammal, comprising administering to a patient in need of such treatment an effective amount of a compound according to claim 2.

21. A method according to claim 20, wherein the bacterial infection is an infection by Gram-positive bacteria.

22. A method according to claim 20, wherein the bacterial infection is an infection by drug resistant bacteria.

23. A method according to claim 22, wherein the drug resistant bacteria is MRSA, MRSE, PRSP, or VSE.

* * * * *

SEQUENCE LISTING

<160> NUMBER OF SEQ ID NOS: 7

<210> SEQ ID NO 1
<211> LENGTH: 310
<212> TYPE: DNA
<213> ORGANISM: Artificial Sequence
<220> FEATURE:
<223> OTHER INFORMATION: Description of Artificial Sequence:310 bp
      EdoRI/PvuII dsDNA restriction fragment from
      Plasmid A

<400> SEQUENCE: 1

```
aattcgagct cggtacccgg ggatcctcta gatgccgcta agtactatgc cgctaactac      60
tatgccgcta attactatgc cgctaaatac tatgccgcta actagtatgc cgctatgcag     120
gcatgcaagc ttggcgtaat catggtcata gctgtttcct gtgtgaaatt gttatccgct    180
cacaattcca cacaacatac gagccggaag cataaagtgt aaagcctggg gtgcctaatg    240
agtgagctaa ctcacattaa ttgcgttgcg ctcactgccc gctttccagt cgggaaacct    300
gtcgtgccag                                                           310
```

<210> SEQ ID NO 2
<211> LENGTH: 352
<212> TYPE: DNA
<213> ORGANISM: Artificial Sequence
<220> FEATURE:
<223> OTHER INFORMATION: Description of Artificial Sequence:352 bp
      EdoRI/PvuII dsDNA restriction fragment from
      Plasmid B

<400> SEQUENCE: 2

```
ctggcacgac aggtttcccg actggaaagc gggcagtgag cgcaacgcaa ttaatgtgag      60
ttagcgcgaa ttgatctggt ttgacagctt atcatcgact gcacggtgca ccaatgcttc    120
tggcgtcagg cagccatcgg aagctgtggt atggctgtgc aggtcgtaaa tcactgcata    180
attcgtgtcg ctcaaggcgc actcccgttc tggataatgt tttttgcgcc gacatcataa    240
cggttctggc aaatattctg aaatgagctg ttgacaatta atcatccggc tcgtataatg    300
tgtggaattg tgagcggata acaatttcac acaggaaaca gaccatggaa tt            352
```

<210> SEQ ID NO 3
<211> LENGTH: 56

```
<212> TYPE: DNA
<213> ORGANISM: Artificial Sequence
<220> FEATURE:
<223> OTHER INFORMATION: Description of Artificial
      Sequence:5'-phosphorylated complementary
      oligonucleotides

<400> SEQUENCE: 3
ctagatgccg ctaagtacta tgccgctaac tactatgccg ctaattacta tgccgc       56

<210> SEQ ID NO 4
<211> LENGTH: 48
<212> TYPE: DNA
<213> ORGANISM: Artificial Sequence
<220> FEATURE:
<223> OTHER INFORMATION: Description of Artificial
      Sequence:5'-phosphorylated complementary
      oligonucleotides

<400> SEQUENCE: 4
catagtaatt agcggcatag tagttagcgg catagtactt agcggcat              48

<210> SEQ ID NO 5
<211> LENGTH: 36
<212> TYPE: DNA
<213> ORGANISM: Artificial Sequence
<220> FEATURE:
<223> OTHER INFORMATION: Description of Artificial
      Sequence:5'-phosphorylated complementary
      oligonucleotides

<400> SEQUENCE: 5
taaatactat gccgctaact agtatgccgc tatgca                           36

<210> SEQ ID NO 6
<211> LENGTH: 36
<212> TYPE: DNA
<213> ORGANISM: Artificial Sequence
<220> FEATURE:
<223> OTHER INFORMATION: Description of Artificial
      Sequence:5'-phosphorylated complementary
      oligonucleotides

<400> SEQUENCE: 6
tagcggcata ctagttagcg gcatagtatt tagcgg                           36

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence:target
      sequence of Plasmid B

<400> SEQUENCE: 7
aattaatcat                                                        10
```